(12) United States Patent
Pachot et al.

(10) Patent No.: US 11,821,038 B2
(45) Date of Patent: *Nov. 21, 2023

(54) METHOD FOR DIAGNOSIS AND/OR PROGNOSIS OF A SEPTIC SYNDROME

(71) Applicant: BIOMERIEUX, Marcy L'Etoile (FR)

(72) Inventors: Alexandre Pachot, Sulignat (FR);
Guillaume Monneret, Lyons (FR);
Alain Lepape, Saint-Genis-Laval (FR)

(73) Assignee: BIOMERIEUX, Marcy l'Etoile (FR)

( * ) Notice: Subject to any disclaimer, the term of this patent is extended or adjusted under 35 U.S.C. 154(b) by 150 days.

This patent is subject to a terminal disclaimer.

(21) Appl. No.: 17/200,178

(22) Filed: Mar. 12, 2021

(65) Prior Publication Data

US 2021/0207220 A1  Jul. 8, 2021

Related U.S. Application Data

(63) Continuation of application No. 11/794,690, filed as application No. PCT/FR2006/050070 on Jan. 30, 2006, now Pat. No. 11,060,143.

(30) Foreign Application Priority Data

Jan. 31, 2005 (FR) ........................ 0550267

(51) Int. Cl.
*C12Q 1/6883* (2018.01)
*G01N 33/68* (2006.01)
*G01N 33/569* (2006.01)

(52) U.S. Cl.
CPC ..... *C12Q 1/6883* (2013.01); *G01N 33/56911* (2013.01); *G01N 33/6893* (2013.01); *C12Q 2600/118* (2013.01); *C12Q 2600/158* (2013.01); *G01N 2800/26* (2013.01)

(58) Field of Classification Search
None
See application file for complete search history.

(56) References Cited

U.S. PATENT DOCUMENTS

| | | |
|---|---|---|
| 2004/0133352 A1 | 7/2004 | Bevilacqua et al. |
| 2004/0191255 A1 | 9/2004 | Lillard et al. |
| 2004/0191783 A1 | 9/2004 | Leclercq et al. |
| 2004/0241729 A1 | 12/2004 | Liew |
| 2005/0037344 A1 | 2/2005 | Stuhlmuller et al. |

FOREIGN PATENT DOCUMENTS

| | | |
|---|---|---|
| EP | 1 310 567 A2 | 5/2003 |
| WO | 2004/043236 A2 | 5/2004 |
| WO | 2004/087949 A2 | 10/2004 |
| WO | 2004/108957 A2 | 12/2004 |

OTHER PUBLICATIONS

GenBank Accession No. X72501 (NCBI Sep. 9, 1993).
"Affymetrix GeneChip Human Genome U133 Array Set HG-U133A," XP-002254749 GEO, Mar. 11, 2002.
Prucha et al., "Expression Profiling: Toward an Application in Sepsis Diagnostics," Shock, vol. 22, 2004, p. 29-33.
Johnson et al., "Gene Expression Profiles Differentiate Between Sterile SIRS and Early Sepsis," Annals of Surgery, vol. 245, No. 4. Apr. 2007. p. 611-621.
Ramilo et al., "Gene expression patterns in blood leukocytes discriminate patients with acute infections," Blood, vol. 109, No. 5, Mar. 1, 2007, p. 2066-2077.
Pachot et al., "Systemic transcriptional analysis in survivor and non-survivor septic shock patients: A preliminary study," Immunology Letters, vol. 106, 2006, p. 63-71.
Wong et al., "Genome-level expression profiles in pediatric septic shock indicate a role for altered zinc homeostasis in poor outcome," Physiol Genomics, vol. 30, Mar. 20, 2007, p. 146-155.
Shanley et al., "Genome-level longitudinal expression of signaling pathways and gene networks in pediatric septic shock," Mol. Med., 2007.
Calvano et al., "A network-based analysis of systemic inflammation in humans," Nature, vol. 437, Oct. 13, 2005, p. 1032-1037.
Joyce et al. (The journal of Biological Chemistry 2001 vol. 276 p. 11199).
Cabioglu et al. (Arch Surg 2002 vol. 137 p. 1037).
Cheung et al (Nature Genetics, 2003, vol. 33, pp. 422-425).
Cobb et al (Crit Care Med 2002 vol. 30 p. 2711).

*Primary Examiner* — Katherine D Salmon
(74) *Attorney, Agent, or Firm* — Oliff PLC

(57) ABSTRACT

Disclosed herein is a method for the diagnosis/prognosis of a septic syndrome based on a biological sample from a patient. The method may include extracting biological material the biological sample, contacting the biological material with at least one specific reagent that is selected from specific reagents for the target genes having a nucleic acid sequence of any one of SEQ ID NOs: 1 to 28, and determining the expression of at least one of the target genes.

17 Claims, 3 Drawing Sheets

Figure 1:
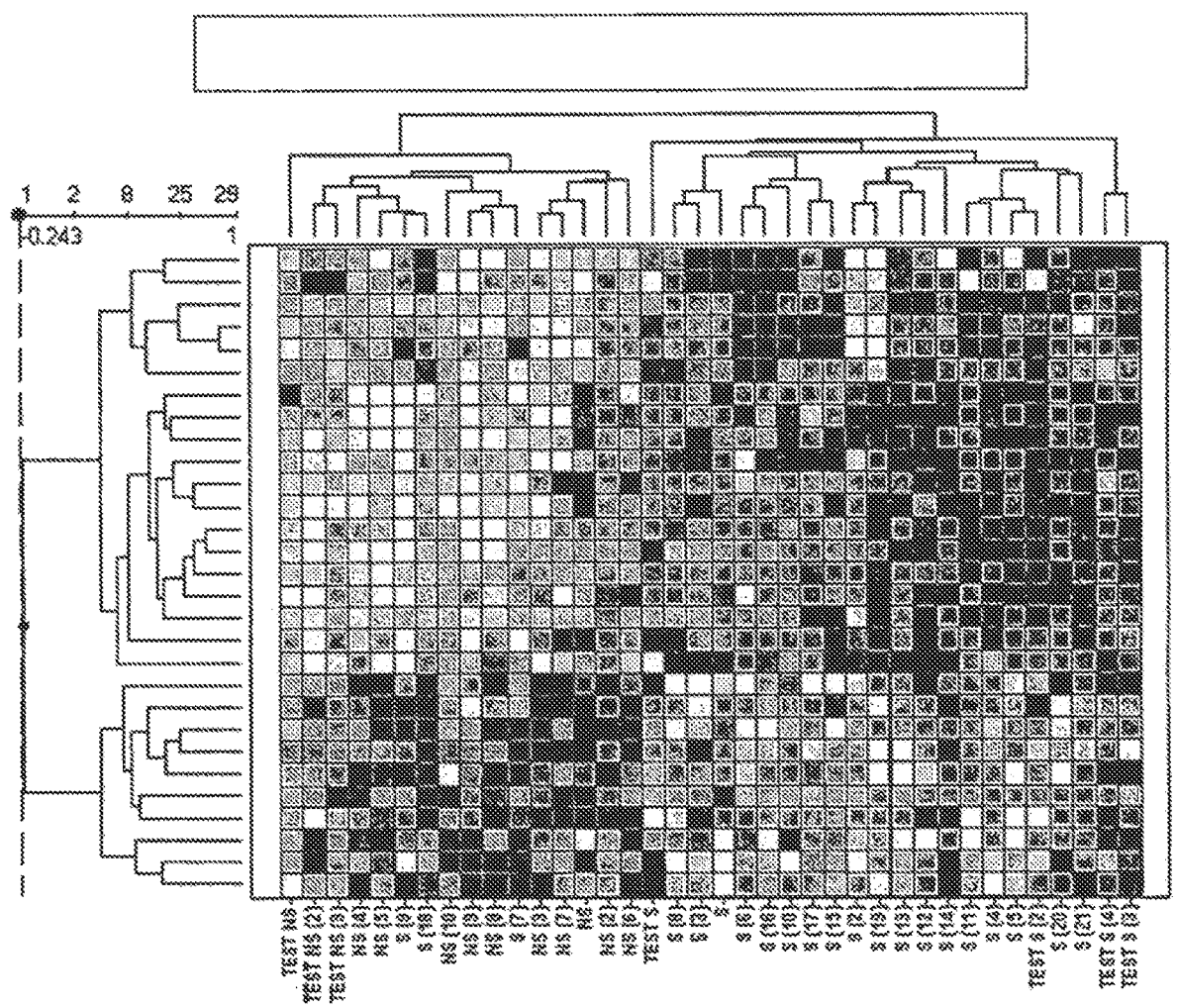

Specification includes a Sequence Listing.

METHOD FOR DIAGNOSIS AND/OR PROGNOSIS OF A SEPTIC SYNDROME

This is a Continuation of application Ser. No. 11/794,690, filed Jul. 3, 2007, which is a National Phase of International Application No. PCT/FR2006/050070 filed Jan. 30, 2006, which in turn claims the benefit of FR 0550267 filed Jan. 31, 2005. The disclosures of the prior applications are hereby incorporated by reference herein in their entireties.

The present invention relates to a method for the diagnosis and/or prognosis of a septic syndrome. The invention also relates to a kit for the diagnosis and/or prognosis of a septic syndrome.

Septic syndrome, a systemic response to infection, represents one of the primary causes of mortality in intensive care units. It can result from a bacterial, viral, fungal or parasitic infection. Among this septic syndrome, the following can be distinguished in increasing order of seriousness: sepsis, severe sepsis and septic shock. In 1992, a group of experts thus proposed criteria for defining these three clinical syndromes (R. C. Bone et al, The ACCP/SCCM Consensus Conference Committee. American College of Chest Physicians/Society of Critical Care Medicine. Chest 101 (6):1644-1655, 1992):

sepsis is thus an inflammatory systemic response related to an infection, severe sepsis is sepsis accompanied by the dysfunction of at least one organ, septic shock is severe sepsis associated with persistent hypotension and can be defined by:
the presence of an identified infectious site,
a generalized inflammatory response that manifests itself by means of at least three of the following signs: a) temperature above 38° C. or below 36° C.; b) heart rate above 90 beats per minute; c) breathing rate above 20 breaths per minute; d) leukocyte count above 12 000/mm$^3$ or below 4000/mm$^3$,
persistent hypotension despite appropriate filling and vasopressive treatments.

In general, the signs of a sepsis, of a severe sepsis and of a septic shock are similar, and the difference between these three situations lies mainly in the degree to which all the vital functions are disturbed. During a septic shock, a drop in arterial pressure, tachycardia, polypnea, blotchy skin, hypothermia or hyperthermia, shivering are principally observed. These signs are also accompanied by a dysfunction of "target" organs, with impairment of the function of organs remote from the infectious site (kidneys, lungs, central nervous system, digestive system and hematological system most commonly affected), reflected by oliguria (<0.5 ml/kg/h), renal insufficiency, hypoxemia, thrombocytopenia, agitation and confusion.

The evolution of a septic syndrome from the stage of sepsis to a stage of severe sepsis, and then of septic shock, is not systematic since approximately 64% of septic patients develop a severe sepsis, and 23% of patients in severe sepsis evolve to septic shock. Before this ultimate step of septic shock, the patient should be prescribed treatments in order to interrupt and reverse the physiopathological process. It is thus necessary to restore a satisfactory hemodynamic state and to ensure effective ventilation. It is also necessary to have in hand the symptomatic treatment of the shock and an antibiotic treatment that, as soon as possible, is appropriate to the bacteriological data.

It thus appears that, while certain patients who develop a septic syndrome, and in particular a septic shock, can be reanimated by means of a relatively simple treatment, such as a treatment with broad-spectrum antibiotics set up before the results of the bacteriological tests that indicate the infectious source, other patients, who develop a much more serious septic syndrome, require a drastic and expensive treatment, such as an injection of activated protein C, for which the cost of the injection is very high. Such treatments are not only expensive, but also expose the patients to risks of very considerable adverse effects (clotting problems, etc.). This treatment should therefore only be proposed to patients with a poor prognosis who absolutely require said treatment.

As a result, the early diagnosis of a septic syndrome is essential and makes it possible to propose a treatment suited to the patient. Furthermore, the prognosis of the septic syndrome, and in particular of a septic shock, is essential in order to provide each patient with a suitable treatment, and to discriminate, as soon as possible, between patients who have a septic syndrome with a poor prognosis, and who require extensive therapy, and patients with a good prognosis. Finally, it is also very advantageous to monitor patients at risk of developing a sepsis, such as patients who have undergone surgery or a transplant, or immunodepressed patients, in order to be able to intervene as early as possible before any major clinical signs.

Currently, the diagnosis and the prognosis of a septic syndrome, and in particular of a septic shock, are essentially based on the number of visceral failures, the response to the symptomatic treatment, and the degree to which the initial infectious site and any possible secondary sites are accessible to medical and/or surgical therapy.

This has the drawback, however, of being applicable only to an advanced stage of septic syndrome, and in particular septic shock, reducing the patient's chances of survival.

The diagnosis and the prognosis of a septic syndrome can also be based on the detection of certain proteins or soluble factors involved in this syndrome. Thus, the assaying of certain cytokines, involved during the development of a septic syndrome, can be a means of diagnosing and of forming a prognosis of a septic syndrome.

Some authors have thus described a positive correlation between the plasma content of IL-1 (interleukin-1) and a septic syndrome with a poor prognosis (Thijs & Hack, Intensive Care Med 31: S258-263, 1995). However, other authors have found no correlation between II-1 and a poor prognosis for septic syndrome, suggesting a great variability of this factor. Furthermore, high dosages of TNF (tumor necrosis factor) have also been associated with a poor prognosis (Casey et al., Ann Intern Med. 1993. 119:771-778). TNF-α then IL-1β are the first two pro-inflammatory cytokines released by monocytes after a septic state has been triggered.

Other authors have shown that the plasma IL-10 (interleukin-10) content is higher in patients developing a sepsis with a poor prognosis, whereas it significantly decreases in patients presenting a sepsis with a good prognosis, and is undetectable in normal patients (Van der Poll, J. Infect. Dis. 175:118-122, 1997). IL-10 is a very important anti-inflammatory cytokine which, by virtue of its ability to inhibit the production of TNF-α and of IL-1β, participates in setting up the state of immunoparalysis. However, since this increase in the IL-10 content is detectable only in 80% of patients in septic shock, the sole detection of this factor remains insufficient for giving a prognosis of the evolution of septic shock.

Mention may also be made of patent U.S. Pat. No. 6,303,321, which describes a method for the prognosis of the severity of a septic syndrome comprising measuring the serum concentration of HMG1 (high mobility group 1 protein) by means of an ELISA-type immunoblotting technique. HMG1 is, unlike TNF-α and IL-1β, described as a late pro-inflammatory mediator of septic syndromes. A high concentration of HMG1 is correlated with a poor prognosis, the serum HMG1 concentration not being detected in normal patients. Post-transcriptional regulation of the HMG1 gene has, on the other hand, been described in the mouse, suggesting that the expression of this gene should be analyzed only at the protein level (Wang et al, Science, 1999, vol 285, p 248-251).

Patent application WO 04/108957 provides a method for the prognosis of a septic syndrome according to which the expression of at least two target genes chosen from: IL-10, TGFβ, HMG1, T-bet, IL-1β, TNFα and GATA-3, is determined. The use of such a panel makes it possible to categorize patients with a good prognosis and patients with a poor prognosis at a rate of more than 80%. It would, however, be necessary to further increase this categorization percentage, in particular as regards the categorization of patients with a poor prognosis, in order to provide them with a drastic treatment as soon as possible.

The present invention proposes to solve the drawbacks of the prior art by providing a novel reliable tool for the diagnosis and/or prognosis of a septic syndrome, such as, in particular, a septic shock.

Surprisingly, the inventors have demonstrated that the analysis of the expression of target genes selected from 28 genes, as presented in table 1 hereinafter, is very relevant for discriminating between patients which a good prognosis and patients with a poor prognosis. The use of such a panel makes it possible in particular to categorize patients with a poor prognosis, at a rate of 100%.

clearly understood that, if various isoforms of these genes exist, all the isoforms are relevant for the present invention, and not only those presented in the above table. In this respect, it should in particular be noted that three variants exist for the target gene of SEQ ID No. 8; only the first variant is presented in the above table, but the second variant, the Genbank accession number of which is NM_153047, and the third variant, the Genbank number of which is NM_153048, are just as relevant for the purpose of the present invention.

Similarly, two variants exist for the target gene of SEQ ID No. 20; only the first variant is presented in the above table, but the second variant, the Genbank accession number of which is NM_032960, is just as relevant for the purpose of the present invention. Similarly, two variants exist for the target gene of SEQ ID No. 22; only the first variant is presented in the above table, but the second variant, the Genbank accession number of which is NM_198926, is just as relevant for the purpose of the present invention. Finally, eleven variants exist for the target gene of SEQ ID No. 25; only the first variant is presented in the above table, but the other variants, the Genbank accession numbers of which are NM_139002; NM_139003; NM_139004; NM_139005; NM_139006; NM_139007; NM_139008; NM_139009; NM_139010; NM_139011, are just as relevant for the purpose of the present invention.

To this effect, the present invention relates to a method for the diagnosis/prognosis of a septic syndrome based on a biological sample from a patient, characterized in that it comprises the following steps:

a. biological material is extracted from the biological sample,

TABLE 1 list of the 28 genes according to the invention

| SEQ ID No. | Gene name | GENBANK No |
|---|---|---|
| 1 | chemokine (C-X3-C motif) receptor 1 | NM_001337 |
| 2 | T cell receptor delta diversity 3 | X72501 |
| 3 | KIAA0882 protein | NM_015130 |
| 4 | T-cell lymphoma invasion and metastasis 1 | NM_003253 |
| 5 | Interleukin 1, beta | NM_000576 |
| 6 | Carbonyl reductase 1 | NM_001757 |
| 7 | TIR domain containing molecule 1 | NM_182919 |
| 8 | FYN tyrosine kinase protooncogene | NM_002037 |
| 9 | Heparanase | NM_006665 |
| 10 | SRY (Sex determining region Y) box 4 | NM_003107 |
| 11 | Interleukin 2 receptor, beta | NM_000878 |
| 12 | Raft-linking protein | NM_015150 |
| 13 | CGI-40 protein Homo sapiens SID 1 transmembrane family, member 2 | NM_015996 |
| 14 | glucose-6-phosphatase catalytic subunit 3 | NM_138387 |
| 15 | Mannosidase alpha, class 1A member 2 | NM_006699 |
| 16 | Myeloid differentiation primary response gene (88) | NM_002468 |
| 17 | Ribosomal protein L6 | NM_000970 |
| 18 | Ribosomal protein L10a | NM_007104 |
| 19 | sin3-associated polypeptide, 30kDa | NM_003864 |
| 20 | Mitogen activated protein kinase-activated protein kinase 2 | NM_004759 |
| 21 | Presenlin enhancer 2 | NM_172341 |
| 22 | Hypothetical protein LOC55924 | NM_019099 |
| 23 | Solute carrier family 39 (zinc transporter member 7) | NM_006979 |
| 24 | Glutathione peroxidase 3 (plasma) | NM_002084 |
| 25 | Hemochromatosis | NM_000410 |
| 26 | Transcriptional activator of the cfos promoter | NM_006365 |
| 27 | peroxisomal biogenesis factor 6 | NM_000287 |
| 28 | Huntingtin interacting protein | NM_005338 |

Several variants sometimes exist for the same target gene. In the present invention, all the variants are relevant. It is b. the biological material is brought into contact with at least one specific reagent that is selected from specific reagents for the target genes with a nucleic sequence having any one of SEQ ID Nos 1 to 28, c. the expression of at least one of said target genes is determined.

For the purpose of the present invention, the term "biological sample" is intended to mean any sample taken from a patient, and liable to contain a biological material as defined hereinafter. This biological sample may in particular be a blood, serum, saliva, tissue or circulating-cell sample from the patient. This biological sample is provided by any type of sampling known to those skilled in the art. According to a preferred embodiment of the invention, the biological sample taken from the patient is a blood sample.

In step a) of the method according to the invention, the biological material is extracted from the biological sample by any of the nucleic acid extraction and purification protocols well known to those skilled in the art. For the purpose of the present invention, the term "biological material" is intended to mean any material that makes it possible to detect the expression of a target gene. The biological material may in particular comprise proteins, or nucleic acids, such as, in particular, deoxyribonucleic acids (DNA) or ribonucleic acids (RNA). The nucleic acid may in particular be an RNA (ribonucleic acid). According to a preferred embodiment of the invention, the biological material extracted in step a) comprises nucleic acids, preferably RNAs, and even more preferably total RNA. Total RNA comprises transfer RNAs, messenger RNAs (mRNAs), such as the mRNAs transcribed from the target gene, but also transcribed from any other gene, and ribosomal RNAs. This biological material comprises material specific for a target gene, such as in particular the mRNAs transcribed from the target gene or the proteins derived from these mRNAs, but can also comprise material not specific for a target gene, such as in particular the mRNAs transcribed from a gene other than the target gene, tRNAs, rRNAs derived from genes other than the target gene.

By way of indication, the nucleic acid extraction can be carried out by:

a step consisting of lysis of the cells present in the biological sample, in order to release the nucleic acids contained in the cells of the patient. By way of example, use may be made of the methods of lysis as described in patent applications:
WO 00/05338 regarding mixed magnetic and mechanical lysis,
WO 99/53304 regarding electrical lysis,
WO 99/15321 regarding mechanical lysis.

Those skilled in the art may use other well-known methods of lysis, such as thermal or osmotic shocks or chemical lyses using chaotropic agents such as guanidinium salts (U.S. Pat. No. 5,234,809);

a purification step, for separating the nucleic acids from the other cellular constituents released in the lysis step. This generally makes it possible to concentrate the nucleic acids, and can be adapted to the purification of DNA or of RNA. By way of example, use may be made of magnetic particles optionally coated with oligonucleotides, by adsorption or covalence (in this respect, see patents U.S. Pat. Nos. 4,672,040 and 5,750,338), and the nucleic acids which are bound to these magnetic particles can thus be purified by means of a washing step. This nucleic acid purification step is particularly advantageous if it is desired to subsequently amplify said nucleic acids. A particularly advantageous embodiment of these magnetic particles is described in patent applications: WO-A-97/45202 and WO-A-99/35500. Another advantageous example of a nucleic acid purification method is the use of silica, either in the form of a column, or in the form of inert particles (Boom R. et al., J. Clin. Microbiol., 1990, n° 28(3), p. 495-503) or magnetic particles (Merck: MagPrep® Silica, Promega: MagneSil™ Paramagnetic particles). Other very widely used methods are based on ion exchange resins in a column or in paramagnetic particulate format (Whatman: DEAE-magarose) (Levison P R et al., J. Chromatography, 1998, p. 337-344). Another method that is very relevant, but not exclusive, for the invention is that of adsorption onto a metal oxide carrier (company Xtrana: Xtra-Bind™ matrix).

When the intention is to specifically extract the DNA from a biological sample, it is possible in particular to carry out an extraction with phenol, chloroform and alcohol in order to remove the proteins, and to precipitate the DNA with 100% ethanol. The DNA can then be pelleted by centrifugation, washed and resolubilized.

When the intention is to subsequently extract the RNAs from a biological sample, it is possible in particular to carry out an extraction with phenol, chloroform and alcohol in order to remove the proteins, and to precipitate the RNAs with 100% ethanol. The RNAs can then be pelleted by centrifugation, washed and resolubilized.

In step b), and for the purposes of the present invention, the term "specific reagent" is intended to mean a reagent which, when it is brought into contact with biological material as defined above, binds with the material specific for said target gene. By way of indication, when the specific reagent and the biological material are of nucleic origin, bringing the specific reagent into contact with the biological material allows the specific reagent to hybridize with the material specific for the target gene. The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracil (U)) bases (this is referred to as an A-T bond) or between the complementary guanine (G) and cytosine (C) bases (this is referred to as a G-C bond). The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base. The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concencentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70° C., in particular between 35 and 65° C. in a saline solution at a concentration of approximately 0.5 to 1 M. A sequence, or nucleotide fragment, or oligonucleotide, or polynucleotide, is a series of nucleotide motifs assembled together by phosphoric ester bonds, characterized by the informational sequence of the natural nucleic acids, capable of hybridizing to a nucleotide fragment, it being possible for the series to contain monomers having different structures and to be obtained from a natural nucleic acid molecule and/or by genetic recombination and/or by chemical synthesis. A motif is a derivative of a monomer which may be a natural nucleotide of nucleic acid, the constitutive elements of which are a sugar, a phosphate group and a nitrogenous base; in DNA, the sugar is deoxy-2-ribose, in RNA, the sugar is ribose; depending on whether DNA or RNA is involved, the nitrogenous base is selected from adenine, guanine, uracil, cytosine and thymine; alternatively the monomer is a nucleotide that is modified in at least one of the three constitutive elements; by way of example, the modification may occur either at the level of the bases, with modified bases such as inosine, methyl-5-deoxycytidine, deoxyuridine, dimethylamino-5-deoxyuridine, diamino-2,6-purine, bromo-5-deoxyuridine or any other modified base capable of hybridization, or at the level of the sugar, for example the replacement of at least one deoxyribose with a polyamide (P. E. Nielsen et al, Science, 254, 1497-1500 (1991)), or else at the level of the phosphate group, for example its replacement with esters in particular selected from diphosphates, alkyl- and arylphosphonates and phosphorothioates.

According to a specific embodiment of the invention, the specific reagent comprises at least one amplification primer. For the purpose of the present invention, the term "amplification primer" is intended to mean a nucleotide fragment comprising from 5 to 100 nucleic motifs, preferably from 15 to 30 nucleic motifs that allow the initiation of an enzymatic polymerization, for instance an enzymatic amplification reaction. The term "enzymatic amplification reaction" is intended to mean a process which generates multiple copies of a nucleotide fragment through the action of at least one enzyme. Such amplification reactions are well known to those skilled in the art and mention may in particular be made of the following techniques:

PCR (polymerase chain reaction), as described in U.S. Pat. Nos. 4,683,195, 4,683,202 and 4,800,159, LCR (ligase chain reaction), disclosed, for example, in patent application EP 0 201 184, RCR (repair chain reaction), described in patent application WO 90/01069, 3 SR (self sustained sequence replication) with patent application WO 90/06995, NASBA (nucleic acid sequence-based amplification) with patent application WO 91/02818, and TMA (transcription mediated amplification) with U.S. Pat. No. 5,399,491.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of messenger RNA derived from the target gene (reference is then made to target-gene-specific cDNA) or a complementary RNA obtained by transcription of the cDNAs specific for a target gene (reference is then made to target-gene-specific cRNA). When the enzymatic amplification is a PCR carried out after a reverse transcription reaction, reference is made to RT-PCR.

According to another preferred embodiment of the invention, the specific reagent of step b) comprises at least one hybridization probe.

The term "hybridization probe" is intended to mean a nucleotide fragment comprising at least 5 nucleotide motifs, such as from 5 to 100 nucleic motifs, in particular from 10 to 35 nucleic motifs, having a hybridization specificity under given conditions so as to form a hybridization complex with the material specific for a target gene. In the present invention, the material specific for the target gene may be a nucleotide sequence included in a messenger RNA derived from the target gene (reference is then made to target-gene-specific mRNA), a nucleotide sequence included in a complementary DNA obtained by reverse transcription of said messenger RNA (reference is then made to target-gene-specific cDNA), or else a nucleotide sequence included in a complementary RNA obtained by transcription of said cDNA as described above (reference will then be made to target-gene-specific cRNA). The hybridization probe may include a label for its detection. The term "detection" is intended to mean either a direct detection by a physical method, or an indirect detection by a method of detection using a label. Many methods of detection exist for detecting nucleic acids [see, for example, Kricka et al., Clinical Chemistry, 1999, n° 45(4), p. 453-458 or Keller G. H. et al., DNA Probes, 2nd Ed., Stockton Press, 1993, sections 5 and 6, p. 173-249]. The term "label" is intended to mean a tracer capable of generating a signal that can be detected. A nonlimiting list of these tracers includes enzymes which produce a signal that can be detected, for example, by colorimetry, fluorescence or luminescence, such as horseradish peroxidase, alkaline phosphatase, beta-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}P$, $^{35}S$ or $^{125}I$.

For the purpose of the present invention, the hybridization probe may be a "detection" probe. In this case, the "detection" probe is labeled by means of a label as defined above. The detection probe may in particular be a "molecular beacon" detection probe as described by Tyagi & Kramer (Nature biotech, 1996, 14:303-308). These "molecular beacons" become fluorescent during the hybridization. They have a stem-loop-type structure and contain a fluorophore and a "quencher" group. The binding of the specific loop sequence with its complementary target nucleic acid sequence causes the stem to unroll and the emission of a fluorescent signal during excitation at the appropriate wavelength.

For the detection of the hybridization reaction, use may be made of target sequences that have been labeled, directly (in particular by the incorporation of a label within the target sequence) or indirectly (in particular using a detection probe as defined above). It is in particular possible to carry out, before the hybridization step, a step consisting in labeling and/or cleaving the target sequence, for example using a labeled deoxy-ribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2 780 059.

According to a preferred embodiment of the invention, the detection probe comprises a fluorophore and a quencher. According to an even more preferred embodiment of the invention, the hybridization probe comprises an FAM (6-carboxy-fluorescein) or ROX (6-carboxy-X-rhodamine) fluorophore at its 5' end and a quencher (Dabsyl) at its 3' end.

The hybridization probe may also be a "capture" probe. In this case, the "capture" probe is immobilized or can be immobilized on a solid substrate by any appropriate means, i.e. directly or indirectly, for example by covalence or adsorption. As solid substrate, use may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions. The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible, for example, to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes. For the purpose of the present invention, the term "medium-density substrate" is intended to mean a substrate comprising from 50 probes to 10 000 probes. For the purpose of the present invention, the term "high-density substrate" is intended to mean a substrate comprising more than 10 000 probes.

The cDNAs or cRNAs specific for a target gene that it is desired to analyze are then hybridized, for example, to specific capture probes. After hybridization, the substrate or chip is washed and the labeled cDNA or cRNA/capture probe complexes are revealed by means of a high-affinity ligand bound, for example, to a fluorochrome-type label. The fluorescence is read, for example, with a scanner and the analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides. Other examples of biochips are given in the publications by G. Ramsay, Nature Biotechnology, 1998, No. 16, p. 40-44; F. Ginot, Human Mutation, 1997, No. 10, p. 1-10; J. Cheng et al, Molecular diagnosis, 1996, No. 1(3), p. 183-200; T. Livache et al, Nucleic Acids Research, 1994, No. 22(15), p. 2915-2921; J. Cheng et al, Nature Biotechnology, 1998, No. 16, p. 541-546 or in U.S. Pat. Nos. 4,981,783, 5,700,637, 5,445,934, 5,744,305 and 5,807,522.

The main characteristic of the solid substrate should be to conserve the hybridization characteristics of the capture probes on the target nucleotide fragments while at the same time generating a minimum background noise for the method of detection.

Three main types of fabrication can be distinguished for immobilizing the probes on the substrate.

First of all, there is a first technique which consists in depositing presynthesized probes. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition):

Printing is an adaptation of the method used by inkjet printers. It is based on the propulsion of very small spheres of fluid (volume <1 nl) at a rate that may reach 4000 drops/second. The printing does not involve any contact between the system releasing the fluid and the surface on which it is deposited.

Microdeposition consists in attaching long probes of a few tens to several hundred bases to the surface of a glass slide. These probes are generally extracted from databases and are in the form of amplified and purified products. This technique makes it possible to produce chips called microarrays that carry approximately ten thousand spots, called recognition zones, of DNA on a surface area of a little less than 4 $cm^2$. The use of nylon membranes, referred to as "macroarrays", which carry products that have been amplified, generally by PCR, with a diameter of 0.5 to 1 mm and the maximum density of which is 25 spots/$cm^2$, should not however be forgotten. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It consists in moving a reaction chamber, in which the oligonucleotide extension reaction takes place, along the glass surface.

Finally, the third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers ($\mu m^2$). This resolution makes it possible to create up to several hundred thousand spots on a surface area of a few square centimeters ($cm^2$). Photolithography has advantages: in bulk in parallel, it makes it possible to create a chip of N-mers in only 4×N cycles. All these techniques can be used with the present invention. According to a preferred embodiment of the invention, the at least one specific reagent of step b) defined above comprises at least one hybridization probe which is preferably immobilized on a substrate. This substrate is preferably a low-, high- or medium-density substrate as defined above.

These hybridization steps on a substrate comprising a multitude of probes may be preceded by an enzymatic amplification reaction step, as defined above, in order to increase the amount of target genetic material.

In step c), the determination of the expression of a target gene can be carried out by any of the protocols known to those skilled in the art.

In general, the expression of a target gene can be analyzed by detecting the mRNAs (messenger RNAs) that are transcribed from the target gene at a given moment or by detecting the proteins derived from these mRNAs.

The invention preferably relates to the determination of the expression of a target gene by detection of the mRNAs derived from this target gene according to any of the protocols well known to those skilled in the art. According to a specific embodiment of the invention, the expression of several target genes is determined simultaneously, by detection of several different mRNAs, each mRNA being derived from a target gene. When the specific reagent comprises at least one amplification primer, it is possible, in step c) of the method according to the invention, to determine the expression of the target gene in the following way:

1) After having extracted, as biological material, the total RNA (comprising the transfer RNAs (tRNAs), the ribosomal RNAs (rRNAs) and the messenger RNAs (mRNAs)) from a biological sample as presented above, a reverse transcription step is carried out in order to obtain the complementary DNAs (or cDNAs) of said mRNAs. By way of indication, this reverse transcription reaction can be carried out using a reverse transcriptase enzyme which makes it possible to obtain, from an RNA fragment, a complementary DNA fragment. The reverse transcriptase enzyme from AMV (Avian Myoblastosis Virus) or from MMLV (Moloney Murine Leukaemia Virus) can in particular be used. When it is more particularly desired to obtain only the cDNAs of the mRNAs, this reverse transcription step is carried out in the presence of nucleotide fragments comprising only thymine bases (polyT), which hybridize by complementarity to the polyA sequence of the mRNAs so as to form a polyT-polyA complex which then serves as a starting point for the reverse transcription reaction carried out by the reverse transcriptase enzyme. cDNAs complementary to the mRNAs derived from a target gene (target-gene-specific cDNA) and cDNAs complementary to the mRNAs derived from genes other than the target gene (cDNAs not specific for the target gene) are then obtained.

2) The amplification primer(s) specific for a target gene is (are) brought into contact with the target-gene-specific cDNAs and the cDNAs not specific for the target gene. The amplification primer(s) specific for a target gene hybridize(s) with the target-gene-specific cDNAs and a predetermined region, of known length, of the cDNAs originating from the mRNAs derived from the target gene is specifically amplified. The cDNAs not specific for the target gene are not amplified, whereas a large amount of target-gene-specific cDNAs is then obtained. For the purpose of the present invention, reference is made, without distinction, to "target-gene-specific cDNAs" or to "cDNAs originating from the mRNAs derived from the target gene". This step can be carried out in particular by means of a PCR-type amplification reaction or by any other amplification technique as defined above. By PCR, it is also possible to simultaneously amplify several different cDNAs, each one being specific for different target genes, by using several pairs of different amplification primers, each one being specific for a target gene: reference is then made to multiplex amplification.

3) The expression of the target gene is determined by detecting and quantifying the target-gene-specific cDNAs obtained in step 2) above. This detection can be carried out after electrophoretic migration of the target-gene-specific cDNAs according to their size. The gel and the medium for the migration can include ethidium bromide so as to allow direct detection of the target-gene-specific cDNAs when the gel is placed, after a given migration period, on a UV (ultraviolet)-ray light table, through the emission of a light signal. The greater the amount of target-gene-specific cDNAs, the brighter this light signal. These electrophoresis techniques are well known to those skilled in the art. The target-gene-specific cDNAs can also be detected and quantified using a quantification range obtained by means of an amplification reaction carried out until saturation. In order to take into account the variability in enzymatic efficiency that may be observed during the various steps (reverse transcription, PCR, etc.), the expression of a target gene of various groups of patients can be normalized by simultaneously determining the expression of a "housekeeping" gene, the expression of which is similar in the various groups of patients. By realizing a ratio of the expression of the target gene to the expression of the housekeeping gene, i.e. by realizing a ratio of the amount of target-gene-specific cDNAs to the amount of housekeeping-gene-specific cDNAs, any variability between the various experiments is thus corrected. Those skilled in the art may refer in particular to the following publications: Bustin S A, *J Mol Endocrinol*, 2002, 29: 23-39; Giulietti *A Methods*, 2001, 25: 386-401.

When the specific reagent comprises at least one hybridization probe, the expression of a target gene can be determined in the following way:

1) After having extracted, as biological material, the total RNA from a biological sample as presented above, a reverse transcription step is carried out as described above in order to obtain cDNAs complementary to the mRNAs derived from a target gene (target-gene-specific cDNA) and cDNAs complementary to the mRNAs derived from genes other than the target gene (cDNA not specific for the target gene).

2) All the cDNAs are brought into contact with a substrate, on which are immobilized capture probes specific for the target gene whose expression it is desired to analyze, in order to carry out a hybridization reaction between the target-gene-specific cDNAs and the capture probes, the cDNAs not specific for the target gene not hybridizing to the capture probes. The hybridization reaction can be carried out on a solid substrate which includes all the materials as indicated above. According to a preferred embodiment, the hybridization probe is immobilized on a substrate. Preferably, the substrate is a low-, high- or medium-density substrate as defined above. The hybridization reaction may be preceded by a step consisting of enzymatic amplification of the target-gene-specific cDNAs as described above, so as to obtain a large amount of target-gene-specific cDNAs and to increase the probability of a target-gene-specific cDNA hybridizing to a capture probe specific for the target gene. The hybridization reaction may also be preceded by a step consisting in labeling and/or cleaving the target-gene-specific cDNAs as described above, for example using a labeled deoxyribonucleotide triphosphate for the amplification reaction. The cleavage can be carried out in particular by the action of imidazole and manganese chloride. The target-gene-specific cDNA can also be labeled after the amplification step, for example by hybridizing a labeled probe according to the sandwich hybridization technique described in document WO-A-91/19812. Other preferred specific methods for labeling and/or cleaving nucleic acids are described in applications WO 99/65926, WO 01/44507, WO 01/44506, WO 02/090584, WO 02/090319.

3) A step consisting of detection of the hybridization reaction is subsequently carried out. The detection can be carried out by bringing the substrate on which the capture probes specific for the target gene are hybridized with the target-gene-specific cDNAs into contact with a "detection" probe labeled with a label, and detecting the signal emitted by the label. When the target-gene-specific cDNA has been labeled beforehand with a label, the signal emitted by the label is detected directly.

When the at least one specific reagent brought into contact in step b) of the method according to the invention comprises at least one hybridization probe, the expression of a target gene can also be determined in the following way:

1) After having extracted, as biological material, the total RNA from a biological sample as presented above, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The cRNAs of the cDNAs of the mRNAs specific for the target gene (reference is then made to target-gene-specific cRNA) and the cRNAs of the cDNAs of the mRNAs not specific for the target gene are then obtained.

2) All the cRNAs are brought into contact with a substrate on which are immobilized capture probes specific for the target gene whose expression it is desired to analyze, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step consisting in labeling and/or cleaving the target-gene-specific cRNAs as described above.

3) A step consisting of detection of the hybridization reaction is subsequently carried out. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

According to a specific embodiment of the invention, steps B and C are carried out at the same time. This preferred method can in particular be carried out by "real time NASBA", which groups together, in a single step, the NASBA amplification technique and real-time detection which uses "molecular beacons". The NASBA reaction takes place in the tube, producing the single-stranded RNA with which the specific "molecular beacons" can simultaneously hybridize to give a fluorescent signal. The formation of the new RNA molecules is measured in real time by continuous verification of the signal in a fluorescent reader. Unlike an RT-PCR amplification, NASBA amplification can take place in the presence of DNA in the sample. It is not therefore necessary to verify that the DNA has indeed been completely eliminated during the RNA extraction.

The analysis of the expression of a target gene selected from any one of SEQ ID Nos 1 to 28 then makes it possible to have a tool for the diagnosis/prognosis of a septic syndrome.

Preferably, the target genes of SEQ ID Nos 1, 2, 4-8, 11 and 16 make it possible to distinguish the two groups of patients.

It is, for example, possible to analyze the expression of a target gene in a patient for whom the prognosis is not known, and to compare with known mean expression values for the target gene in patients with a good prognosis (GP) and known mean expression values for the target gene in patients with a poor prognosis (PP), in order to provide the patient with a suitable treatment.

According to another preferred embodiment, in step b), the biological material is brought into contact with at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 specific reagents that are selected from specific reagents for the target genes with a nucleic sequence having any one of SEQ ID Nos 1 to 28, and, in step c), the expression of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 of said target genes is determined.

More particularly, the inventors have demonstrated that the simultaneous analysis of the expression of a panel of 28 genes as defined above is very relevant for discriminating between GP patients and PP patients. In this respect, the invention also relates to a method as defined above, characterized in that it comprises the following steps:
a. biological material is extracted from the biological sample,
b. the biological material is brought into contact with at least 28 specific reagents that are selected from specific reagents for the target genes with a nucleic sequence having any one of SEQ ID Nos 1 to 28,
c. the expression of at least 28 of said target genes is determined.

The expression of a panel of 22 specific genes, comprising the genes of SEQ ID Nos 1, 3, 7, 9-15, and 17-28, makes it possible, in this respect, to obtain excellent results since it makes it possible to correctly categorize 92% of patients with a good prognosis and 100% of patients with a poor prognosis. In this respect, the invention relates to a method for the diagnosis/prognosis of a septic syndrome based on a biological sample from a patient, characterized in that it comprises the following steps:
a. biological material is extracted from the biological sample,
b. the biological material is brought into contact with at least 22 specific reagents that are selected from specific reagents for the target genes with a nucleic sequence having any one of SEQ ID Nos 1, 3, 7, 9-15 and 17-28,
c. the expression of at least 22 of said target genes is determined.

The use of a restricted panel of genes is particularly suitable for obtaining a prognostic tool. In fact, the analysis of the expression of about 20 genes does not require the custom-made fabrication of DNA chips, and can be carried out directly by PCR or NASBA techniques, or alternatively low-density chip techniques, which provides a considerable economic asset and a simplified implementation.

The invention also relates to a substrate, as defined above, comprising at least 28 hybridization probes selected from probes specific for the target genes with a nucleic sequence having any one of SEQ ID Nos 1 to 28.

According to another embodiment of the invention, the substrate comprises at least 22 hybridization probes selected from probes specific for the target genes with a nucleic sequence having any one of SEQ ID Nos 1, 3, 7, 9-15 and 17-28.

According to another embodiment of the invention, the substrate comprises at least one hybridization probe specific for at least one target gene with a nucleic sequence having any one of SEQ ID Nos 1 to 28, preferably at least one hybridization probe specific for at least one target gene with a nucleic sequence having any one of SEQ ID Nos 1, 2, 4-8, 11 and 16.

Finally, the invention relates to the use of a substrate as defined above, for the diagnosis/prognosis of a septic syndrome.

The invention also relates to the use of at least 28 specific reagents for the target genes with a nucleic sequence having any one of SEQ ID Nos 1 to 28 as defined above, for the diagnosis/prognosis of a septic syndrome. Preferably, the invention relates to the use of at least 22 specific reagents for the target genes with a nucleic sequence having any one of SEQ ID Nos 1, 3, 7, 9-15 and 17-28 as defined above, for the diagnosis/prognosis of a septic syndrome.

The invention also relates to the use of at least one specific reagent for the target genes with a nucleic sequence having any one of SEQ ID Nos 1, 2, 4-8, 11 and 16 as defined above, for the diagnosis/prognosis of a septic syndrome.

Finally, the invention relates to a kit for the diagnosis/prognosis of a septic syndrome, comprising a substrate as defined above.

The invention also relates to a kit for the diagnosis/prognosis of a septic syndrome, comprising at least 28 specific reagents for the target genes with a nucleic sequence having any one of SEQ ID Nos 1 to 28 as defined above, for the diagnosis/prognosis of a septic syndrome. Preferably, the invention relates to a kit for the diagnosis/prognosis of a septic syndrome, comprising at least 22 specific reagents for the target genes with a nucleic sequence having any one of SEQ ID Nos 1, 3, 7, 9-15 and 17-28 as defined above, for the diagnosis/prognosis of a septic syndrome.

The invention also relates to a kit for the diagnosis/prognosis of a septic syndrome, comprising at least one specific reagent for the target genes with a nucleic sequence having any one of SEQ ID Nos 1, 2, 4-8, 11 and 16 as defined above, for the diagnosis/prognosis of a septic syndrome.

Of course, all the definitions indicated above in the description apply for all the embodiments of the invention.

The attached figures are given by way of explanatory example and are in no way limiting in nature. It will make it possible to understand the invention more completely.

FIG. 1 represents an analysis of hierarchical clustering of 38 blood samples obtained from 13 PP patients (also called NS) and 26 GP patients (also called S), using the expression of 28 genes according to the invention, measured with 29 probe sets on the Affymetrix biochip. The hierarchical clustering function of the Spofire software organizes the PP and GP patients in columns, and the genes in rows so as to obtain in adjacent positions the patients or the genes with comparable expression profiles. Pearson's correlation coefficient was used as a similarity index for the genes and the patients. Subsequently, firstly the unweighted pair group method using arithmetic averages, UPGMA, clustering method and, secondly, the mean value of all the samples made it possible to organize the patients and the genes, respectively. The results correspond to the Affymetrix fluorescence level normalized with the «Affy» software. In order to take into account the constitutive differences in expression between the genes, the levels of expression of each gene were normalized by applying a reduced centered normal law. The white represents the low levels of expression, the gray the intermediate levels and the black the high levels. The height of the branches of the dendogram indicates the index of similarity between the expression profiles.

Figure 2:
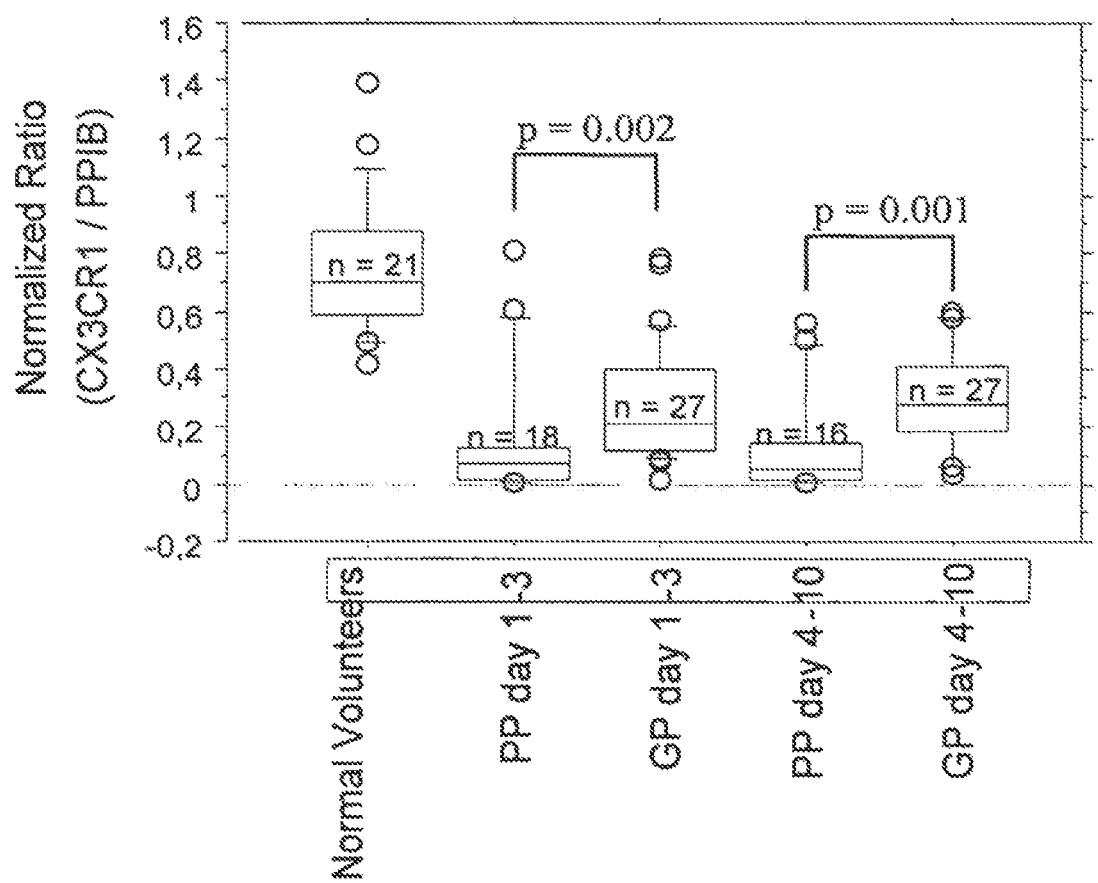

FIG. 2 presents the quantification of CX3CR1 mRNA in the blood of patients in septic shock. The gene expression level was measured by quantitative RT-PCR in 50 patients in septic shock (19 PP and 21 GP) and 21 normal volunteers. The results were normalized to the level of expression of the PPIB housekeeping gene. The results are presented with the median, the 25th percentile and the 75th percentile. Statistical comparison between the GP and PP was carried out by virtue of the nonparametric Mann-Whitney test.

Figure 3:
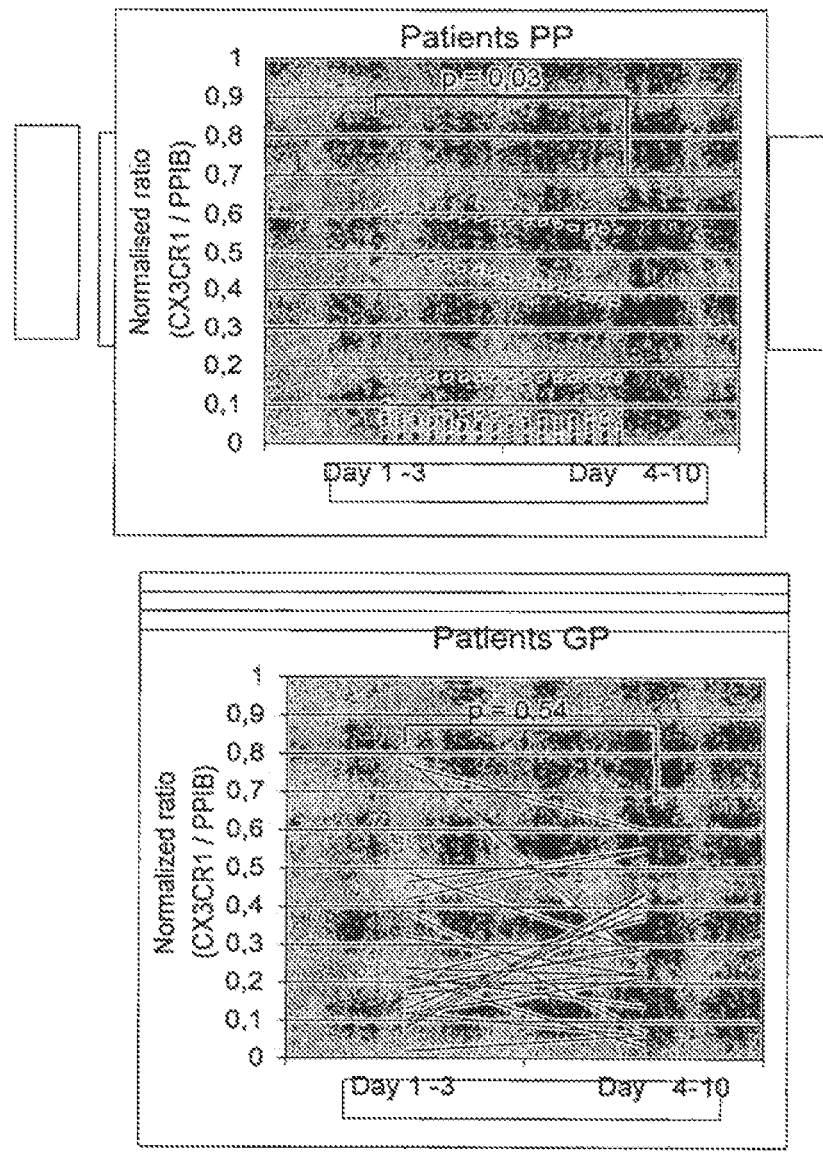

FIG. 3 presents the quantification of CX3CR1 mRNAs quantified in the blood of patients in septic shock. The gene expression level was measured by quantitative RT-PCR in 37 patients in septic shock (12 PP and 21 GP). For each patient, a PAXgene sample was obtained between D1 and D3 and another between D4 and D10. The results were normalized to the level of expression of the PPIB housekeeping gene. The evolution of the gene expression level of CX3CR1 between D1-D3 and D4-D10 in the PP and GP was performed by virtue of the nonparameteric Wilcoxon test.

The following examples are given by way of illustration and are in no way limiting in nature. They will make it possible to understand the invention more fully.

Example 1: Search for an Expression Profile for the Diagnosis/Prognosis of a Septic Syndrome Characteristics of the biological samples: The study was carried out on patients having developed a septic syndrome, and admitted into the surgical or medical intensive care unit of the Lyon-Sud hospital center. In order to be included in the study, the patients had to present the following criteria: over 18 years of age; presence of a septic shock according to the consensus conference previously described; absence of comorbidity (metastatic cancer, malignant hemopathy, type I diabetes, chronic hepatic pathology, chronic renal insufficiency, AIDS). Since the objective of the study was to study the late mortality induced by a septic shock, the patients who died over the first 48 hours of the syndrome were excluded from the study. The treatment for all the patients included was similar.

Taking the day of the first administration of catecholamine to be D1 of the septic shock, each patient was monitored for a maximum period of 28 days. On the basis of the mortality observed over this period, a group of 10 patients (PP) and a group of 21 patients (GP) were studied. Subsequently, the gene panel according to the invention was validated blind using two groups of patients recruited on the basis of the same criteria: one group of 3 PP patients and one group of 4 GP patients. The genomic analyses were carried out using samples obtained between D2 and D4. The demographic characteristics of the entire cohort are presented in the following table:

Extraction of the Biological Material (Total RNA) from the Biological Sample:

The samples were collected directly in PAXGene™ Blood RNA tubes (PreAnalytix, Frankin Lakes, USA). After the step consisting in taking the blood sample and in order to obtain total lysis of the cells, the tubes were left at ambient temperature for 4 h and then stored at −20° C. until the extraction of the biological material. More specifically, in this protocol, the total RNA was extracted using the PAXGene Blood RNA® kits (PreAnalytix) while observing the manufacturer's recommendations. Briefly, the tubes were centrifuged (10 min, 3000 g) in order to obtain a pellet of nucleic acid. This pellet was washed and taken up in a buffer containing proteinase K required for digestion of the proteins (10 min at 55° C.). A further centrifugation (5 min, 19 000 g) was carried out in order to remove the cell debris, and ethanol was added in order to optimize the nucleic acid binding conditions. The total RNA was specifically bound to PAXGene RNA spin columns and, before elution of the latter, a digestion of the contaminating DNA was carried out using the RNAse-free DNAse set (Qiagen Ltd, Crawley, UK). The quality of the total RNA was analyzed with the AGILENT 2100 bioanalyzer (Agilent Technologies, Waldbronn, Germany). The total RNA comprises the transfer RNAs, the messenger RNAs (mRNAs) and the ribosomal RNAs.

Synthesis of cDNA, obtaining of cRNAs, labeling of cRNAs and quantification: In order to analyze the expression of the target genes according to the invention, the complementary DNAs (cDNAs) of the mRNAs contained in the total RNA as purified above were obtained from 5 μg of total RNA, using 400 units of the SuperScriptII reverse transcription enzyme (Invitrogen) and 100 pmol of poly-T primer containing the T7 promoter (T7-oligo(dT)24-primer, Proligo, Paris, France). The cDNAs thus obtained were then extracted with phenol/chloroform and precipitated with ammonium acetate and ethanol and redissolved in 24 μl of

|  |  | GP | | PP | | | |
|---|---|---|---|---|---|---|---|
|  |  | Train n = 21 (%) | Test n = 4 (%) | Train n = 10 (%) | Test n=3 (%) | Total n = 38 (%) | P[a] |
| | Men | 13 (62) | 2 (50) | 7 (70) | 1 (33) | 23 (61) | 0.930 |
| | Women | 8 (38) | 2 (50) | 3 (30) | 2 (67) | 15 (39) | |
| | Age (years)[b] | 67 (49-71) | 71 (66-75) | 68 (57-79) | 78 (63-80) | 67 (54-78) | 0.371 |
| | SAPS II at admission[b] | 48 (40-55) | 45 (37-52) | 61 (59-73) | 61 (60-72) | 55 (42-61) | <0.001 |
| | Duration of hospitalization in ICU.[b] | 12 (10-26) | 32 (28-34) | 9 (8-14) | 4 (4-10) | 12 (9-25) | 0.013 |
| | COPD | 1 (5) | 2 (50) | 3 (30) | 1 (33) | 7 (18) | 0.203 |
| MacCabe and Jackson criteria | 0 | 7 (33) | 1 (25) | 0 | 0 | 8 (21) | 0.045 |
| | 1 | 9 (43) | 2 (50) | 9 (90) | 1 (33) | 21 (55) | |
| | 2 | 5 (24) | 1 (25) | 0 | 2 (67) | 8 (21) | |
| | 3 | 0 | 0 | 1 (10) | 0 | 1 (3) | |
| | Microbiologically documented diagnosis | 15 (71) | 4 (100) | 7 (70) | 3 (100) | 29 (76) | >0.999 |
| | In Gram(−) Bacillus | 8 (38) | 1 (25) | 3 (30) | 3 (100) | 15 (39) | 0.950 |
| | In Gram(+) Cocci | 7 (33) | 1 (25) | 5 (50) | 1 (33) | 14 (37) | |
| | Fungal | 6 (29) | 1 (25) | 3 (30) | 1 (33) | 11 (29) | |
| Type of infection | Community-acquired | 7 (33) | 4 (100) | 5 (50) | 1 (33) | 17 (45) | 0.900 |
| | Hospital-acquired | 14 (67) | 0 (0) | 5 (50) | 2 (67) | 21 (55) | |
| Site of the infection | Pulmonary | 6 (29) | 2 (50) | 8 (80) | 1 (33) | 17 (45) | 0.061 |
| | Abdominal | 12 (57) | 1 (25) | 2 (20) | 2 (67) | 17 (45) | |
| | Others | 3 (14) | 1 (25) | 0 (0) | 0 (0) | 4 (11) | |

[a]comparison between the overall population of survivors (n = 25) and non-survivors (n = 13)
[b]Median (Q1-Q3)
COPD: chronic obstructive pulmonary disease DEPC water. A 20 μl volume of this purified solution of cDNA was subsequently subjected to in vitro transcription using a T7 RNA polymerase which specifically recognizes the promoter of the T7 polymerase as mentioned above. This transcription makes it possible to obtain the cRNA of the cDNA. This transcription was carried out using a Bioarray High Yield RNA Transcript Labeling Kit (Enzo Diagnostics, Farmingdale, NY), which not only makes it possible to obtain the cRNA, but also allows the incorporation of biotinylated cytidine and uridine bases during the synthesis of the cRNA.

The purified cRNAs were subsequently quantified by spectrophotometry, and the cRNA solution was adjusted to a concentration of 1 μg/μl of cRNA. The step consisting of cleavage of these cRNAs was subsequently carried out at 94° C. for 35 min, using a fragmentation buffer (40 mM of tris acetate, pH 8.1, 100 mM of potassium acetate, 30 mM of magnesium acetate) in order to bring about the hydrolysis of the cRNAs and to obtain fragments of 35 to 200 bp. The success of such a fragmentation was verified by 1.5% agarose gel electrophoresis.

Demonstration of a differential expression profile between the PP and GP patients: For this, 20 μg of fragmented cRNAs derived from each sample were added to a hybridization buffer (Affymetrix) and 200 μl of this solution were brought into contact for 16 h at 45° C. on an expression chip (Human Genome U133A GeneChip® (Affymetrix)), which comprises 22 283 groups of probes representing approximately 14 500 genes according to the Affymetrix protocol as described on the Affymetrix internet site. In order to record the best hybridization and washing performance levels, RNAs described as "control" RNAs, that were biotinylated (bioB, bioC, bioD and cre), and oligonucleotides (oligo B2) were also included in the hybridization buffer. After the hybridization step, the solution of cRNA biotinylated and hybridized on the chip was visualized using a solution of streptavidin-phycoerythrin and the signal was amplified using an anti-streptavidin antibody. The hybridization was carried out in a "GeneChip hybridization oven" (Affymetrix), and the Euk GE-WS2V4 protocol of the Affymetrix protocol was followed. The washing and visualization steps were carried out on a "Fluidics Station 450" (Affymetrix). Each U133A chip was subsequently analyzed on an Agilent G2500A GeneArray Scanner at a resolution of 3 microns in order to pinpoint the areas hybridized on the chip. This scanner makes it possible to detect the signal emitted by the fluorescent molecules after excitation with an argon laser using the epifluorescence microscope technique. A signal proportional to the amount of cRNAs bound is thus obtained for each position. The signal was subsequently analyzed using the Microarray Suite 5.0 software (MAS5.0, Affymetrix). In order to prevent the variations obtained by using various chips, an overall normalization approach was carried out using the MAS5.0 software (Affymetrix), which, by virtue of a statistical algorithm, makes it possible to define whether or not a gene was expressed. In order to be able to compare the chips with one another, the raw data (".CELL" file) were processed by means of a quantile normalization step using the "Affy" package of the "R" software (Gautier, L. et al., Bioinformatics (2004), p. 30'7-315). Each gene represented on the U133A chip was covered by 11 pairs of probes of oligonucleotides. The term "pair of probes" is intended to mean a first probe which hybridized perfectly (reference is then made to PM or perfect match probes) with one of the cRNAs derived from a target gene, and a second probe, identical to the first probe with the exception of a mismatch (reference is then made to MM or mismatched probe) at the center of the probe. Each MM probe was used to estimate the background noise corresponding to a hybridization between two nucleotide fragments of non-complementary sequence (Affymetrix technical note "Statistical Algorithms Reference Guide"; Lipshutz, et al (1999) Nat. Genet. 1 Suppl., 20-24). The 38 samples of the study showed an average of 38.1±4.2% of expressed genes.

The analysis of the expression data was carried out using the Microsoft Excel software, the Spotfire decision site for functional genomics V7.1 software (Spotfire AB, Gothenburg, Sweden), and a statistical algorithm: the genetic algorithm (Gautier, L. et al., Bioinformatics (2004), p. 30'7-315; Ooi, C. H. and Tan, P. Bioinformatics (2003), p. 3'7-44). Based on the 22 283 groups of probes, representing approximately 14 500 genes, of the chip, the inventors duly selected the relevant genes that made it possible to differentiate between the PP patients and the GP patients.

For this, a first step consisted in excluding the genes exhibiting a level of expression comparable between all the groups of patients. Four steps were carried out:

the genes not expressed in all the patients were excluded (MAS5.0 software).

the genes for which the fluorescence median was less than 30 in the two groups were excluded;

the genes that were not expressed in at least 30% of the patients in one of the two groups were excluded;

the genes for which the ratio of the expression medians between the GP and PP patients was between 0.77 and 1.3 were excluded.

Subsequent to the application of these filters, a group of 2216 groups of probes was selected and was used as a working base for a multiparametric analysis with the Genetic Algorithm.

Results obtained: a list of 28 genes was identified. The increase or the decrease in expression of each of these genes, observed in the PP patients compared with the BP patients, is indicated in table 2.

TABLE 2

List of 28 genes differentially expressed in PP and GP patients

| SEQ ID N° | Gene name | Abbreviated name | Expression in PP versus GP |
|---|---|---|---|
| 1 | chemokine (C-X3-C motif) receptor 1 | CX3CR1 | Increased* |
| 2 | T cell receptor delta diversity 3 | TRDD3 | Increased£ |
| 3 | KIAA0882 protein | KIAA0882 | Increased |
| 4 | T-cell lymphoma invasion and metastasis 1 | TIAM1 | Increased£ |
| 5 | Interleukin 1, beta | IL1B | Increased* |
| 6 | Carbonyl reductase 1 | CBR1 | Increased£ |
| 7 | TIR domain containing molecule 1 | TRIF | Increased* |
| 8 | FYN tyrosine kinase protooncogene | FYN | Increased£ |

TABLE 2-continued

List of 28 genes differentially expressed in PP and GP patients

| SEQ ID N° | Gene name | Abbreviated name | Expression in PP versus GP |
|---|---|---|---|
| 9 | Heparanase | HPSE | Increased |
| 10 | SRY (Sex determining region Y) box 4 | SOX4 | Increased£ |
| 11 | Interleukin 2 receptor, beta | IL2RB | Increased* |
| 12 | Raft-linking protein | RAFTLIN | Increased |
| 13 | CGI-40 protein Homo sapiens SID1 transmembrane family, member 2 | CGI-40 SIDT2 | Increased |
| 14 | glucose-6-phosphatase catalytic subunit 3 | G6PC3 | Increased |
| 15 | Mannosidase alpha, class 1A member 2 | MAN1A2 | Increased |
| 16 | Myeloid differentiation primary response gene (88) | MYD88 | Increased* |
| 17 | Ribosomal protein L6 | RPL6 | Increased |
| 18 | Ribosomal protein L10a | RPL10a | Increased |
| 19 | sin3-associated polypeptide, 30kDa | SAP30 | Decreased |
| 20 | Mitogen activated protein kinase-activated protein kinase 2 | MAPKAPK2 | Decreased |
| 21 | Presenlin enhancer 2 | PEN2 | Decreased |
| 22 | Hypothetical protein LOC55924 | LOC55924 | Decreased |
| 23 | Solute carrier family 39 (zinc transporter member 7) | SLC39A7 | Decreased£ |
| 24 | Glutathione peroxidase 3 (plasma) | GPX3 | Decreased£ |
| 25 | Hemochromatosis | HFE | Decreased |
| 26 | Transcriptional activator of the cfos promoter | CROC4 | Decreased |
| 27 | peroxisomal biogenesis factor 6 | PEX6 | Decreased |
| 28 | Huntingtin interacting protein | | Decreased |

The indication of an * and £ indicate respectively a statistically different difference between the two groups according to a T test with Bonferroni or Benjamini and Hochberg correction, respectively. This indicates that these genes taken in isolation are very relevant in the diagnosis/prognosis of a septic syndrome.

Validation by Quantitative RT-PCR

In order to confirm these results by means of another molecular biology technique, certain genes were assayed by quantitative RT-PCR. Briefly, a reverse transcription (RT) reaction was carried out in a final volume of 20 µl. The total RNA (1 µg) was mixed with 1 µl of polyT at 50 µM and 1 µl of dNTP mix (ThermoScript™ RT-PCR system, Invitrogen), and then incubated for 5 min at 65° C. After cooling in ice, the solution was mixed with 4 µl of 5×cDNA synthesis buffer, 1 µl of RNAse out (40 U/µl), 1 µl of DEPC-treated water and 1 µl of Thermoscript RT (15 U/µl), all these products being derived from the ThermoScript™ RT-PCR system (Invitrogen). The reverse transcription was carried out for 1 h at 50° C. and then stopped by incubation at 85° C. for 5 min. To finish, each cDNA solution was diluted to 1/10 in DEPC water. For each of the genes of interest, a standard was prepared by means of a PCR (polymerase chain reaction) amplification carried out until saturation. The amplicons obtained were purified (PCR purification kit, Qiagen Ltd) and the presence of a unique amplicon was verified by agarose gel electrophoresis and ethidium bromide staining. The standard consisting of the peptidylpropyl isomerase B (PPIB) «housekeeping» gene encoding cycophilin B was obtained from Search-LC (Heidelberg, Germany).

Analysis of mRNA Expression by Real Time PCR

The mRNAs of the target genes of SEQ ID Nos 1, 5, 11 and 16 were quantified by real time quantitative PCR using the LightCycler™ (Roche). The PCR reactions were carried out using the Fast-Start™ DNA Master SYBR Green I real-time PCR kit (Roche Molecular Biochemicals). Each PCR was carried out in a final volume of 20 µl containing 1 µl of LC-Fast Start Reaction Mix SYBR Green I, 1 µl of LC-Fast Start DNA Master SYBR Green I/Enzyme (including the Taq DNA polymerase, the reaction buffer and a deoxynucleotide triphosphate mix), $MgCl_2$ (final concentration of 3 mM), the sense and antisense primers (final concentration of 0.5 µM), and 10 µl of cDNA solution. After a denaturation step of 10 min at 95° C., the amplification was carried out by means of 40 cycles of a "touch-down" PCR protocol (10 s at 95° C., 10 s of hybridization at 68-58° C., followed by an extension of 16 s at 72° C.). At the end of each cycle, the fluorescence emitted by the SYBR Green was measured.

In order to confirm the specificity of the amplification, the PCR products were systematically subjected to a melting curve analysis (LightCycler™—Roche). For this, the PCR products were treated with an increase in temperature of from 58 to 98° C., with an increase of 0.1° C./s. For each PCR product, a single peak was obtained in the analysis of the curve, characterized by a specific melting point.

The combinations of primers required for the quantification of the PPIB housekeeping gene and IL-1β gene (SEQ ID No. 5) were obtained from Search-LC (Heidelberg, Germany). For PPIB, the Genbank accession no. was M60857 and the 105-338 region was amplified. For IL-113, the Genbank accession no. was M15330 and the 438-642 region was amplified. The pairs of primers used to quantitatively determine the target genes of SEQ ID Nos 1, 11 and 16, the Genbank sequence used as reference and the position of the amplicons are described in the table below.

| TARGET GENE OF SEQ ID No. | | | | amplicon |
|---|---|---|---|---|
| 1 | Sense primer 5'-->3' | SEQ ID No. 29 | TGACTGGCAGATCCAGAGGTT | 164 bases |
| | Antisense primer 5'-->3 | SEQ ID No. 30 | GTAGAATATGGACAGGAACAC | |

| TARGET GENE OF SEQ ID No. | | | amplicon |
|---|---|---|---|
| 11 | Sense primer 5'-->3'<br>Antisense primer 5'-->3 | SEQ ID No. 31 CCTGAAGTGTAACACCCCAGA<br>SEQ ID No. 32 TCCCTCTCCAGCACTTCTAGT | 162 bases |
| 16 | Sense primer 5'-->3'<br>Antisense primer 5'-->3 | SEQ ID No. 33 TGCTGGAGCTGGGACCCAGCATTGAGGAGGA<br>SEQ ID No. 34 TCAGACACACACAACTTCAGTCGATAG | 280 bases |

The amount of target mRNA relative to the amount of mRNA of the PPIB housekeeping gene was analyzed by the relative quantification technique with the LightCycler Relative Quantification Software (Roche Molecular Biochemicals). The "Second Derivative Maximum Method" of the LightCycler™ (Roche) was used to automatically determine the crossing point (Cp) for each sample. The value of the Cp was defined as the number of cycles for which the fluorescence was significantly different than the background noise.

Five serial 10-fold dilutions were carried out in quadruplicate with each standard in order to generate a standard curve expressing the Cp as a function of the logarithm of the number of copies. The standard dilutions were optimized so that the standard curve covered the expected level of expression for the target gene and the housekeeping gene. The relative standard curves describing the PCR efficiency for the target gene and the housekeeping gene were generated and used to perform a quantification with the LightCycler Relative Quantification Software (Roche Molecular Biochemicals).

The results obtained for the quantitative determination of the mRNAs of the target genes of SEQ ID Nos 1, 5, 11 and 16 by quantitative RT-PCR are given in table 3 below. The results correspond to 25 samples (8 PP and 17 GP). The correlation of the results obtained, firstly, with the biochip and, secondly, with the quantitative RT-PCR technique was established by means of Spearman's correlation test.

TABLE 3

Comparison of the levels of expression of 4 genes between Affymetrix and quantitative RT-PCR

| Abbreviated gene name | median Affymetrix GP | median Affymetrix PP | median RT-PCR GP | median RT-PCR PP | Spearman correlation coefficient: r | Spearman test degree of significance: p |
|---|---|---|---|---|---|---|
| CX3CR1 | 582.965 | 92.995 | 0.04295 | 0.00663 | 0.94 | <0.001 |
| IL-1B | 227.64 | 113.4 | 0.329 | 0.18 | 0.83 | <0.001 |
| IL-2RB | 204.86 | 131.965 | 0.00075 | 0.00024 | 0.76 | <0.001 |
| MyD88 | 2644.03 | 1986.315 | 0.0351 | 0.0294 | 0.56 | <0.01 |

For the 4 genes analyzed, a significant correlation was observed between the Affymetrix results and the quantitative RT-PCR results, confirming the relevance of the genes according to the invention.

By following the same protocol as that described in the above paragraphs, the CX3CR1 mRNAs were quantified from blood samples taken from 50 patients in septic shock (19 PP and 21 GP). A blood sample was obtained during the first 72 hours after the beginning of the shock, and then a second sample was obtained later on in the course of the syndrome. The level of expression of CX3CR1 was normalized to that of the PPIB housekeeping gene. The results are given in FIG. 2. The comparison between GP and PP was carried out using the nonparametric Mann-Whitney test. It is therefore particularly advantageous to analyze the expression of CX3CR1 mRNA as a poor prognosis factor.

The level of expression of the CX3CR1 mRNA showed a significant decrease over time in the PP patients. The results are given in FIG. 3. The evolution of the expression over time was tested using the Wilcoxon test.

It is therefore particularly advantageous to follow the expression of the CX3CR1 mRNA over time in order to confirm this poor prognosis.

Analysis of the Expression of a Panel of Genes

The inventors also demonstrated that the simultaneous analysis of the expression of several genes was very relevant for discriminating between GP and PP patients.

The inventors thus demonstrated that the simultaneous analysis of the expression of the 28 genes described above was very relevant for discriminating between the two GP and PP groups.

The results are given in FIG. 1. This list made it possible to clusterize 88% of the samples from GP patients in one group and 100% of the samples from PP patients in another group.

In addition, the inventors demonstrated that the simultaneous analysis of the expression of the genes of SEQ ID Nos 1, 3, 7, 9-15 and 17-28, among the 28 described above, was also particularly relevant for discriminating between the two GP and PP groups. The results are given in FIG. 2. This list made it possible to clusterize 92% of the samples from GP patients in one group and 100% of the samples from PP patients in another group.

Among the 28 genes described above, each of the 9 genes of SEQ ID Nos 1, 2, 4-8, 11 and 16 makes it possible to discriminate between the two groups of patients. Table 4 represents the p value calculated using the T tet with Bonferroni or Benjamini and Hochberg correction. All these genes were overexpressed in the GP compared with the PP.

TABLE 4

Genes for discriminating between the two groups of patients.

| Gene name | Gene Symbol | Bonferroni correction | BHFDR correction | Fold change |
|---|---|---|---|---|
| Chemokine (C-X3-C motif) receptor 1 | CX3CR1 | 6.3E−05 | 6.3E−05 | 8.33 |
| T cell receptor delta diversity 3 | TRDD3 | >0.05 | 4.4E−02 | 4.00 |
| T-cell lymphoma invasion and metastasis 1 | TIAM1 | >0.05 | 2.7E−02 | 2.08 |
| Interleukin 1, beta | IL1B | 4.9E−02 | 9.7E−03 | 2.08 |
| Carbonyl reductase 1 | CBR1 | >0.05 | 2.8E−02 | 1.89 |
| TIR domain containing adaptor inducing interferon-beta | TRIF | 5.3E−04 | 2.6E−04 | 1.72 |
| FYN tyrosine kinase protooncogene | FYN | >0.05 | 2.7E−02 | 1.67 |
| Interleukin 2 receptor, beta | IL2RB | 4.3E−02 | 9.7E−03 | 1.52 |
| Myeloid differentiation primary response gene (88) | MYD88 | 3.5E−02 | 9.7E−03 | 1.37 |

What is claimed is:

1. A method comprising:
obtaining a blood sample from a patient having a septic syndrome; and
measuring expression levels of one or more target genes in the blood sample using at least one specific reagent, including measuring overexpression of SEQ ID NO: 1 relative to a reference value in the blood sample;
wherein no more than 10,000 specific reagents are used to measure the expression levels of the one or more target genes in the blood sample.

2. The method according to claim 1, further comprising extracting biological material from the blood sample.

3. The method according to claim 2, wherein the overexpression is measured by contacting the biological material with a reagent specific for an expression product of SEQ ID NO: 1.

4. The method according to claim 3, further comprising detecting hybridization of the specific reagent to the expression product.

5. The method according to claim 3, wherein the specific reagent comprises a hybridization probe.

6. The method according to claim 5, wherein the hybridization probe is immobilized on a substrate.

7. The method according to claim 2, wherein the biological material comprises nucleic acids.

8. The method according to claim 1, further comprising measuring expression levels of target genes respectively comprising the nucleic acid sequences of SEQ ID NOs: 3, 7, 9-15, and 17-28 in the blood sample.

9. The method according to claim 8, wherein the expression levels of 22 target genes in the blood sample are measured.

10. The method according to claim 1, wherein the expression levels of 28 target genes in the blood sample are measured.

11. The method according to claim 1, further comprising measuring expression levels of target genes respectively comprising the nucleic acid sequences of SEQ ID NOs: 2, 4-8, 11, and 16 in the blood sample.

12. The method according to claim 1, further comprising measuring expression levels of target genes respectively comprising the nucleic acid sequences of SEQ ID NOs: 2-28 in the blood sample.

13. The method according to claim 1, wherein no more than 50 specific reagents are used to measure expression levels of the one or more target genes in the blood sample.

14. The method according to claim 1, further comprising monitoring the expression level of SEQ ID NO: 1 over time.

15. The method according to claim 1, wherein the reference value is a predetermined value indicative of a poor prognosis for septic syndrome.

16. The method according to claim 1, further comprising treating the patient with an antibiotic and/or activated protein C.

17. The method according to claim 1, wherein the overexpression is measured via an amplification method comprising the use of a first primer consisting of SEQ ID NO: 29 and a second primer consisting of SEQ ID NO: 30.

* * * * *

SEQUENCE LISTING

<160> NUMBER OF SEQ ID NOS: 34

<210> SEQ ID NO 1
<211> LENGTH: 3100
<212> TYPE: DNA
<213> ORGANISM: Homo sapiens

<400> SEQUENCE: 1

```
actcgtctct ggtaaagtct gagcaggaca gggtggctga ctggcagatc cagaggttcc      60
cttggcagtc cacgccaggc cttcaccatg gatcagttcc ctgaatcagt gacagaaaac     120
tttgagtacg atgatttggc tgaggcctgt tatattgggg acatcgtggt ctttgggact     180
gtgttcctgt ccatattcta ctccgtcatc tttgccattg gctggtggg aaatttgttg     240 gtagtgtttg ccctcaccaa cagcaagaag cccaagagtg tcaccgacat ttacctcctg     300
aacctggcct tgtctgatct gctgtttgta gccactttgc ccttctggac tcactatttg     360
ataaatgaaa agggcctcca caatgccatg tgcaaattca ctaccgcctt cttcttcatc     420
ggcttttttg aagcatatt cttcatcacc gtcatcagca ttgataggta cctggccatc     480
gtcctggccg ccaactccat gaacaaccgg accgtgcagc atgcgtcac catcagccta     540 ggcgtctggg cagcagccat tttggtggca gcaccccagt tcatgttcac aaagcagaaa     600
gaaaatgaat gccttggtga ctaccccgag gtcctccagg aaatctggcc cgtgctccgc     660 aatgtgaaa caattttct tggcttccta ctcccctgc tcattatgag ttattgctac     720
ttcagaatca tccagacgct gttttcctgc aagaaccaca gaaagccaa agccattaaa     780 ctgatccttc tggtggtcat cgtgttttc ctcttctgga cccctacaa cgttatgatt     840 ttcctggaga cgcttaagct ctatgacttc tttcccagtt gtgacatgag gaaggatctg     900
aggctggccc tcagtgtgac tgagacggtt gcatttagcc attgttgcct gaatcctctc     960
atctatgcat ttgctgggga aagttcaga agatacctt accacctgta tgggaaatgc    1020
ctggctgtcc tgtgtgggcg ctcagtccac gttgatttct cctcatctga atcacaaagg    1080
agcaggcatg gaagtgttct gagcagcaat tttacttacc acacgagtga tggagatgca    1140
ttgctccttc tctgaaggga atcccaaagc cttgtgtcta cagagaacct ggagttcctg    1200
aacctgatgc tgactagtga ggaaagattt tgttgttat ttcttacagg cacaaaatga    1260
tggacccaat gcacacaaaa caaccctaga gtgttgttga gaattgtgct caaaatttga    1320
agaatgaaca aattgaactc tttgaatgac aaagagtaga catttctctt actgcaaatg    1380
tcatcagaac tttttggttt gcagatgaca aaaattcaac tcagactagt ttagttaaat    1440
```

| | |
|---|---|
| gagggtggtg aatattgttc atattgtggc acaagcaaaa gggtgtctga gccctcaaag | 1500 |
| tgagggaaa ccagggcctg agccaagcta gaattccctc tctctgactc tcaaatctttt | 1560 |
| tagtcattat agatccccca gactttacat gacacagctt tatcaccaga gagggactga | 1620 |
| cacccatgtt tctctggccc caagggaaaa ttcccaggga agtgctctga taggccaagt | 1680 |
| ttgtatcagg tgcccatccc tggaaggtgc tgttatccat ggggaaggga tatataagat | 1740 |
| ggaagcttcc agtccaatct catggagaag cagaaataca tatttccaag aagttggatg | 1800 |
| ggtgggtact attctgatta cacaaaacaa atgccacaca tcacccttac catgtgcctg | 1860 |
| atccagcctc tccctgatt acaccagcct cgtcttcatt aagccctctt ccatcatgtc | 1920 |
| cccaaacctg caagggctcc ccactgccta ctgcatcgag tcaaaactca aatgcttggc | 1980 |
| ttctcatacg tccaccatgg ggtcctacca atagattccc cattgcctcc tccttcccaa | 2040 |
| aggactccac ccatcctatc agcctgtctc ttccatatga cctcatgcat ctccacctgc | 2100 |
| tcccaggcca gtaagggaaa tagaaaaacc ctgcccccaa ataagaaggg atggattcca | 2160 |
| accccaactc cagtagcttg gacaaatca agcttcagtt tcctggtctg tagaagaggg | 2220 |
| ataaggtacc tttcacatag agatcatcct ttccagcatg aggaactagc caccaactct | 2280 |
| tgcaggtctc aacccttttg tctgcctctt agacttctgc tttccacacc tgcactgctg | 2340 |
| tgctgtgccc aagttgtggt gctgacaaag cttggaagag cctgcaggtg ccttggccgc | 2400 |
| gtgcatagcc cagacacaga agaggctggt tcttacgatg gcacccagtg agcactccca | 2460 |
| agtctacaga gtgatagcct tccgtaaccc aactctcctg gactgccttg aatatcccct | 2520 |
| cccagtcacc ttgtgcaagc ccctgcccat ctgggaaaat accccatcat tcatgctact | 2580 |
| gccaacctgg ggagccaggg ctatgggagc agcttttttt tccccctag aaacgtttgg | 2640 |
| aacaatgtaa aactttaaag ctcgaaaaca attgtaataa tgctaaagaa aaagtcatcc | 2700 |
| aatctaacca catcaatatt gtcattcctg tattcacccg tccagacctt gttcacactc | 2760 |
| tcacatgttt agagttgcaa tcgtaatgta cagatggttt tataatctga tttgttttcc | 2820 |
| tcttaacgtt agaccacaaa tagtgctcgc tttctatgta gtttggtaat tatcatttta | 2880 |
| gaagactcta ccagactgtg tattcattga agtcagatgg ggtaactgtt aaattgctgt | 2940 |
| gtatctgata gctctttggc agtctatatg tttgtataat gaatgagaga ataagtcatg | 3000 |
| ttccttcaag atcatgtacc ccaatttact tgccattact caattgataa acatttaact | 3060 |
| tgtttccaat gtttagcaaa tacatatttt atagaacttc | 3100 |

<210> SEQ ID NO 2
<211> LENGTH: 783
<212> TYPE: DNA
<213> ORGANISM: Homo sapiens

<400> SEQUENCE: 2

| | |
|---|---|
| atgcagagga tctcctccct catccatctc tctctcttct gggcaggagt catgtcagcc | 60 |
| attgagttgg tgcctgaaca ccaaacagtg cctgtgtcaa tagggggtccc tgccacccctc | 120 |
| aggtgctcca tgaaaggaga agcgatcggt aactactata tcaactggta caggaagacc | 180 |
| caaggtaaca caatgacttt catataccga gaaaaggaca tctatggccc tggtttcaaa | 240 |
| gacaatttcc aaggtgacat tgatattgca aagaacctgg ctgtacttaa gatacttgca | 300 |
| ccatcagaga gagatgaagg gtcttactac tgtgcctgtg acaccttggg gatggggggg | 360 |
| gaatacaccg ataaactcat ctttggaaaa ggaacccgtg tgactgtgga accaagaagt | 420 |

| | |
|---|---|
| cagcctcata ccaaaccatc cgtttttgtc atgaaaaatg gaacaaatgt cgcttgtctg | 480 |
| gtgaaggaat tctaccccaa ggatataaga ataaatctcg tgtcatccaa gaagataaca | 540 |
| gagtttgatc ctgctattgt catctctccc agtgggaagt acaatgctgt caagcttggt | 600 |
| aaatatgaag attcaaattc agtgacatgt tcagttcaac acgacaataa aactgtgcac | 660 |
| tccactgact ttgaagtgaa gacagattct acagatcacg taaaaccaaa ggaaactgaa | 720 |
| aacacaaagc aaccttcaaa gagctgccat aaacccaaag ccatagttca taccgagaag | 780 |
| taa | 783 |

<210> SEQ ID NO 3
<211> LENGTH: 5191
<212> TYPE: DNA
<213> ORGANISM: Homo sapiens

<400> SEQUENCE: 3

| | |
|---|---|
| gcggccgcgg gctctcgcgg ggcggcgacg ccgcggggag gatgctgctt gccgcgcccg | 60 |
| cgtcctcacc gtcctcccgg gccgcctgct ggggctttgt tgtggcccgg acgccgcggg | 120 |
| ccacccctg aagtcgcctg ccgccgccgc cgccgcacct agcggacggg cgggcgggcg | 180 |
| cgcgtgtgcc caggagtgcg cgcctgtcgc ggtggtgggt gcaggactgg acccacgggc | 240 |
| ccattgtgcg cccgcccgcg gcagccagga ccatgtgggt gaacccggag gaggtgttgc | 300 |
| tggccaacgc gctgtggatc accgagaggg ccaaccccata cttcatcctg cagcggagga | 360 |
| agggccacgc cggcgatgga ggcggcggcg gcggactggc gggcctgctg gtgggtaccc | 420 |
| ttgatgttgt gttggactcc agcgcccggg tcgctcctta ccgaatcttg taccagactc | 480 |
| cagactccct ggtctactgg accatcgcct gtggtggttc caggaaagaa atcactgaac | 540 |
| actgggaatg gcttgagcaa atctcttgc agacactctc catctttgaa atgagaatg | 600 |
| atatcaccac atttgtgaga ggaaaaatac agggcatcat tgcagaatac aacaaaatca | 660 |
| atgatgtaaa ggaagatgat gacacggaga gtttaaaga agccattgtg aaatttcata | 720 |
| ggctgtttgg gatgccagag aagagaaac tcgtcaacta ttactcttgc agctattgga | 780 |
| aggggaaggt cccccgtcag ggttggatgt acctcagcat taaccacctt tgctttatt | 840 |
| cttttcttat gggaagggaa gcgaaactgg tcatccggtg ggtagacatc actcagctcg | 900 |
| agaagaatgc caccctgctt ctgcctgatg tgatcaaagt gagcacacgg tccagtgagc | 960 |
| atttcttctc tgtattcctc aacatcaacg agaccttcaa gttaatggag cagcttgcca | 1020 |
| acatagccat gaggcaactc ttagacaatg agggatttga acaagatcga tccctgccca | 1080 |
| aactcaaaag gaaatctcct aaaaaagtgt ctgctctaaa acgtgatctt gatgccaggg | 1140 |
| caaagagtga gagataccgt gcacttttcc ggctgcccaa agatgaaaaa ttagatggcc | 1200 |
| acacagactg cactctctgg actccatta acaaaatgca cattttgggg cagatgtttg | 1260 |
| tgtccacaaa ttcatctgt tttaccagca aggaggagaa cttatgtagc ctcattatcc | 1320 |
| cgctccgtga ggtgacaatt gtggaaaagg cagacagctc cagtgtgctc cccagtccct | 1380 |
| tatccatcag cacccgaaac aggatgacct tcctatttgc caacttgaaa gatagagact | 1440 |
| ttctagtgca gaggatctca gatttcctgc aacagactac ttccaaaata tattctgaca | 1500 |
| aggagtttgc aggaagttac aacagttcag atgatgaggt gtactctcga cccagcagcc | 1560 |
| tcgtctcctc cagcccccag agaagcacga gctctgatgc tgatggagag cgccagttta | 1620 |
| acctaaatgg caacagcgtc cccacagcca cacagaccct gatgaccatg tatcggcggc | 1680 |
| ggtctcccga ggagttcaac ccgaaattgg ccaaagagtt tctgaaagag caagcctgga | 1740 |

```
agattcactt tgctgagtat gggcaaggga tctgcatgta ccgcacagag aaaacgcggg   1800
agctggtgtt gaagggcatc ccggagagca tgcgtgggga gctctggctg ctgctgtcag   1860
gtgccatcaa tgagaaggcc acacatcctg gtactatga agacctagtg gagaagtcca   1920
tggggaagta taatctcgcc acggaggaga ttgagaggga tttacaccgc tcccttccag   1980
aacacccagc ttttcagaat gaaatgggca ttgctgcact aaggagagtc ttaacagctt   2040
atgcttttcg aaatcccaac atagggtatt gccaggccat gaatattgtc acttcagtgc   2100
tgctgcttta tgccaaagag gaggaagctt tctggctgct tgtggctttg tgtgagcgca   2160
tgctcccaga ttactacaac accagagttg tgggtgcact ggtggaccaa ggtgtctttg   2220
aggagctagc acgagactac gtcccacagc tgtacgactg catgcaagac ctgggcgtga   2280
tttccaccat ctccctgtct tggttcctca cactatttct cagtgtgatg cctttgaga   2340 gtgcagttgt ggttgttgac tgtttcttct atgaaggaat aaagtgata ttccagttgg   2400 ccctagctgt gctggatgca aatgtggaca aactgttgaa ctgcaaggat gatggggagg   2460
ccatgaccgt tttgggaagg tatttagaca gtgtgaccaa taaagacagc acactgcctc   2520
ccattcctca cctccactcc ttgctcagcg atgatgtgga accttaccct gaggtagaca   2580
tctttagact catcagaact tcctacgaga aattcggaac tatccgggca gatttgattg   2640
aacagatgag attcaaacag agactgaaag tgatccagac gctggaggat actacgaaac   2700
gcaacgtggt acgaaccatt gtgacagaaa cttcctttac cattgatgag ctggaagaac   2760
tttatgctct tttcaaggca gaacatctca ccagctgcta ctggggcggg agcagcaacg   2820
cgctggaccg gcatgacccc agcctgccct acctggaaca gtatcgcatt gacttcgagc   2880
agttcaaggg aatgtttgct cttctctttc cttgggcatg tggaactcac tctgacgttc   2940
tggcctcccg cttgttccag ttattagatg aaaatggaga ctctttgatt aacttccggg   3000
agtttgtctc tgggctaagt gctgcatgcc atggggacct cacagagaag ctcaaactcc   3060
tgtacaaaat gcacgtcttg cctgagccat cctctgatca agatgaacca gattctgctt   3120
ttgaagcaac tcagtacttc tttgaagata ttaccccaga atgtacacat gttgttggat   3180
tggatagcag aagcaaacag ggtgcagatg atggctttgt tacggtgagc ctaaagccag   3240
acaaagggaa gagagcaaat tcccaagaaa atcgtaatta tttgagactg tggactccag   3300
aaaataaatc taagtcaaag aatgcaaagg atttacccaa attaaatcag ggcagttca   3360 ttgaactgtg taagacaatg tataacatgt tcagcgaaga ccccaatgag caggagctgt   3420
accatgccac ggcagcagtg accagcctcc tgctggagat tgggagtc ggcaagttgt   3480 tcgtggccca gcctgcaaag gaggacaagc tgcactgcga ggacatcgga gaggacacgg   3540
tcctggtgcg gagcggccag ggcacggcgg cactgccccg gagcaccggc ctggaccggg   3600
actgggccat caccttcgag cagttcctgg cctccctctt aactgagcct gccctggtca   3660
agtactttga caagcccgtg tgcatgatgg ccaggattac cagtgcaaaa acatccgga   3720 tgatgggcaa gcccctcacc tcggccagtg actatgaaat ctcggccatg tccggctgac   3780
acgggcgcct tcccggggga gtgggaggaa agggaggga gggatttttt atgttcttct   3840
gtgttgagtt ttttcttcct ttctttaaa ttaaatattt attagtacct ggcttgaagc   3900
ctagtgtttt cataatgtaa ttcaatgaaa actgttggag aaatatttaa acacctcaat   3960
gtaggtacat tacactcttg ttgcggggag gggattacc agaatacagt ttatttcgtg   4020
aattctaaaa aacaaaaaga tgaatctgtc agtgatatgt gtgtattata acttattaat   4080
```

| | | |
|---|---|---|
| cttgctgttg agctgtatac atggtttaaa aaatagtact gtttaatgct aagtaaggca | 4140 | |
| gcagtcattt gtgtattcag cttttttaaa taaaattaga gctgtaagga aaatgaaaag | 4200 | |
| ccacaaatgc aagactgttc ttaaatggaa ggcatagtca gcgagggtaa atcctatacc | 4260 | |
| actttaggaa gtattaaaaa tattttttaag atttgaaata tatttcatag aagtcctcta | 4320 | |
| ttcaaaatca tattccacag atgttcccct tcaaagggaa acatttggg gttctaaaca | 4380 | |
| gttatgaaag taagtgattt ttacatgatt ccagaataac acttgtattg accaatttaa | 4440 | |
| acagatacca gaccaatttt gcatttaaga aattgttctg attatttacg tcaactcatt | 4500 | |
| agaattcagt gaaaagtaac agtcttttgt cacagagaat ctgaaagtag cagcaaagac | 4560 | |
| agagggctca tgacaggttt ttgcttttgc tttgctttttg tttttgaaag agtaaaagta | 4620 | |
| ctgatgcttc tgatactgga tgtttagctt cttactgcaa aaacataagt aaaacagtca | 4680 | |
| actttaccat ttccgtattc tccatagatt gaagaaattt ataccacata tcgcatatga | 4740 | |
| ccatctttcc atcaaatcaa tgtagagata atgtaaactg aaaaaaaatc tgcaagataa | 4800 | |
| tgtaactgaa tgttttaaaa acagaacttg tcactttata taaaagaata gtatgctcta | 4860 | |
| tttcctgaat ggatgtggaa atgaaagcta gcgcacctgc actttgaatt cttgcttctt | 4920 | |
| ttttattact gttatgattt tgcttttttac agatgttgga cgattttttc ttctgattgt | 4980 | |
| tgaattcata atcatggtct catttccttt gcttctttgg aatatttctt tcaacacatt | 5040 | |
| cctttatttt attatacatt gtgtcctttt tttagctatt gctgctgttg ttttttattc | 5100 | |
| tatttacagg atgattttta aactgtcaaa tgaagtagtg ttaacctcaa ataggctaaa | 5160 | |
| tgtgaacaaa taaaatacag caaatactca g | 5191 | |

<210> SEQ ID NO 4
<211> LENGTH: 5521
<212> TYPE: DNA
<213> ORGANISM: Homo sapiens

<400> SEQUENCE: 4

| | | |
|---|---|---|
| cgccccgcat cgtgcccggc ccgtcgcgg agatcccgga cgaccgtcgc gggttgatgg | 60 | |
| tcgcattcca gatgtaaaca gcttcagaag cctgacggtc atatggtaga atcactgtgg | 120 | |
| actgagaccc acctttctag acctgaagcc caggaggagg aagaggaggc tggttggtac | 180 | |
| catgggcata atgctctgaa tcctagtctc tcacctagta tgtgagcagt ccctgcagat | 240 | |
| ggcccatttg gagatcttga caaagcctct tctgtttcca atggggtttt tggcgcattc | 300 | |
| tcacagactt agatgaaact gtgatggcca ccgcaggggg caggtgctga catcgtcccc | 360 | |
| agccctgtgg ctgttcatcc ggacatcatt tccaacctca atatctaaat gccacagtgc | 420 | |
| tcttggagca agttgggctg ggaccactg ttgccttta agaccataaa accatgggaa | 480 | |
| acgcagaaag tcaacatgta gagcacgagt tttatggaga aaagcatgcc agcctggggc | 540 | |
| gcaacgacac ttcccgctcc ctgcgcctct cgcacaagac gcggaggacc aggcacgctt | 600 | |
| cctcggggaa ggtgatccac aggaactccg aagtgagcac ccgatccagc agcacccccca | 660 | |
| gcatccccca gtccctggct gaaaatggcc tggagcccct tcccaagat ggtaccctag | 720 | |
| aagacttcgg gagccccatc tgggtggacc gagtggacat gggcttgaga cctgtgtctt | 780 | |
| acactgactc ttctgtcact cccagcgtag acagcagcat cgtcctcaca gcagcctctg | 840 | |
| tgcagagcat gccagacact gaggagagca ggctttacgg ggatgacgct acatatttgg | 900 | |
| ctgagggagg caggaggcag cattcctata catccaatgg gccccactttc atggagacgg | 960 | |
| cgagctttaa gaagaaacgc tccaaatctg cagacatctg gcgggaggac agcctggaat | 1020 | |

```
tctcactctc tgatctgagc caagaacatt taacaagcaa cgaagaaatc ttgggttccg   1080
ccgaagagaa ggactgcgag gaggctcggg ggatggaaac gcgggcgagt ccgcggcagc   1140
tcagcacctg tcagagagcc aattccttgg gtgacttgta tgctcagaaa aactctggag   1200
tgacagcaaa catggggccg gggagcaaat ttgcaggcta ctgtcggaat tggtgtctg    1260 atattcccaa tcttgcaaac cataagatgc caccagctgc tgctgaagag actcctccgt   1320
acagtaatta taacacactt ccctgtagga aatctcactg tctctctgaa ggtgccacca   1380
acccacaaat tagccatagc aacagcatgc aaggcagaag agctaaaaca actcaggatg   1440
ttaatgcagg cgagggcagt gagtttgcag acagtgggat tgaaggggcc actaccgaca   1500
cggacctcct gtccaggcga tctaatgcca ccaactccag ctactcaccc accacaggcc   1560
gggcctttgt gggcagcgac agcggcagca gctccaccgg ggatgcggct cgtcaggggg   1620
tgtacgagaa cttccggcgg gagctggaga tgagcaccac caacagcgag agcctggagg   1680
aggccggctc tgcgcacagc gatgagcaga gcagcggcac cctgagctct ccgggccagt   1740
cggacatcct gctgaccgcc gcacagggca cggtgcgcaa ggccggcgcc ctggccgtca   1800
agaacttcct ggtgcacaag aagaacaaga aggtggagtc agccacccgg aggaagtgga   1860
agcactactg ggtgtccctg aaaggatgca cgctattttt ctacgagagc gacggcaggt   1920
ctgggataga ccacaacagc atccccaaac acgccgtctg ggtggagaac agcattgtgc   1980
aggctgtgcc tgagcaccc aagaaggact ttgtcttctg cctcagcaat tccctgggtg   2040
atgccttcct ttttcagacc actagccaga cggagcttga aaactggatc accgccatcc   2100
actctgcctg cgccactgcg gtcgcgaggc accaccacaa ggaagacacg ctccgactcc   2160
tgaaatcaga gatcaaaaaa ctggaacaga agattgacat ggatgaaaag atgaagaaaa   2220
tgggtgaaat gcagctgtct tcagtcactg actcaaagaa aaagaaaaca atattagatc   2280
agatctttgt ctgggagcaa atctcgagc agttccaaat ggacctgttt cgtttccgct   2340
gttatttagc cagccttcag ggtggggagc tgccaaaccc caaaaggctt ctcgcttttg   2400
caagtcgacc aacgaaagtg gccatgggcc gccttggaat cttttcggta tcatcgtttc   2460
atgccctggt ggcagcacgc actggtgaaa ctggagtgag aagacgtact caggccatgt   2520
ccagatccgc gagcaagcga aggagcaggt tttcttctct gtggggtctg gatactacct   2580
ccaaaaagaa gcagggacgg ccaagcatca atcaggtgtt tggagaggga accgaagctg   2640
taaagaaatc tttagaggga atatttgatg acattgttcc agatggcaag agggagaaag   2700
aagtggtctt acctaacgtt caccagcaca accctgactg cgacatttgg gtccacgagt   2760
atttcactcc atcctggttc tgtctgccca ataatcagcc tgccctgacg gtcgtccggc   2820
caggcgacac tgcacgggac accctggagc tgatttgcaa gacacatcaa ctggatcatt   2880
ctgctcatta cctgcgcctg aaatttctaa tagaaaacaa aatgcagctc tatgttccac   2940
agcccgagga agacatctat gagctgctgt acaaagaaat tgaaatctgt ccaaaagtca   3000
ctcacagcat ccacattgag aagtcagata cagctgctga tacttacggg ttttcacttt   3060
cttctgtgga agaagatggt attcgaaggc tgtacgtgaa tagtgtgaag gaaaccggtt   3120
tagcttccaa gaaaggcctg aaagcaggag atgagattct tgagatcaat aatcgtgctg   3180
ctgacgccct gaactcttct atgctcaaag atttcctctc acaaccctcg ctgggcctcc   3240
tggtgaggac ctaccccgag ctggaggaag gagtggagct gctggaaagc ccgcccacc    3300 gagtggacgg ccctgccgac cttgacgaga gccccctcgc ctttctcacc agcaacccag   3360
```

```
ggcacagcct ttgcagcgag cagggcagca gtgctgagac cgctccagag gagaccgagg    3420
ggccagactt ggaatcctca gatgagactg atcacagcag caagagtaca gaacaggtgg    3480
ccgcattttg ccgcagtttg catgagatga acccctctga ccagaaccca tctcctcagg    3540
actccacggg gcctcagctg gcgaccatga gacaactctc ggatgcagat aacgtgcgca    3600
aggtgatctg cgagctcctg gagacggagc gcacctacgt gaaggattta aactgtctta    3660
tggagagata cctaaagcct cttcaaaaag aaacttttct cacccaggat gagcttgacg    3720 tgcttttgg aaatttaacg gaaatggtag agtttcaagt agaattcctt aaaactctag    3780
aagatggagt gagactggta cctgatttgg aaaagcttga gaaggttgat caatttaaga    3840
aagtgctgtt ctctctgggg ggatcattcc tgtattatgc tgaccgcttc aagctctaca    3900
gtgccttctg cgccatccac acaaaagttc caaggtcct ggtgaaagcc aagacagaca    3960
cggctttcaa ggcattcttg gatgcccaga acccgaagca gcagcactca tccacgctgg    4020
agtcgtacct catcaagccc atccagagga tcctcaagta cccacttctg ctcagggagc    4080
tgttcgccct gaccgatgcg gagagcgagg agcactacca cctggacgtg gccatcaaga    4140
ccatgaacaa ggttgccagt cacatcaatg agatgcagaa aatccatgaa gagtttgggg    4200
ctgtgtttga ccagctgatt gctgaacaga ctggtgagaa aaaagaggtt gcagatctga    4260
gcatgggaga cctgcttttg cacactaccg tgatctggct gaacccgccg gcctcgctgg    4320
gcaagtggaa aaaggaacca gagttggcag cattcgtctt caaaactgct gtggtccttg    4380
tgtataaaga tggttccaaa cagaagaaga aacttgtagg atctcacagg ctttccattt    4440
atgaggactg ggaccccttc agatttcgac acatgatccc cacggaagcg ctgcaggttc    4500
gagctttggc gagtgcagat gcagaggcaa atgccgtgtg tgaaattgtc catgtaaaat    4560
ccgagtctga agggaggccg gagagggtct ttcacttgtg ctgcagctcc ccagagagcc    4620
gaaaggattt cctaaaggct gtgcattcaa tcctgcgtga taagcacaga agacagctcc    4680
tcaaaaccga gagccttccc tcatcccagc aatatatgtcc ttttggaggc aaaagattgt    4740
gtgcactgaa gggggccagg ccggccatga gcagggcagt gtctgcccca gcaagtctc    4800 ttgggaggag gaggcggcgg ctggctcgaa acaggtttac cattgattct gatgccgtct    4860
ccgcaagcag cccggagaaa gagtcccagc agccccccgg tggtggggac actgaccgat    4920
gggtagagga gcagtttgat cttgctcagt atgaggagca agatgacatc aaggagacag    4980
acatcctcag tgacgatgat gagttctgtg agtccgtgaa gggtgcctca gtggacagag    5040
acctgcagga gcggcttcag gccacctcca tcagtcagcg ggaaagaggc cggaaaaccc    5100
tggatagtca cgcgtcccgc atggcacagc tcaagaagca agctgccctg tcgggggatca    5160 atggaggcct ggagagcgca agcgaggaag tcatttgggt taggcgtgaa gactttgccc    5220
cctccaggaa actgaacact gagatctgac tgcgtcacct gccccgtaga gaatgtgtgt    5280
agatacttcc tgccctaact ctgcccaccc tcctgtaccg tcgacaagaa tgtcccctta    5340
ggtcgcgctc ttgcacacac ggttttggca gctgacttgg ttctgaagcc atgtagccac    5400
ccaactttgt cattttcaac aacatcagaa agaattgatc agaatcccaa ataaaaccca    5460
aaagtgtcta atgtattcat tcattagcta actaaaagcc caaaaaagac aagcaccca    5520 g                                                                   5521

<210> SEQ ID NO 5
<211> LENGTH: 1498
<212> TYPE: DNA
<213> ORGANISM: Homo sapiens
```

<400> SEQUENCE: 5

```
accaaacctc ttcgaggcac aaggcacaac aggctgctct gggattctct tcagccaatc      60
ttcattgctc aagtgtctga agcagccatg gcagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atggcggcat ccagctacga     240
atctccgacc accactacag caagggcttc aggcaggccg cgtcagttgt tgtggccatg     300
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag agaagaaag taatgacaaa      600
atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat ttgtcttcaa caagatagaa atcaataaca agctgaatt tgagtctgcc      780
cagttcccca actggtacat cagcacctct caagcagaaa acatgcccgt cttcctggga     840
gggaccaaag gcggcagga tataactgac ttcaccatgc aatttgtgtc ttcctaaaga      900
gagctgtacc cagagagtcc tgtgctgaat gtggactcaa tccctagggc tggcagaaag     960
ggaacagaaa ggttttttgag tacggctata gcctggactt tcctgttgtc tacaccaatg    1020
cccaactgcc tgccttaggg tagtgctaag aggatctcct gtccatcagc caggacagtc    1080
agctctctcc tttcagggcc aatccccagc ccttttgttg agccaggcct ctctcacctc    1140
tcctactcac ttaaagcccg cctgacagaa accacggcca catttggttc taagaaaccc    1200
tctgtcattc gctcccacat tctgatgagc aaccgcttcc ctatttattt atttatttgt    1260
ttgtttgttt tattcattgg tctaatttat tcaagggggg caagaagtag cagtgtctgt    1320
aaaagagcct agtttttaat agctatgaa tcaattcaat ttggactggt gtgctctctt      1380
taaatcaagt cctttaatta agactgaaaa tatataagct cagattattt aaatgggaat    1440
atttataaat gagcaaatat catactgttc aatggttctg aaataaactt cactgaag      1498
```

<210> SEQ ID NO 6
<211> LENGTH: 1245
<212> TYPE: DNA
<213> ORGANISM: Homo sapiens

<400> SEQUENCE: 6

```
cgggcgtgta acccacgggt gcgcgcccac gaccgccaga ctcgagcagt ctctggaaca      60
cgctgcgggg ctcccgggcc tgagccaggt ctgttctcca cgcaggtgtt ccgcgcgccc     120
cgttcagcca tgtcgtccgg catccatgta gcgctggtga ctgaggcaa caagggcatc     180
ggcttggcca tcgtgcgcga cctgtgccgg ctgttctcgg gggacgtggt gctcacggcg    240
cgggacgtga cgcggggcca ggcggccgta cagcagctgc aggcggaggg cctgagcccg    300
cgcttccacc agctggacat cgacgatctg cagagcatcc gcgccctgcg cgacttcctg    360
cgcaaggagt acgggggcct ggacgtgctg gtcaacaacg cgggcatcgc cttcaaggtt    420
gctgatccca cacccttca tattcaagct gaagtgacga tgaaaacaaa tttcttggt      480
acccgagatg tgtgcacaga attactccct ctaataaaac cccaagggag agtggtgaac    540
```

| | |
|---|---|
| gtatctagca tcatgagcgt cagagcccct aaaagctgca gcccagagct gcagcagaag | 600 |
| ttccgcagtg agaccatcac tgaggaggag ctggtggggc tcatgaacaa gtttgtggag | 660 |
| gatacaaaga agggagtgca ccagaaggag ggctggccca gcagcgcata cggggtgacg | 720 |
| aagattggcg tcaccgttct gtccaggatc acgccagga aactgagtga gcagaggaaa | 780 |
| ggggacaaga tcctcctgaa tgcctgctgc ccagggtggg tgagaactga catggcggga | 840 |
| cccaaggcca ccaagagccc agaagaaggt gcagagaccc ctgtgtactt ggcccttttg | 900 |
| cccccagatg ctgagggtcc ccatggacaa tttgtttcag agaagagagt tgaacagtgg | 960 |
| tgagctgggc tcacagctcc atccatgggc cccattttgt accttgtcct gagttggtcc | 1020 |
| aaagggcatt tacaatgtca taaatatcct tatataagaa aaaaaatgat ctcttatcaa | 1080 |
| ttagcactca ctaatgtact actaattgag caacctacgc actcagttga ctacgtaaat | 1140 |
| ctgtcaggtc ttttgtgatt tcctctgatg caggagagga aaaattgtaa ttgatgaaaa | 1200 |
| taatgaatga aaatcaacag atgaataaat ggttctttat aagtg | 1245 |

<210> SEQ ID NO 7
<211> LENGTH: 2460
<212> TYPE: DNA
<213> ORGANISM: Homo sapiens

<400> SEQUENCE: 7

| | |
|---|---|
| gtgtggaaca tgccttcacc acctccagct tctgctgccg gaggctgcac ccacctgtgc | 60 |
| ccatggcctg cacaggccca tcacttccta gcgccttcga cattctaggt gcagcaggcc | 120 |
| aggacaagct cttgtatctg aagcacaaac tgaagacccc acgcccaggc tgccaggggc | 180 |
| aggacctcct gcatgccatg gttctcctga agctgggcca ggaaactgag gccaggatct | 240 |
| ctctagaggc attgaaggcc gatgcggtgg cccggctggt ggcccgccag tgggctggcg | 300 |
| tggacagcac cgaggaccca gaggagcccc agatgtgtc ctgggctgtg gcccgcttgt | 360 |
| accacctgct ggctgaggag aagctgtgcc ccgcctcgct gcgggacgtg gcctaccagg | 420 |
| aagccgtccg caccctcagc tccagggacg accaccggct gggggaactt caggatgagg | 480 |
| cccgaaaccg gtgtgggtgg gacattgctg gggatccagg gagcatccgg acgctccagt | 540 |
| ccaatctggg ctgcctccca ccatcctcgg ctttgccctc tgggaccagg agcctcccac | 600 |
| gccccattga cggtgtttcg gactggagcc aagggtgctc cctgcgatcc actggcagcc | 660 |
| ctgcctccct ggccagcaac ttggaaatca gccagtcccc taccatgccc ttcctcagcc | 720 |
| tgcaccgcag cccacatggg cccagcaagc tctgtgacga cccccaggcc agcttggtgc | 780 |
| ccgagcctgt ccccggtggc tgccaggagc ctgaggagat gagctggccg ccatcggggg | 840 |
| agattgccag cccaccagag ctgccaagca gcccacctcc tgggcttccc gaagtggccc | 900 |
| cagatgcaac ctccactggc ctccctgata ccccgcagc tccagaaacc agcaccaact | 960 |
| acccagtgga gtgcaccgag gggtctgcag gcccccagtc tctccccttg cctattctgg | 1020 |
| agccggtcaa aaaccctgc tctgtcaaag accagacgcc actccaactt tctgtagaag | 1080 |
| ataccaccctc tccaaatacc aagccgtgcc cacctactcc caccacccca gaaacatccc | 1140 |
| ctcctcctcc tcctcctcct ccttcatcta ctccttgttc agctcacctg accccctcct | 1200 |
| ccctgttccc ttcctccctg gaatcatcat cggaacagaa attctataac tttgtgatcc | 1260 |
| tccacgccag ggcagacgaa cacatcgccc tgcgggttcg ggagaagctg gaggcccttg | 1320 |
| gcgtgcccga cggggccacc ttctgcgagg atttccaggt gccggggcgc ggggagctga | 1380 |
| gctgcctgca ggacgccata gaccactcag cttttcatcat cctacttctc acctccaact | 1440 |

```
tcgactgtcg cctgagcctg caccaggtga accaagccat gatgagcaac ctcacgcgac    1500
aggggtcgcc agactgtgtc atccccttcc tgccctgga gagctcccg gcccagctca      1560 gctccgacac ggccagcctg ctctccgggc tggtgcggct ggacgaacac tcccagatct    1620
tcgccaggaa ggtggccaac accttcaagc cccacaggct tcaggcccga aggccatgt    1680 ggaggaagga acaggacacc cgagccctgc gggaacagag ccaacacctg acggtgagc     1740 ggatgcaggc ggcggcactg aacgcagcct actcagccta cctccagagc tacttgtcct   1800
accaggcaca gatggagcag ctccaggtgg cttttgggag ccacatgtca tttgggactg    1860
gggcgcccta tggggctcga atgcccttttg ggggccaggt gccctggga gcccgccac     1920 cctttcccac ttggccgggg tgccgcagc cgccacccct gcacgcatgg caggctggca    1980
cccccccacc gccctcccca cagcagcag cttttccaca gtcactgccc ttccgcagt     2040 ccccagcctt ccctacggcc tcacccgcac ccctcagag cccagggctg caaccctca    2100 ttatccacca cgcacagatg gtacagctgg ggctgaacaa ccacatgtgg aaccagagag   2160
ggtcccaggc gcccgaggac aagacgcagg aggcagaatg accgcgtgtc cttgcctgac   2220
cacctgggga acacccctgg acccaggcat cggccaggac cccatagagc ccccggtct    2280 gccctgtgcc ctgtggacag tggaagatga ggtcatctgc cactttcagg acattgtccg   2340
ggagcccttc atttaggaca aaacgggcgc gatgatgccc tggctttcag ggtggtcaga   2400
actggatacg gtgtttacaa ttccaatctc tctatttctg ggtgaagggt cttggtggtg   2460

<210> SEQ ID NO 8
<211> LENGTH: 2650
<212> TYPE: DNA
<213> ORGANISM: Homo sapiens

<400> SEQUENCE: 8
gccgcgctgg tggcggcggc gcgtcgttgc agttgcgcca tctgtcagga gcggagccgg     60
cgaggagggg gctgccgcgg gcgaggagga ggggtcgccg cgagccgaag gccttcgaga    120
cccgcccgcc gcccggcggc gagagtagag gcgaggttgt tgtgcgagcg gcgcgtcctc    180
tcccgcccgg gcgcgccgcg cttctcccag cgcaccgagg accgcccggg cgcacacaaa   240
gccgccgccc gcgccgcacc gcccggcggc cgccgcccgc gccagggagg gattcggccg    300
ccgggccggg gacaccccgg cgccgccccc tcggtgctct cggaaggccc accggctccc    360
gggcccgccg ggacccccc ggagccgcct cggccgcgcc ggaggagggc ggggagagga    420
ccatgtgagt gggctccgga gcctcagcgc cgcgcagttt ttttgaagaa gcaggatgct    480
gatctaaacg tggaaaaaga ccagtcctgc ctctgttgta aagacatgt ggtgtatata    540 aagtttgtga tcgttggcgg acattttgga atttagataa tgggctgtgt gcaatgtaag    600
gataaagaag caacaaaact gacggaggag agggacggca gcctgaacca gagctctggg   660
taccgctatg gcacagaccc caccctcag cactacccca gcttcggtgt gacctccatc    720
cccaactaca acaacttcca cgcagccggg ggccaaggac tcaccgtctt tggaggtgtg   780
aactcttcgt ctcatacggg gaccttgcgt acgagaggag gaacaggagt gacactcttt   840 gtggccctttt atgactatga agcacggaca gaagatgacc tgagttttca caaggagaa    900 aaatttcaaa tattgaacag ctcggaagga gattggtggg aagcccgctc cttgacaact   960
ggagagacag gttacattcc cagcaattat gtggctccag ttgactctat ccaggcgaaa   1020
gagtggtact ttgaaaaact tggccgaaaa gatgctgagc gacagctatt gtcctttgga   1080
```

-continued

| | |
|---|---|
| aacccaagag gtacctttct tatccgcgag agtgaaacca ccaaggtgc ctattcactt | 1140 |
| tctatccgtg attgggatga tatgaaagga gaccatgtca acattataa aattcgcaaa | 1200 |
| cttgacaatg gtggatacta cattaccacc cgggcccagt ttgaaacact tcagcagctt | 1260 |
| gtacaacatt actcagagag agctgcaggt ctctgctgcc gcctagtagt tccctgtcac | 1320 |
| aaagggatgc caaggcttac cgatctgtct gtcaaaacca agatgtctg ggaaatccct | 1380 |
| cgagaatccc tgcagttgat caagagactg gaaatgggc agtttgggga agtatggatg | 1440 |
| ggtacctgga atggaaacac aaaagtagcc ataaagactc ttaaaccagg cacaatgtcc | 1500 |
| cccgaatcat tccttgagga agcgcagatc atgaagaagc tgaagcacga caagctggtc | 1560 |
| cagctctatg cagtggtgtc tgaggagccc atctacatcg tcaccgagta tatgaacaaa | 1620 |
| ggaagtttac tggatttctt aaaagatgga gaaggaagag ctctgaaatt accaaatctt | 1680 |
| gtggacatgg cagcacaggt ggctgcagga atggcttaca tcgagcgcat gaattatatc | 1740 |
| catagagatc tgcgatcagc aaacattcta gtggggaatg gactcatatg caagattgct | 1800 |
| gacttcggat tggcccgatt gatagaagac aatgagtaca cagcaagaca aggtgcaaag | 1860 |
| ttccccatca gtggacggc ccccgaggca gccctgtacg ggaggttcac aatcaagtct | 1920 |
| gacgtgtggt cttttggaat cttactcaca gagctggtca ccaaaggaag agtgccatac | 1980 |
| ccaggcatga caaccgggga ggtgctggag caggtggagc gaggctacag gatgccctgc | 2040 |
| ccgcaggact gccccatctc tctgcatgag ctcatgatcc actgctggaa aaaggaccct | 2100 |
| gaagaacgcc ccacttttga gtacttgcag agcttcctgg aagactactt taccgcgaca | 2160 |
| gagccccagt accaacctgg tgaaaacctg taaggcccgg gtctgcggag agaggccttg | 2220 |
| tcccagaggc tgccccaccc ctccccatta gctttcaatt ccgtagccag ctgctcccca | 2280 |
| gcagcggaac cgcccaggat cagattgcat gtgactctga agctgacgaa cttccatggc | 2340 |
| cctcattaat gacacttgtc cccaaatccg aacctcctct gtgaagcatt cgagacagaa | 2400 |
| ccttgttatt tctcagactt tggaaaatgc attgtatcga tgttatgtaa aaggccaaac | 2460 |
| ctctgttcag tgtaaatagt tactccagtg ccaacaatcc tagtgctttc cttttttaaa | 2520 |
| aatgcaaatc ctatgtgatt ttaactctgt cttcacctga ttcaactaaa aaaaaaaag | 2580 |
| tattattttc caaaagtggc ctctttgtct aaaacaataa aattttttt catgttttaa | 2640 |
| caaaaaccaa | 2650 |

<210> SEQ ID NO 9
<211> LENGTH: 3726
<212> TYPE: DNA
<213> ORGANISM: Homo sapiens

<400> SEQUENCE: 9

| | |
|---|---|
| cagcgctgct ccccgggcgc tcctcccgg gcgctcctcc ccaggcctcc cgggcgcttg | 60 |
| gatcccggcc atctccgcac ccttcaagtg ggtgtgggtg atttcctggc gggggagca | 120 |
| gccaggtgag cccaagatgc tgctgcgctc gaagcctgcg ctgccgccgc cgctgatgct | 180 |
| gctgctcctg gggccgctgg gtcccctctc ccctggcgcc ctgccccgac ctgcgcaagc | 240 |
| acaggacgtc gtggacctgg acttcttcac ccaggagccg ctgcacctgg tgagcccctc | 300 |
| gttcctgtcc gtcaccattg acgccaacct ggccacggac ccgcggttcc tcatcctcct | 360 |
| gggttctcca agcttcgta ccttggccag aggcttgtct cctgcgtacc tgaggtttgg | 420 |
| tggcaccaag acagacttcc taattttcga tcccaagaag gaatcaacct ttgaagagag | 480 |
| aagttactgg caatctcaag tcaaccagga tatttgcaaa tatggatcca tccctcctga | 540 |

-continued

```
tgtggaggag aagttacggt tggaatggcc ctaccaggag caattgctac tccgagaaca    600
ctaccagaaa aagttcaaga acagcaccta ctcaagaagc tctgtagatg tgctatacac    660
ttttgcaaac tgctcaggac tggacttgat ctttggccta aatgcgttat taagaacagc    720
agatttgcag tggaacagtt ctaatgctca gttgctcctg gactactgct cttccaaggg    780
gtataacatt tcttgggaac taggcaatga acctaacagt ttccttaaga aggctgatat    840
tttcatcaat gggtcgcagt taggagaaga ttttattcaa ttgcataaac ttctaagaaa    900
gtccaccttc aaaaatgcaa aactctatgg tcctgatgtt ggtcagcctc gaagaaagac    960
ggctaagatc tgaagagct tcctgaaggc tggtggagaa gtgattgatt cagttacatg    1020
gcatcactac tatttgaatg gacggactgc taccagggaa gatttctaa accctgatgt    1080 attggacatt tttatttcat ctgtgcaaaa agttttccag gtggttgaga gcaccaggcc    1140
tggcaagaag gtctggttag agaaacaag ctctgcatat ggaggcggag cgcccttgct    1200
atccgacacc tttgcagctg gctttatgtg gctggataaa ttgggcctgt cagcccgaat    1260
gggaatagaa gtggtgatga ggcaagtatt ctttggagca ggaaactacc atttagtgga    1320
tgaaaacttc gatcctttac ctgattattg gctatctctt ctgttcaaga aattggtggg    1380
caccaaggtg ttaatggcaa gcgtgcaagg ttcaaagaga aggaagcttc gagtataact    1440
tcattgcaca aacactgaca atccaaggta taagaagga gatttaactc tgtatgccat    1500
aaacctccat aatgtcacca agtacttgcg gttaccctat ccttttcta caagcaagt    1560 ggataaatac cttctaagac ctttgggacc tcatggatta cttccaaat ctgtccaact    1620 caatggtcta actctaaaga tggtggatga tcaaaccttg ccaccttaa tggaaaaacc    1680 tctccggcca ggaagttcac tgggcttgcc agctttctca tagtttttt ttgtgataag    1740 aaatgccaaa gttgctgctt gcatctgaaa ataaaatata ctagtcctga cactgaattt    1800
ttcaagtata ctaagagtaa agcaactcaa gttataggaa aggaagcaga taccttgcaa    1860
agcaactagt gggtgcttga gagacactgg gacactgtca gtgctagatt tagcacagta    1920
ttttgatctc gctaggtaga acactgctaa taataatagc taataatacc ttgttccaaa    1980
tactgcttag cattttgcat gttttacttt tatctaaagt tttgttttgt tttattattt    2040
atttatttat ttattttgtg acggagagag attccatctc aaaaaaacaa gttattaaaa    2100
atgtatatga atgctcctaa tatggtcagg aagcaaggag gcgaaggata tattatgagt    2160
tttaagaagg tgcttagctg tatatttatc tttcaaaatg tattagaaga tttagaatt    2220 cttttccttca tgtgccatct ctacaggcac ccatcagaaa aagcatactg ccgttaccgt    2280
gaaactggtt gtaaaagaga aactatctat ttgcaccttta aagacagct agattttgct    2340 gattttcttc tttcggtttt ctttgtcagc aataatatgt gagaggacag attgttagat    2400
atgatagtat aaaaaatggt taatgacaat tcagaggcga ggagattctg taaacttaaa    2460
attactataa atgaaattga tttgtcaaga ggataaattt tagaaaacac ccaataccttt    2520 ataactgtct gttaatgctt gcttttctc tacctttctt ccttgtttca gttgggaagc    2580
ttttggctgc aagtaacaga aactcctaat tcaaatggct taagcaataa ggaaatgtat    2640
attcccacat aactagacgt tcaaacaggc caggctccag cacttcagta cgtcaccagg    2700
ggatctgggt tcttcccagc tctctgctct gccatcttta gcgctggctt cattctcaga    2760
ctctggtagc atgatggctg tagctgtttc atgggcccct tcaaacctca tagcaaccag    2820
aggaagaaaa tgagccattt tttgagtctc cttcatagac ttgaataact cttttcaga    2880
```

| | | | | | |
|---|---|---|---|---|---|
| gcttctcaca | gcaaacctct | cctcatgtct | cctcatgtct | tattgttcag | aaatgggtaa | 2940 |
| tgtggccatt | tcaccagtca | ctgccaacaa | caacgaggtt | cctataattg | tctctgagta | 3000 |
| acccttttgga | atggagaggg | tgttggtcag | tctacaaact | gaacactgca | gttctgcgct | 3060 |
| ttttaccagt | gaaaaaatgt | aattatttc | ccctcttaag | gattaatatt | cttcaaatgt | 3120 |
| atgcctgtta | tggatatagt | atcttaaaa | ttttttattt | taatagcttt | aggggtacac | 3180 |
| actttttgct | tacagggtg | aattgtgtag | tggtgaagac | tcggcttta | atgtacttgt | 3240 |
| cacctgagtg | atgtacattg | tacccaatag | gtaatttttc | atccattacc | ctccttccgc | 3300 |
| cctcttccct | tctgagtctc | caacatccct | tataccactg | tgtatgttct | tgtgtaccta | 3360 |
| cagctaagct | tccacttata | agtgagaaca | tgcagtattt | ggttttccat | tcctgagtta | 3420 |
| cttcccttag | gataacagcc | cccagttccg | tccaagttgc | tgcaaaatac | attattcttc | 3480 |
| tttatggctg | agtaatagtc | catggtacat | ataaccaca | ttttctttat | ccacttatca | 3540 |
| gttgatggac | acttaggtta | attccattca | atttcattca | atttaagtat | atttgtaagg | 3600 |
| agctaaagct | gaaaattaaa | ttttagatct | ttcaatactc | ttaaattta | tatgtaagtg | 3660 |
| gtttttatat | tttcacattt | gaaataaagt | aattttata | accttgaaaa | aaaaaaaaa | 3720 |
| aaaaaa | | | | | | 3726 |

<210> SEQ ID NO 10
<211> LENGTH: 4912
<212> TYPE: DNA
<213> ORGANISM: Homo sapiens

<400> SEQUENCE: 10

| | | | | | |
|---|---|---|---|---|---|
| attgggtct | gctctaagct | gcagcaagag | aaactgtgtg | tgaggggaag | aggcctgttt | 60 |
| cgctgtcggg | tctctagttc | ttgcacgctc | tttaagagtc | tgcactggag | gaactcctgc | 120 |
| cattaccagc | tcccttcttg | cagaagggag | ggggaaacat | acatttattc | atgccagtct | 180 |
| gttgcatgca | ggcttttgg | cttcctacct | tgcaacaaaa | taattgcacc | aactccttag | 240 |
| tgccgattcc | gcccacagag | agtcctggag | ccacagtctt | ttttgctttg | cattgtagga | 300 |
| gagggactaa | gtgctagaga | ctatgtcgct | ttcctgagct | accgagagcg | ctcgtgaact | 360 |
| ggaatcaact | gcttcaggga | aaagaaaaa | aaaaaaaaaa | agacttgcct | gggaggccgc | 420 |
| gagaaacttg | cattggaagc | ttcagcaacc | agcattcgag | aaactcctct | ctactttagc | 480 |
| acggtctcca | gactcagccg | agagacagca | aactgcagcg | cggtgagaga | gcgagagaga | 540 |
| gggagagaga | gactctccag | cctgggaact | ataactcctc | tgcgagaggc | ggagaactcc | 600 |
| ttccccaaat | cttttgggga | cttttctctc | tttacccacc | tccgcccctg | cgaggagttg | 660 |
| aggggccagt | tcggccgccg | cgcgcgtctt | cccgttcggc | gtgtgcttgg | cccggggaac | 720 |
| cgggagggcc | cggcgatcgc | gcggcggccg | ccgcgagggt | gtgagcgcgc | gtgggcgccc | 780 |
| gccgagccga | ggccatggtg | cagcaaacca | acaatgccga | gaacacggaa | gcgctgctgg | 840 |
| ccggcgagag | ctcggactcg | ggcgccggcc | tcgagctggg | aatcgcctcc | tccccacgc | 900 |
| ccggctccac | cgcctccacg | ggcggcaagg | ccgacgaccc | gagctggtgc | aagaccccga | 960 |
| gtgggcacat | caagcgaccc | atgaacgcct | tcatggtgtg | gtcgcagatc | gagcggcgca | 1020 |
| agatcatgga | gcagtcgccc | gacatgcaca | acgccgagat | ctccaagcgg | ctgggcaaac | 1080 |
| gctggaagct | gctcaaagac | agcgacaaga | tccctttcat | tcgagaggcg | gagcggctgc | 1140 |
| gcctcaagca | catggctgac | taccccgact | acaagtaccg | gccaggaag | aaggtgaagt | 1200 |
| ccggcaacgc | caactccagc | tcctcggccg | ccgcctcctc | caagccgggg | gagaagggag | 1260 |

```
acaaggtcgg tggcagtggc gggggcggcc atggggcgg cggcggcggc gggagcagca   1320
acgcgggggg aggaggcggc ggtgcgagtg gcggcggcgc caactccaaa ccggcgcaga   1380
aaaagagctg cggctccaaa gtggcgggcg gcgcgggcgg tggggttagc aaaccgcacg   1440
ccaagctcat cctggcaggc ggcggcggcg gcgggaaagc agcggctgcc gccgccgcct   1500
ccttcgccgc cgaacaggcg ggggccgccg ccctgctgcc cctgggcgcc gccgccgacc   1560
accactcgct gtacaaggcg cggactccca gcgcctcggc ctccgcctcc tcggcagcct   1620
cggcctccgc agcgctcgcg gccccgggca agcacctggc ggagaagaag gtgaagcgcg   1680
tctacctgtt cggcggcctg ggcacgtcgt cgtcgcccgt gggcggcgtg ggcgcgggag   1740
ccgaccccag cgaccccctg ggcctgtacg aggaggaggg cgcgggctgc tcgcccgacg   1800
cgcccagcct gagcggccgc agcagcgccg cctcgtcccc cgccgccggc cgctcgcccg   1860
ccgaccaccg cggctacgcc agcctgcgcg ccgcctcgcc cgccccgtcc agcgcgccct   1920
cgcacgcgtc ctcctcggcc tcgtcccact cctcctcttc ctcctcctcg ggctcctcgt   1980
cctccgacga cgagttcgaa gacgacctgc tcgacctgaa ccccagctca aactttgaga   2040
gcatgtccct gggcagcttc agttcgtcgt cggcgctcga ccgggacctg gattttaact   2100
tcgagcccgg ctccggctcg cacttcgagt tcccggacta ctgcacgccc gaggtgagcg   2160
agatgatctc gggagactgg ctcgagtcca gcatctccaa cctggttttc acctactgaa   2220
gggcgcgcag gcagggagaa gggccggggg gggtaggaga ggagaaaaaa aaagtgaaaa   2280
aaagaaacga aaaggacaga cgaagagttt aagagaaaaa gggaaaaaag aaagaaaaag   2340
taagcagggc tggcttcgcc cgcgttctcg tcgtcggatc aaggagcgcg gcggcgtttt   2400
ggacccgcgc tcccatcccc caccttcccg ggccggggac ccactctgcc cagccggagg   2460
gacgcggagg aggaagaggg tagacagggg cgacctgtga ttgttgttat tgatgttgtt   2520
gttgatggca aaaaaaaaaa agcgactcg agtttgctcc cctttgcttg aagagacccc   2580 ctccccccttc caacgagctt ccggacttgt ctgcacccc agcaagaagg cgagttagtt   2640
ttctagagac ttgaaggagt ctccccctte ctgcatcacc accttggttt tgttttattt   2700
tgcttcttgg tcaagaaagg aggggagaac ccagcgcacc cctccccccc ttttttaaa   2760 cgcgtgatga agacagaagg ctccggggtg acgaatttgg ccgatggcag atgttttggg   2820
ggaacgccgg gactgagaga ctccacgcag gcgaattccc gtttgggct tttttttcct   2880 ccctctttc cccttgcccc ctctgcagcc ggaggaggag atgttgaggg gaggaggcca   2940
gccagtgtga ccggcgctag gaaatgaccc gagaaccccg ttggaagcgc agcagcggga   3000
gctaggggcg ggggcggagg aggacacgaa ctggaagggg gttcacggtc aaactgaaat   3060
ggatttgcac gttggggagc tggcggcggc ggctgctggg cctccgcctt cttttctacg   3120
tgaaatcagt gaggtgagac ttcccagacc ccggaggcgt ggaggagagg agactgtttg   3180
atgtggtaca ggggcagtca gtggagggcg agtggtttcg aaaaaaaa aagaaaaaa   3240 gaaaaaaaaa gaaaaaaaaa agatttttt cttctcttaa tcggaatcgt gatggtgttg   3300
gattatttca atggtggggt taatatagca tgttatcctg tctatctttt aaagatttct   3360
gtataagact gttgagcagt ttttaaaata gtgtaggata atataaaaag cagatagatg   3420
gcgctatgtt tgattcctac aacgaaatta tcaccagctt ttttcattc ttaactcttt   3480 aaaggattca aacgcaactc aaatctgtgc tggactttaa aaaacaatt caggaccaaa   3540 ttttttctca gtgtgtgtgt ttattcctta taggtgtaaa tgagaagacg tgttttttc   3600
```

-continued

| | | |
|---|---|---|
| cttcaccgat gctccatcct cgtatttctt tttccttgta aatgtaatca gatgccattt | 3660 |
| tatatgtgga cgtatttata ctggccaaac atattttttc ttttgtccct ttttttcttt | 3720 |
| cctttcttt tacttccttt atttcttat ccttcctt tccttttttt cttttttttt | 3780 |
| tcttttttt ttttttttt tggtagttgt tgttacccac gccatttac gtctccttca | 3840 |
| ctgaagggct agagttttaa cttttaattt tttatattta aatgtagact tttgacactt | 3900 |
| ttaaaaaaca aaaaagaca agagagatga aaacgtttga ttattttctc agtgtatttt | 3960 |
| tgtaaaaaat atataaaggg ggtgttaatc ggtgtaaatc gctgtttgga tttcctgatt | 4020 |
| ttataacagg gcggctggtt aatatctcac acagtttaaa aaatcagccc ctaatttctc | 4080 |
| catgtttaca cttcaatctg caggcttctt aaagtgacag tatcccttaa cctgccacca | 4140 |
| gtgtccaccc tccggccccc gtcttgtaaa aaggggagga gaattagcca aacactgtaa | 4200 |
| gcttttaaga aaaacaaagt tttaaacgaa atactgctct gtccagaggc tttaaaactg | 4260 |
| gtgcaattac agcaaaaagg gattctgtag ctttaacttg taaaccacat ctttttttgca | 4320 |
| cttttttat aagcaaaaac gtgccgttta aaccactgga tctatctaaa tgccgatttg | 4380 |
| agttcgcgac actatgtact gcgtttttca ttcttgtatt tgactattta atcctttcta | 4440 |
| cttgtcgcta aatataattg ttttagtctt atggcatgat gatagcatat gtgttcaggt | 4500 |
| ttatagctgt tgtgtttaaa aattgaaaaa agtggaaaac atctttgtac atttaagtct | 4560 |
| gtattataat aagcaaaaag attgtgtgta tgtatgttta atataacatg acaggcacta | 4620 |
| ggacgtctgc cttttaagg cagttccgtt aagggttttt gttttaaac ttttttttgc | 4680 |
| catccatcct gtgcaatatg ccgtgtagaa tatttgtctt aaaattcaag gccacaaaaa | 4740 |
| caatgtttgg gggaaaaaaa agaaaaaatc atgccagcta atcatgtcaa gttcactgcc | 4800 |
| tgtcagattg ttgatatata ccttctgtaa ataacttttt ttgagaagga aataaaatca | 4860 |
| gctggaactg aaccctaaaa aaaaaaaaaa aaaaaaaaaa aaaaaaaaaa aa | 4912 |

<210> SEQ ID NO 11
<211> LENGTH: 4045
<212> TYPE: DNA
<213> ORGANISM: Homo sapiens

<400> SEQUENCE: 11

| | | |
|---|---|---|
| gcagccagag ctcagcaggg ccctggagag atggccacgg tcccagcacc ggggaggact | 60 |
| ggagagcgcg cgctgccacc gccccatgtc tcagccaggg cttccttcct cggctccacc | 120 |
| ctgtggatgt aatggcggcc cctgctctgt cctggcgtct gccctcctc atcctcctcc | 180 |
| tgccctggc tacctcttgg gcatctgcag cggtgaatgg cacttcccag ttcacatgct | 240 |
| tctacaactc gagagccaac atctcctgtg tctggagcca agatgggct ctgcaggaca | 300 |
| cttcctgcca agtccatgcc tggccggaca acggcggtg gaaccaaacc tgtgagctgc | 360 |
| tccccgtgag tcaagcatcc tgggcctgca acctgatcct cggagcccca gattctcaga | 420 |
| aactgaccac agttgacatc gtcaccctga gggtgctgtg ccgtgagggg gtgcgatgga | 480 |
| gggtgatggc catccaggac ttcaagcccc ttgagaacct tcgcctgatg ccccccatct | 540 |
| ccctccaagt tgtccacgtg gagacccaca tgcaacat aagctgggaa atctcccaag | 600 |
| cctcccacta ctttgaaaga cacctggagt tcgaggcccg gacgctgtcc ccaggccaca | 660 |
| cctgggagga ggcccccctg ctgactctca agcagaagca ggaatggatc tgcctggaga | 720 |
| cgctcacccc agacacccag tatgagtttc aggtgcgggt caagcctctg caaggcgagt | 780 |
| tcacgaccctg gagcccctgg agccagcccc tggccttcag gacaaagcct gcagcccttg | 840 |

```
ggaaggacac cattccgtgg ctcggccacc tcctcgtggg cctcagcggg gcttttggct    900
tcatcatctt agtgtacttg ctgatcaact gcaggaacac cgggccatgg ctgaagaagg    960
tcctgaagtg taacacccca gacccctcga agttcttttc ccagctgagc tcagagcatg   1020
gaggagacgt ccagaagtgg ctctcttcgc ccttcccctc atcgtccttc agccctggcg   1080
gcctggcacc tgagatctcg ccactagaag tgctggagag ggacaaggtg acgcagctgc   1140
tcctgcagca ggacaaggtg cctgagcccg catccttaag cagcaaccac tcgctgacca   1200
gctgcttcac caaccagggt tacttcttct tccacctccc ggatgccttg agatagagg    1260
cctgccaggt gtactttact tacgacccct actcagagga agaccctgat gagggtgtgg   1320
ccggggcacc cacagggtct tcccccaac  ccctgcagcc tctgtcaggg gaggacgacg   1380
cctactgcac cttcccctcc agggatgacc tgctgctctt ctcccccagt ctcctcggtg   1440
gccccagccc cccaagcact gcccctgggg gcagtggggc cggtgaagag aggatgcccc   1500
cttctttgca agaaagagtc cccagagact gggaccccca gccctgggg  cctcccaccc   1560
caggagtccc agacctggtg gattttcagc caccccctga gctggtgctg cgagaggctg   1620
gggaggaggt ccctgacgct ggccccaggg agggagtcag tttcccctgg tccaggcctc   1680
ctgggcaggg ggagttcagg gcccttaatg ctcgcctgcc cctgaacact gatgcctact   1740
tgtccctcca agaactccag ggtcaggacc caactcactt ggtgtagaca gatgccagg    1800
gtgggaggca ggcagctgcc tgctctgcgc cgagcctcag aaggaccctg ttgagggtcc   1860
tcagtccact gctgaggaca ctcagtgtcc agttgcagct ggacttctcc acccggatgg   1920
cccccaccca gtcctgcaca cttggtccat ccatttccaa acctcactg  ctgctcccgg   1980
gtcctgctgc ccgagccagg aactgtgtgt gttgcagggg ggcagtaact ccccaactcc   2040
ctcgttaatc acaggatccc acgaatttag gctcagaagc atcgctcctc tccagccctg   2100
cagctattca ccaatatcag tcctcgcggc tctccagggc tccctgccct gacctcttcc   2160
ctgggttttc tgccccagcc tcctccttcc ctccctccc  cgtccacagg gcagcctgag   2220
cgtgctttcc aaaacccaaa tatggccacg ctcccctcg  gttcaaaacc ttgcacaggt   2280
cccactgccc tcagccccac ttctcagcct ggtacttgta cctccggtgt cgtgtgggga   2340
catcccttc  tgcaatcctc cctaccgtcc tcctgagcca tcagagctc  cctcacaccc   2400
cctctgttgc acatgctatt ccctgggct  gctgtgcgct cccctcatc  taggtgacaa   2460
acttccctga ctcttcaagt gccggttttg cttctcctgg agggaagcac tgcctcccctt  2520
aatctgccag aaacttctag cgtcagtgct ggagggagaa gctgtcaggg acccagggcg   2580
cctggagaaa gaggccctgt tactattcct ttgggatctc tgaggcctca gagtgcttgg   2640
ctgctgtatc tttaatgctg gggcccaagt aagggcacag atcccccac  aaagtggatg   2700
cctgctgcat cttcccacag tggcttcaca gacccacaag agaagctgat ggggagtaaa   2760
ccctggagtc cgaggcccag gcagcagccc cgcctagtgg tgggccctga tgctgccagg   2820
cctgggacct cccactgccc cctccactgg aggggtctcc tctgcagctc agggactggc   2880
acactggcct ccagaagggc agctccacag ggcagggcct cattattttt cactgcccca   2940
gacacagtgc ccaacacccc gtcgtatacc ctggatgaac gaattaatta cctggcacca   3000
cctcgtctgg gctccctgcg cctgacattc acacagagag gcagagtccc gtgcccatta   3060
ggtctggcat gccccctcct gcaagggggct caacccccta ccccgacccc tcacgtatc    3120
tttcctaggc agatcacgtt gcaatggctc aaacaacatt ccaccccagc aggacagtga   3180
```

| | |
|---|---|
| ccccagtccc agctaactct gacctgggag ccctcaggca cctgcactta caggccttgc | 3240 |
| tcacagctga ttgggcacct gaccacacgc ccccacaggc tctgaccagc agcctatgag | 3300 |
| ggggtttggc accaagctct gtccaatcag gtaggctggg cctgaactag ccaatcagat | 3360 |
| caactctgtc ttgggcgttt gaactcaggg agggaggccc ttgggagcag gtgcttgtgg | 3420 |
| acaaggctcc acaagcgttg agccttggaa aggtagacaa gcgttgagcc actaagcaga | 3480 |
| ggaccttggg ttcccaatac aaaaatacct actgctgaga gggctgctga ccatttggtc | 3540 |
| aggattcctg ttgcctttat atccaaaata aactccccectt tcttgaggtt gtctgagtct | 3600 |
| tgggtctatg ccttgaaaaa agctgaatta ttggacagtc tcacctcctg ccatagggtc | 3660 |
| ctgaatgttt cagaccacaa ggggctccac acctttgctg tgtgttctgg ggcaacctac | 3720 |
| taatcctctc tgcaagtcgg tctccttatc cccccaaatg gaaattgtat ttgccttctc | 3780 |
| cactttggga ggctcccact tcttggga ggttacatttt ttaagtctta atcatttgtg | 3840 |
| acatatgtat ctatacatcc gtatctttta atgatccgtg tgtaccatct ttgtgattat | 3900 |
| ttccttaata tttttttcttt aagtcagttc attttcgttg aaatacatttt atttaaagaa | 3960 |
| aaatctttgt tactctgtaa atgaaaaaac ccattttcgc tataaataaa aggtaactgt | 4020 |
| acaaaataag tacaatgcaa caaaa | 4045 |

<210> SEQ ID NO 12
<211> LENGTH: 3033
<212> TYPE: DNA
<213> ORGANISM: Homo sapiens

<400> SEQUENCE: 12

| | |
|---|---|
| gcgggggcgc gtcggggctg gagccggagc gcgccgggcg ctgggcgcag cgagcgagag | 60 |
| cgcggcggcc gcgggctccg gcgagggaca gacgcaccga tcgccggagg gacagacaca | 120 |
| cgaccacgcg gcgccaccgc ccacgcctcc acccaccggc gcccaagtcc tccccgcgcc | 180 |
| gcctcctctg tatggcacaa actttcctcc cgggacggaa cacgctgcct cagggagccc | 240 |
| gcgaccgcgc cttctcctcc gccggtccca tacgctgctg aaatggggttg cggattgaac | 300 |
| aagttagaga aacgtgatga aaaacggcct gggaatattt attcaacttt gaagaggcct | 360 |
| caggtggaaa ccaagataga tgtgtcctat gaataccgct tcctggagtt cacgactctg | 420 |
| agtgctgcgg agctccctgg gtcctcagca gtgaggctgg cctccctgcg tgacctgccc | 480 |
| gcccagctcc tggagctgta ccagcagggc ttctcgctgg cggccctgca ccccttcgtg | 540 |
| cagcccaccc atgagcggga gaagacgccc tggagcacat cttttagagc catcctgatc | 600 |
| aagaaaaccg acagatctca gaaaactgat cttcacaatg aaggctacat cttggaatta | 660 |
| gattgctgtt cctccttaga ccacccgaca gaccagaaac tcatcccaga gttcattaag | 720 |
| aagatccagg aggctgcaag ccagggcctg aaattcgttg gtgttatacc tcagtaccat | 780 |
| tcctctgtga actcggcagg cagcagtgct ccggtgtcta ctgccaacag caccgaggat | 840 |
| gccagagatg caaaaaacgc acgtggggat cacgcgtcac tggagaatga aaaccgggg | 900 |
| actggggatg tgtgcagtgc tccggctggg agaaaccaaa gcccagagcc agctcaggc | 960 |
| cccgagggga aggtgcccct cgccaagcag cccagctcac cctccggaga gggagatggt | 1020 |
| ggagaacttt caccacaggg ggtgagcaag acactggatg gaccggagag caacccttg | 1080 |
| gaggtgcatg aagagccact ctcagggaaa atggagatct tcacccttttt caacaaaccg | 1140 |
| aagagccatc agaagtgccg gcaatactac cctgtcacca ttcctctcca tgtctccaag | 1200 |
| aatggccaga cagtgagcgg tttggacgcc aactggttag agcacatgag cgaccacttc | 1260 |

```
cggaaaggag gcatgctggt gaacgcagtc ttctaccttg aaatagtgaa tgattcctta    1320
catggcttga cagatggagt attcatcttt gaagctgttt ccacagaaga tagcaaaacc    1380
atacagggct atgatgctat tgtggttgaa caatggacag tcctggaagg tgtcgaagtg    1440
cagacagact acgtgcccct gctgaactcg ctggcggcct atggctggca gctcacctgt    1500
gtgctaccaa ctcccgtcgt caagactacc agcgagggga gtgtatccac caagcagatt    1560
gtctttcttc agagaccttg tctacctcag aaaatcaaga agaaggaatc gaagtttcag    1620
tggcgattct ccagagaaga aatgcacaac aggcagatga ggaaatcaaa aggtaaactc    1680
agtgccagag acaaacaaca agcagaagaa aatgagaaga acttagaaga ccagtcttcc    1740
aaagctggag acatgggaaa ctgtgtttca ggacagcagc aggagggtgg agtctccgag    1800
gagatgaagg gccctgtcca agaggacaag ggagaacagc tgtcccctgg tggcctgctg    1860
tgtggggtgg gtgtggaggg tgaggctgtg cagaatggtc ctgccagcca cagcagggcc    1920
ctggtgggga tttgcactgg gcactccaat cctggagagg atgccaggga cggggatgct    1980
gaggaagtca gagagcttgg tacggttgaa gaaaactgag tcttgggcaa tttgtgctaa    2040
aactaggtga gttgccaaac ccaaggcatc ttaccaacag ctggtttggg ggctggtttc    2100
cctggtgttg tgtgttacct accctttggc ttggcttgac ctctccttgt gagctcacct    2160
gagccctccc agggccaggt tcctgacagt gttggttttt gcacatccac tggaaaggtg    2220
tcattaatga cccagtgtta gaatgcaaga ggtcaggtta ttctagccct catggctgaa    2280
ggcccagtcc tggctccacc actcctccag ccagagggtc tggaccatcc agtgcctgtc    2340
ctcgccacag ggcctccagg gagcattcgg gtcaaatcca tggacaccct gggctacaaa    2400
ccaaggctgc tgttcatccc acatcgtgtg gggcagtgtc catcccctgc agctacttgg    2460
tgacttaaca actccaggag ccctgtcagc tgccctcctc cacctaaacc ccttcgactc    2520
ttctgctttg acaaagaaaa tgacattggg gaggggaggt gctccgcctc ccagcttttc    2580
tcaaaatagt cctatagata ctggtaatct ggaaatgaag aagtaattct gtctctgcac    2640
ctacttttgc agaatgttca aggaagtatt ctgtgttagt attaatgcca aaaagttgtt    2700
tttaaaggtt ttgtactcag cacatcatac aaaccacatt acttctgtca cttcagggca    2760
tcgggactgg ctggcgccct tgttatgtgc tattttaatc agtgtaacat tggtcaagtt    2820
gttacccatg tatgctgtgt ttatcatgtg tatatcgtcc agaaagtatt aaggctttag    2880
gtagatgcaa ctggcgaacc ttggagaggg aatgctgatt gtcttgacca aacccacagc    2940
ctgtctcttc tcttgtttag ttacttacgg caataaatca tctatgagtt agtgcaccgt    3000
gaaaaaaaaa aaaaaaaaa aaaaaaaaaa aaa                                  3033
```

<210> SEQ ID NO 13
<211> LENGTH: 3146
<212> TYPE: DNA
<213> ORGANISM: Homo sapiens

<400> SEQUENCE: 13

```
gccgcaaccc gtcccggagg tgtcctgtct cctgtcgccg ccgccgccgc caccaccgct      60
gccactgccg ccctgccggg gccatgttcg ctctgggctt gccttcttg gtgctcttgg     120 tggcctcggt cgagagccat ctgggggttc tggggcccaa gaacgtctcg cagaaagacg     180
ccgagtttga gcgcacctac gtggacgagg tcaacagcga gctggtcaac atctacacct     240
tcaaccatac tgtgacccgc aacaggacag agggcgtgcg tgtgtctgtg aacgtcctga     300
```

```
acaagcagaa gggggcgccg ttgctgtttg tggtccgcca aaggaggct gtggtgtcct    360
tccaggtgcc cctaatcctg cgagggatgt ttcagcgcaa gtacctctac caaaaagtgg   420
aacgaaccct gtgtcagccc cccaccaaga atgagtcgga gattcagttc ttctacgtgg   480
atgtgtccac cctgtcacca gtcaacacca cataccagct ccgggtcagc cgcatggacg   540
attttgtgct caggactggg gagcagttca gcttcaatac cacagcagca cagccccagt   600
acttcaagta tgagttccct gaaggcgtgg actcggtaat tgtcaaggtg acctccaaca   660
aggccttccc ctgctcagtc atctccattc aggatgtgct gtgtcctgtc tatgacctgg   720
acaacaacgt agccttcatc ggcatgtacc agacgatgac caagaaggcg ccatcaccg    780
tacagcgcaa agacttcccc agcaacagct tttatgtggt ggtggtggtg aagaccgaag   840
accaagcctg cgggggctcc ctgcctttct accccttcgc agaagatgaa ccggtcgatc   900
aagggcaccg ccagaaaacc ctgtcagtgc tggtgtctca agcagtcacg tctgaggcat   960
acgtcagtgg gatgctcttt tgcctgggta tatttctctc cttttacctg ctgaccgtcc  1020
tcctggcctg ctgggagaac tggaggcaga agaagaagac cctgctggtg ccattgacc   1080
gagcctgccc agaaagcggt caccctcgag tcctggctga ttcttttcct ggcagttccc  1140
cttatgaggg ttacaactat ggctcctttg agaatgtttc tggatctacc gatggtctgg  1200
ttgacacgcg ctggcactgg gacctctctt acggttacca ggggcacgac cagttcaagc  1260
ggcgcctccc ctctgccag atgcggcagc tgtgcattgc catgggccgc tcctttgaac   1320
ctgtaggtac tcggccccga gtggactcca tgagctctgt ggaggaggat gactacgaca  1380
cattgaccga catcgattcc gacaagaatg tcattcgcac caagcaatac ctctatgtgg  1440
ctgacctggc acggaaggac aagcgtgttc tgcggaaaaa gtaccagatc tacttctgga  1500
acattgccac cattgctgtc ttctatgccc ttcctgtggt gcagctggtg atcacctacc  1560
agacggtggt gaatgtcaca gggaatcagg acatctgcta ctacaacttc ctctgcgccc  1620
acccactggg caatctcagc gccttcaaca acatcctcag caacctgggg tacatcctgc  1680
tggggctgct tttcctgctc atcatcctgc aacgggagat caaccacaac cgggccctgc  1740
tgcgcaatga cctctgtgcc ctggaatgtg ggatccccaa acactttggg cttttctacg  1800
ccatgggcac agccctgatg atggaggggc tgctcagtgc ttgctatcat gtgtgcccca  1860
actataccaa tttccagttt gacacatcgt tcatgtacat gatcgccgga ctctgcatgc  1920
tgaagctcta ccagaagcgg cacccggaca tcaacgccag cgcctacagt gcctacgcct  1980
gcctggccat tgtcatcttc ttctctgtgc tgggcgtggt cttttggcaaa gggaacacgg  2040
cgttctggat cgtcttctcc atcattcaca tcatcgccac cctgctcctc agcacgcagc  2100
tctattacat gggccggtgg aaactggact cggggatctt ccgccgcatc ctccacgtgc  2160
tctacacaga ctgcatccgg cagtgcagcg ggccgctcta cgtggaccgc atggtgctgc  2220
tggtcatggg caacgtcatc aactggtcgc tggctgccta tgggcttatc atgcgccccca  2280
atgatttcgc ttcctacttg ttggccattg gcatctgcaa cctgctcctt tacttcgcct  2340
tctacatcat catgaagctc cggagtgggg agaggatcaa gctcatcccc ctgctctgca  2400
tcgtttgcac ctccgtggtc tggggcttcg cgctcttctt cttcttccag ggactcagca  2460
cctggcagaa aaccctgca gagtcgaggg agcacaaccg ggactgcatc ctcctcgact  2520
tctttgacga ccacgacatc tggcacttcc tctcctccat cgccatgttc gggtccttcc  2580
tggtaagcgg gcctcccggc gcagcgttga ggataacgtg aaaggtagca gctgcctcct  2640
tctctgtgag ctgatctggc gtccacaccc caggtgttag ctgacactgg atgacgacct  2700
```

| | |
|---|---|
| ggatacttag aaagggggctt caggaaggga tgtgctgttt ccctctacgt gcccagtcct | 2760 |
| agcctcgctc taggacccag ggctggcttc taagtttccg tccagtcttc aggcaagttc | 2820 |
| tgtgttagtc atgcacacac atacctatga aaccttgaag tttacaaaga attgccccag | 2880 |
| ctctgggcac cctggccacc ctggtccttg atccccttc gtcccacctg gtccacccca | 2940 |
| gatgctgagg atgggggagc tcaggcgggg cctctgcttt ggggatggga atgtgttttt | 3000 |
| ctcccaaact tgttttata gctctgcttg aagggctggg agatgaggtg ggtctggatc | 3060 |
| ttttctcaga gcgtctccat gctatggttg catttccgtt ttctatgaat gaatttgcat | 3120 |
| acaataacca accagactca gtaaaa | 3146 |

<210> SEQ ID NO 14
<211> LENGTH: 1558
<212> TYPE: DNA
<213> ORGANISM: Homo sapiens

<400> SEQUENCE: 14

| | |
|---|---|
| cggaggagag cgcaggagga aacagtaccg gctggaggcc ggtcttgcag gagcggggga | 60 |
| ctgctggggg cggggcttgg tggtgaccgc tggcggggcg gggcctgggg ctcagagggg | 120 |
| tgggctttgg agatcagagg gtcgacgctg cttcgttgcc tggactctgg tttccgccct | 180 |
| ggagcaagcc ggggcctggt cggcagctgg gccgccatgg agtccacgct gggcgcgggc | 240 |
| atcgtgatag ccgaggcgct acagaaccag ctagcctggc tggagaacgt gtggctctgg | 300 |
| atcacctttc tgggcgatcc caagatcctc tttctgttct acttccccgc ggcctactac | 360 |
| gcctcccgcc gtgtgggcat cgcggtgctc tggatcagcc tcatcaccga gtggctcaac | 420 |
| ctcatcttca gtggtttct ttttggagac aggccctttt ggtgggtcca tgagtctggt | 480 |
| tactacagcc aggctccagc ccaggttcac cagttcccct cttcttgtga gactggtcca | 540 |
| ggcagccctt ctggacactg catgatcaca ggagcagccc tctggcccat aatgacggcc | 600 |
| ctgtcttcgc aggtggccac tcgggcccgc agccgctggg taagggtgat gcctagcctg | 660 |
| gcttattgca ccttccttt ggcggttggc ttgtcgcgaa tcttcatctt agcacatttc | 720 |
| cctcaccagg tgctggctgg cctaataact ggcgctgtcc tgggctggct gatgactccc | 780 |
| cgagtgccta tggagcggga gctaagcttc tatgggttga ctgcactggc cctcatgcta | 840 |
| ggcaccagcc tcatctattg gaccctcttt acactgggcc tggatctttc ttggtccatc | 900 |
| agcctagcct tcaagtggtg tgagcggcct gagtggatac acgtggatag ccggcccttt | 960 |
| gcctccctga ccgtgactcc aggggctgcc ctgggcctgg gcattgcctt gcactctccc | 1020 |
| tgctatgccc aggtgcgtcg ggcacagctg ggaaatggcc agaagatagc ctgccttgtg | 1080 |
| ctggccatgg ggctgctggg cccccctggac tggctgggcc accccctca gatcagcctc | 1140 |
| ttctacattt tcaatttcct caagtacacc ctctggccat gcctagtcct ggccctcgtg | 1200 |
| ccctgggcag tgcacatgtt cagtgccag gaagcaccgc ccatccactc ttcctgactt | 1260 |
| cttgtgtgcc tccctttcct ttccctccca caaagccaac actctgtgac caccacactc | 1320 |
| caggaggcag ccccatcccc ttccagcccc taagtaggcc ctcccctccc taaatctgct | 1380 |
| tccgcaccac ctggtcttag ccccaaagat gggccttctc tctcccagat aagttggtcc | 1440 |
| tccctctgcc tttcctctca gccccaaa gagcaaaggc aacagcaaga ccagcgggtt | 1500 |
| cttgcaacac tgtgagggc agccaggcg gccccaataa agcccttgaa tactttga | 1558 |

<210> SEQ ID NO 15

<211> LENGTH: 5388
<212> TYPE: DNA
<213> ORGANISM: Homo sapiens

<400> SEQUENCE: 15

```
gcaacagcgg cggcggccgc ggcggctggc cggactcagg tgtttcggac gctattgccc      60
ttcgcgccag ccgtcgagtg ggcagcagcg ggactcagcc gggcgccagg ttcctgccag     120
gcagcgccgg gaagcgcggg cggccgagaa ctccttcctg ctacttcgcc cagcgccgct     180
gcttcggctt cccagcgaag tgggagacct tcctccctgt ttgcagacgt ccgtgggaga     240
cccttatttt ttccaccgct aaggttaaga gattctggaa tagaagcgtc gaaggagatc     300
aagtgaacct tctacaactc ctcggatgtc gccagtctcc ctttcggggc ggaagactac     360
gtttgagcat ctcactgagg tgcaggaatg aagaaccca ccttgcagct tttctgcagt     420
gtggcttgcc tgatctaccc ctaggaatga agaggaggct tgtaataatc cgatgaagta     480
cagatgttga agaggatatc gcaggaccta aacttgtgat cgtttggggg aggtcacaca     540
cgtttctgag tgggaatgga tgggcgtgaa tgacgtgccc tcttaaaaag cacaacagtc     600
ctttaagagg agcaaaattg agttttccca ttttggccaa gattttgaag acagttcaat     660
gtattctaca tttgacataa gatgagaact ttctaaagta ttctctccaa gagcgtaaac     720
gatgactacc ccagccctgc tgcccctctc tggacgtagg ataccacctc tgaacctggg     780
gccgccttcc ttcccacatc acagggctac cttgagactt tctgagaagt ttattcttct     840
ccttattctt agtgccttca tcactctgtg ttttggggca ttcttttccc ttccagactc     900
ttcaaaacac aaacgctttg atttgggttt agaagatgtg ttaattccac atgtagatgc     960
cggtaaaggg gctaaaaacc ccggagtctt cctgatccat ggacccgatg aacatagaca    1020
cagggaagag gaagaacgtc tgagaaataa aattcgagct gatcatgaga aggccttgga    1080
agaagcaaaa gaaaaattaa gaaagtcaag agaggaaatt cgagcagaaa ttcagacaga    1140
gaaaaataag gtagtccaag aaatgaagat aaaagagaac aagccactgc caccagtccc    1200
tattcccaac cttgtaggaa tacgtggtgg agacccagaa gataatgaca taagagagaa    1260
aagggaaaaa attaaagaga tgatgaaaca tgcttgggat aactatagga catatggggtg    1320
gggacataat gaactcagac ctattgcaag gaaaggacac tcccctaaca tatttggaag    1380
ttcacaaatg ggtgctacca tagtagatgc tttggatacc ctttatatca tgggacttca    1440
tgatgaattc ctagatgggc aaagatggat tgaagacaac cttgatttca gtgtgaattc    1500
agaggtgtct gtgtttgaag tcaacattcg atttattgga ggcctacttg cagcatatta    1560
cctatcagga gaggagatat tcaagattaa agcagtgcaa ttggctgaga aactccttcc    1620
tgcctttaac acacctactg ggattccttg ggcaatggtg aatttgaaaa gtggagtagg    1680
gcgaaactgg ggctgggcat ctgcaggtag cagcattctg gctgaatttg gtacactaca    1740
tatggagttc atccacctca gctacttgac aggggacctg acttactaca aaaaggttat    1800
gcacattcgg aaactacttc agaaaatgga tcgtccaaat ggtctttatc caaattattt    1860
gaaccccaga acagggcgct ggggtcagta tcatacatct gtcggtggcc tgggagacag    1920
tttttatgaa tacttactga aagcatggtt gatgtcagat aaaacagacc atgaggcaag    1980
aaagatgtat gatgatgcta ttgaggctat agaaaaacat cttattaaga agtctcgtgg    2040
aggtctttacc tttattggag aatggaagaa tgggcacttg gaaaaaaaga tggggcattt    2100
ggcctgcttt gctgggggaa tgtttgcact aggagcagat ggttccagag cagataaagc    2160
tggtcattat ttagagctag ggcagaaaat tgcacgtact tgtcatgagt catatgacag    2220
```

```
aactgcatta aagctaggtc ctgaatcatt caagtttgat ggtgcagtgg aggctgtggc    2280
tgtccggcag gctgaaaagt attatatcct ccgtccagaa gtaattgaaa cctattggta    2340
cctatggcga ttcactcacg atccaagata caggcagtgg ggctgggaag cagcactggc    2400
cattgaaaag tattgccgag ttaatggtgg gttttctgga gtcaaagatg tatattcctc    2460
tactcctaca catgatgatg tacagcagag cttttttctt gctgaaacat taaaatattt    2520
gtatctgctg ttctccggtg atgacctttt acctttagac cactgggtgt ttaatacaga    2580
ggctcaccct ctgcctgtgt tacatttagc caacaccaca ctttcaggta atcctgctgt    2640
tcgatgaaag cagttccaga aggaccattc tcacctgtgt tttgtttaca tggaccacta    2700
cagaaattag tttgaagggg cggcttttga aaacctggac ctctatgtca acatgacagg    2760
gtgaaactat tcccctaag actgttcaac ttgtagatac atcaactttg aaattattcc     2820
attttatacc tgaccaaaac atgttctgat atgtgtagga cagagacctg atgtgctttt    2880
gatcgttaat gaggtggtca catgagaaat gataccctgtt actactgtat tgtttttaga   2940
gtcctgaagt ctggaggcta gacttcctga agcaagtca agaatataga gcaccttgca     3000
ggagttcaag atggcctttg gaaccaatta tgtatttgtt tcctcctaca gtggagcagc    3060
attcaaatca aatatttaca tattgcttat cacttttct ccattttaat aatggaatga     3120
actaaaataa acaagaacaa aagaatagta taattatatc agtaacaaga agactcaaaa    3180
aagaaacagg agtacctatc cctatctgaa ttttcaagtt ccccattgga tgaccagact    3240
ggcaaccatt tcaaatccca gtctatttca ttgaaatttc ttggttaagt ttaattttct    3300
ctgggggcat gatctcacaa agaatactca agtctttttc ttcttatgga atcatcgaaa    3360 ctgctatta tcataatcac cacttatgag cctgggtttg ggattttgtg catgtagttc     3420
agtctagtgt tggtagcatg acagaaagtg gggaaaatgc cgcagtttgt tgccttgaaa    3480
cctaagagca atccttggtt tgttgctac attattttc cagaccaaca catctaccaa      3540
gtaaatttta ttcactttaa tttcataata aagttagtag agtcactcaa cttacaactt    3600
tatttatgtg gcttggcaaa atcactata aggcagctct aaatttgcct tgataagcta     3660
aataaattac ttttataact tactaaagca gaacaaacag tgaaactttc taaaatattc    3720
tatctggaat agggacaggg gatcttttat ttataatctc atcagatgag tgagttgttc    3780
acagatattt tatgtttttt taattttctc caagaatatt tatagaattc caagaatca    3840 gaatagtttc aaaataattt tcagtgataa aagagtgttg taattaatca tattacacta    3900
aaattgggat acatctaagg aactttatct tactatcagt aggttttgca ttgatatttc    3960
tttttaaata aactactagt tctttatatt ttgacaaaaa gaacttaaat tttatcagga    4020
actgtaagat aaatatctag tgcttataaa ttttctgtcc ttaaatttat gtgacagtgc    4080
aagatacttt tgctcttttc atttaatata ggcatcttcc attgacatta ataaaactta    4140
gaaacagtat aattagtata acatttactc tgaatttgaa gatttcctga aacaaagttt    4200
gtacaagaag cccaccttgg aattctgaag gcttattttc ttgtttgata agcttttctt    4260
ttaaacttag gttttaagtt ggggaaagac ttaattaact aatatagtat tttctaaggt    4320
tgatcatctt ataccacgaa tcgttaattt tgacagttct actgatccgt aaatgataac    4380
cactgcaaat ttttttcagta taaaattttt cactgcaaaa aaatttcagt agaaaataag    4440
gatgcagggc cagttacaat agtccttaag agagttaaat tatagcacat gttttgacat    4500
tgtaatatct tttactactt gaacatttaa atttctaaat gagaaaggta tatatattac    4560
```

| | |
|---|---|
| tgtaactgta gaagggaaaa gggaaagtat ttggttctaa aaaatgttag ccttcctcgt | 4620 |
| aaaagtagca caagcccact tatgaatcac tgagaaaaag tgaaaaactt gagttggcaa | 4680 |
| agatgcagag cagcagtgca gatggcaatg aactctctga attctctttt accttattta | 4740 |
| gaagaatgca gagtaaaggg accttcttgg ttctgcagga acttctcaag ggatgaggag | 4800 |
| acagaaccc tacttccaag tgctctattt gtattaccca gatgactgaa gcttaagaga | 4860 |
| aggcagggaa gtatacaagc agagccagtt ctggtacaaa caagaatttt gacagggaca | 4920 |
| atggaagggt cttcttcacc actccttacc ttctatgtga tggaaagact agagcttata | 4980 |
| aaagtacttc catttttta ttctcctgaa taccaaaggc aattaaagtc agctacaaat | 5040 |
| gacttgccag tgtcatgttt tattttgtt atagattttt aaattatttc cttcaagatc | 5100 |
| aattcttatc ccatataatg cttagcttcc aagaatattc tttactttct tctgtctttt | 5160 |
| acagctcttt gcattttgta gaccttaata ctcaggttaa atattcattg catttataag | 5220 |
| atcttctgca aaaagcccag aaatggtcct tttcaggtgc ctcttcaaag agctgacacc | 5280 |
| ttaccttgtg cctttggcac aaatgtgcag aatagataca tcagttggtg cataatcgaa | 5340 |
| aaaaatagga attttgaaca ctgttcttcc ttctacattt atttctct | 5388 |

<210> SEQ ID NO 16
<211> LENGTH: 2678
<212> TYPE: DNA
<213> ORGANISM: Homo sapiens

<400> SEQUENCE: 16

| | |
|---|---|
| atgcgacccg accgcgctga ggctccagga ccgcccgcca tggctgcagg aggtcccggc | 60 |
| gcggggtctg cggccccggt ctcctccaca tcctcccttc ccctggctgc tctcaacatg | 120 |
| cgagtgcggc gccgcctgtc tctgttcttg aacgtgcgga cacaggtggc ggccgactgg | 180 |
| accgcgctgg cggaggagat ggactttgag tacttggaga tccggcaact ggagacacaa | 240 |
| gcggaccca ctggcaggct gctggacgcc tggcagggac gccctggcgc tctctgtaggc | 300 |
| cgactgctcg agctgcttac caagctgggc gcgacgacg tgctgctgga gctgggaccc | 360 |
| agcattgagg aggattgcca aaagtatatc ttgaagcagc agcaggagga ggctgagaag | 420 |
| cctttacagg tggccgctgt agacagcagt gtcccacgga cagcagagct ggcgggcatc | 480 |
| accacacttg atgaccccct ggggcatatg cctgagcgtt tcgatgcctt catctgctat | 540 |
| tgccccagcg acatccagtt tgtgcaggag atgatccggc aactggaaca gacaaactat | 600 |
| cgactgaagt tgtgtgtgtc tgaccgcgat gtcctgcctg gcacctgtgt ctggtctatt | 660 |
| gctagtgagc tcatcgaaaa gaggtgccgc cggatggtgg tggttgtctc tgatgattac | 720 |
| ctgcagagca aggaatgtga cttccagacc aaatttgcac tcagcctctc tccaggtgcc | 780 |
| catcagaagc gactgatccc catcaagtac aaggcaatga agaaagagtt ccccagcatc | 840 |
| ctgaggttca tcactgtctg cgactacacc aaccctgca ccaaatcttg gttctggact | 900 |
| cgccttgcca aggccttgtc cctgccctga agactgttct gaggccctgg gtgtgtgtgt | 960 |
| atctgtctgc ctgtccatgt acttctgccc tgcctcctcc tttcgttgta ggaggaatct | 1020 |
| gtgctctact tacctctcaa ttcctggaga tgccaacttc acagacacgt ctgcagcagc | 1080 |
| tggacatcac atttcatgtc ctgcatggaa ccagtggctg tgagtggcat gtccacttgc | 1140 |
| tggattatca gccaggacac tatagaacag gaccagctga gactaagaag gaccagcaga | 1200 |
| gccagctcag ctctgagcca ttcacacatc ttcccctca gtttcctcac ttgaggagtg | 1260 |
| ggatggggag aacagagagt agctgtgttt gaatccctgt aggaaatggt gaagcatagc | 1320 |

| | |
|---|---:|
| tctgggtctc ctgggggaga ccaggcttgg ctgcgggaga gctggctgtt gctggactac | 1380 |
| atgctggcca ctgctgtgac cacgacactg ctggggcagc ttcttccaca gtgatgccta | 1440 |
| ctgatgcttc agtgcctctg cacaccgccc attccacttc ctccttcccc acagggcagg | 1500 |
| tggggaagca gtttggccca gcccaaggag accccatctt gagccttatt tcctaatggg | 1560 |
| tccacctctc atctgcatct ttcacacctc ccagcttctg cccaaccttc agcagtgaca | 1620 |
| agtccccaag agactcgcct gagcagcttg ggctgctttt catttccacc tgtcaggatg | 1680 |
| cctgtggtca tgctctcagc tccacctggc atgagaaggg atcctggcct ctggcatatt | 1740 |
| catcaagtat gagttctggg gatgagtcac tgtaatgatg tgagcaggga gccttcctcc | 1800 |
| ctgggccacc tgcagagagc tttcccacca actttgtacc ttgattgcct tacaaagtta | 1860 |
| tttgtttaca aacagcgacc atataaaagc ctcctgcccc aaagcttgtg ggcacatggg | 1920 |
| cacatacaga ctcacataca gacacacaca tatatgtaca gacatgtact ctcacacaca | 1980 |
| caggcaccag catacacacg ttttctagg tacagctccc aggaacagct aggtgggaaa | 2040 |
| gtcccatcac tgagggagcc taaccatgtc cctgaacaaa aattgggcac tcatctattc | 2100 |
| cttttctctt gtgtccctac tcattgaaac caaactctgg aaaggaccca atgtaccagt | 2160 |
| atttataccct ctaatgaagc acagagagag gaagagagct gcttaaactc acacaacaat | 2220 |
| gaactgcaga cacagctgtt ctctccctct ctccttccca gagcaattta actttaccc | 2280 |
| tcaggctgtc ctctggggag aaggtgccat ggtcttaggt gtctgtgccc caggacagac | 2340 |
| cctaggaccc taaatccaat agaaaatgca tatctttgct ccactttcag ccaggctgga | 2400 |
| gcaaggtacc ttttcttagg atcttgggag ggaatggatg cccctctctg catgatcttg | 2460 |
| ttgaggcatt tagctgccat gcacctgtcc ccctttaata ctgggcattt taaagccatc | 2520 |
| tcaagaggca tcttctacat gttttgtacg cattaaaata atttcaaaga tatctgagaa | 2580 |
| aagccgatat ttgccattct tcctatatcc tggaatatat cttgcatcct gagtttataa | 2640 |
| taataaaataa tattctacct tggaaaaaaa aaaaaaaa | 2678 |

<210> SEQ ID NO 17
<211> LENGTH: 950
<212> TYPE: DNA
<213> ORGANISM: Homo sapiens

<400> SEQUENCE: 17

| | |
|---|---:|
| gggaccttaa ttctctttcc catcttgcaa gatggcgggt gaaaaagttg agaagccaga | 60 |
| tactaaagag aagaaacccg aagccaagaa ggttgatgct ggtggcaagg tgaaaaaggg | 120 |
| taacctcaaa gctaaaaagc ccaagaaggg gaagccccat tgcagccgca accctgtcct | 180 |
| tgtcaggaga attggcaggt attcccgatc tgccatgtat tccagaaagg ccatgtacaa | 240 |
| gaggaagtac tcagccgcta atccaaggt tgaaaagaaa aagaaggaga aggttctcgc | 300 |
| aactgttaca aaaccagttg gtggtgacaa gaacggcgt acccgggtgg ttaaacttcg | 360 |
| caaaatgcct agatattatc ctactgaaga tgtgcctcga aagctgttga gccacggcaa | 420 |
| aaaaccttc agtcagcacg tgagaaaact gcgagccagc attacccccg ggaccattct | 480 |
| gatcatcctc actggacgcc acaggggcaa gagggtggtt ttcctgaagc agctggctag | 540 |
| tggcttatta cttgtgactg gacctctggt cctcaatcga gttcctctac gaagaacaca | 600 |
| ccagaaattt gtcattgcca cttcaaccaa atcgatatc agcaatgtaa aaatcccaaa | 660 |
| acatcttact gatgcttact tcaagaagaa gaagctgcgg aagcccagac accaggaagg | 720 |

```
tgagatcttc gacacagaaa aagagaaata tgagattacg gagcagcgca agattgatca      780
gaaagctgtg gactcacaaa ttttaccaaa aatcaaagct attcctcagc tccagggcta      840
cctgcgatct gtgtttgctc tgacgaatgg aatttatcct cacaaattgg tgttctaaat      900
gtcttaagaa cctaattaaa tagctgacta caaaaaaaaa aaaaaaaaa                  950

<210> SEQ ID NO 18
<211> LENGTH: 700
<212> TYPE: DNA
<213> ORGANISM: Homo sapiens

<400> SEQUENCE: 18
gcggcgtgag aagccatgag cagcaaagtc tctcgcgaca ccctgtacga ggcggtgcgg       60
gaagtcctgc acgggaacca cgcaagcgc cgcaagttcc tggagacggt ggagttgcag      120
atcagcttga agaactatga tccccagaag acaagcgct tctcgggcac cgtcaggctt      180
aagtccactc cccgccctaa gttctctgtg tgtgtcctgg ggaccagca gcactgtgac      240 gaggctaagg ccgtggatat cccccacatg gacatcgagg cgctgaaaaa actcaacaag      300
aataaaaaac tggtcaagaa gctggccaag aagtatgatg cgttttttggc ctcagagtct      360 ctgatcaagc agattccacg aatcctcggc ccaggtttaa ataaggcagg aaagttccct      420
tccctgctca cacaacga aaacatggtg gccaaagtgg atgaggtgaa gtccacaatc       480
aagttccaaa tgaagaaggt gttatgtctg gctgtagctg ttggtcacgt gaagatgaca      540
gacgatgagc ttgtgtataa cattcacctg gctgtcaact tcttggtgtc attgctcaag      600
aaaaactggc agaatgtccg ggccttatat atcaagagca ccatgggcaa gccccagcgc      660
ctatattaag gcacatttga ataaattcta ttaccagttc                            700

<210> SEQ ID NO 19
<211> LENGTH: 1125
<212> TYPE: DNA
<213> ORGANISM: Homo sapiens

<400> SEQUENCE: 19
cccccatgtg acagtgacgg ggtccccgct ccaggagacg ctcgagtctg cgtcccggcc       60
ctcagcactg tccactgttt cggtgccagc agagaccagc aggcccggga cagttggtgt      120
ttggccgtgc cgctgtctaa cttggtgtgc agagtgaatt gccgctgccg gagcggagag      180
aggcggagcg gccaggagag aggggatttc tgtcagcgcc ggcctcggga gctcggagac      240
atgaacggct tcacgcctga cgagatgagc gcggcggggg atgcggccgc cgcagtggcc      300
gcagtggtcg ctgccgcggc cgccgccgcc tcggcgggga acgggaccgg cgcgggcacc      360
ggggctgagg tgccgggcgc ggggcgtc tcagcggctg gcccccggg ggcggccggg          420 ccgggccccg ggcaactgtg ctgcctgcgg gaggatggtg agcggtgcgg ccgggcggca      480
ggcaacgcca gcttcagcaa gaggatccag aagagcatct cccagaagaa ggtgaagatc      540
gagctggata agagcgcaag gcatctttac atatgtgatt atcataaaaa cttaattcag      600
agtgttcgaa acagaagaaa gagaaaaggg agtgatgatg atggaggtga ttcacctgtt      660
caagatattg atccccagag ggttgattta taccaattac aagtaaatac acttaggaga      720
tacaaaagac acttcaagct accaaccaga ccaggactta ataaagcaca acttgttgag      780
atagttggtt gccactttag gtctattcca gtgaatgaaa aagacaccttt aacatatttc      840 atctactcag tgaagaatga caagaacaaa tcagatctca aggttgatag tggtgttcac      900
taggagacgt ggaattgaga ctaataactt ggatgttaac actgtttact gtttttttcac      960
```

```
atgtagaaat gttctttgtg tattttttct acagaggatt ttctctgatt ttattttctt      1020
tgtttctgac tctaataatt agttggaaac tcatataaaa tgagctttcc taaattaaat      1080
ctattttaaa taaaggttat tactattaaa aaaaaaaaaa aaaaa                      1125

<210> SEQ ID NO 20
<211> LENGTH: 3608
<212> TYPE: DNA
<213> ORGANISM: Homo sapiens

<400> SEQUENCE: 20
gcggccgctt ccccccggcc gggccccgc cgccccgcgg tccccagagc gccaggcccc        60 cgggggagg gagggagggc gccgggccgg tgggagccag cggcgcgcgg tgggacccac       120
ggagccccgc gacccgccga gcctggagcc gggccgggtc ggggaagccg gctccagccc      180
ggagcgaact tcgcagcccg tcgggggcg gcggggaggg ggcccggagc cggaggaggg       240
ggcggccgcg gcaccccg cctgtgcccc ggcgtcccg gcaccatgc tgtccaactc         300 ccagggccag agcccgccgg tgccgttccc cgccccggcc ccgccgccgc agcccccac       360 ccctgccctg ccgcaccccc cggcgcagcc gccgccgccg ccccccgcagc agttcccgca    420 gttccacgtc aagtccggcc tgcagatcaa gaagaacgcc atcatcgatg actacaaggt     480
caccagccag gtcctggggc tgggcatcaa cggcaaagtt ttgcagatct tcaacaagag     540
gacccaggag aaattcgccc tcaaaatgct tcaggactgc cccaaggccc gcagggaggt     600
ggagctgcac tggcgggcct cccagtgccc gcacatcgta cggatcgtgg atgtgtacga     660
gaatctgtac gcagggagga agtgcctgct gattgtcatg gaatgtttgg acggtggaga     720
actctttagc cgaatccagg atcgaggaga ccaggcattc acagaaagag aagcatccga     780
aatcatgaag agcatcggtg aggccatcca gtatctgcat tcaatcaaca ttgcccatcg     840
ggatgtcaag cctgagaatc tcttatacac ctccaaaagg cccaacgcca tcctgaaact     900
cactgacttt ggctttgcca aggaaaccac cagccacaac tctttgacca ctccttgtta     960
tacaccgtac tatgtggctc cagaagtgct gggtccagag aagtatgaca agtcctgtga    1020
catgtggtcc ctgggtgtca tcatgtacat cctgctgtgt gggtatcccc ccttctactc    1080
caaccacggc cttgccatct ctccgggcat gaagactcgc atccgaatgg gccagtatga    1140
atttcccaac ccagaatggt cagaagtatc agaggaagtg aagatgctca ttcggaatct    1200
gctgaaaaca gagcccaccc agagaatgac catcaccgag tttatgaacc cccttggat    1260 catgcaatca acaaaggtcc ctcaaacccc actgcacacc agccgggtcc tgaaggagga    1320
caaggagcgg tgggaggatg tcaaggggtg tcttcatgac aagaacagcg accaggccac    1380
ttggctgacc aggttgtgag cagaggattc tgtgttcctg tccaaactca gtgctgtttc    1440
ttagaatcct tttattccct gggtctctaa tgggaccttta agaccatct ggtatcatct    1500 tctcattttg cagaagagaa actgaggccc agaggcggag ggcagtctgc tcaaggtcac    1560
gcagctggtg actggttggg gcagaccgga cccaggttc ctgactcctg gcccaagtct    1620
cttcctccta tcctgcggga tcactggggg gctctcaggg aacagcagca gtgccatagc    1680
caggctctct gctgcccagc gctggggtga ggctgccgtt gtcagcgtgg accactaacc    1740
agcccgtctt ctctctctgc tcccacccct gccgccctca ccctgccctt gttgtctctg    1800
tctctcacgt ctctcttctg ctgtctctcc tacctgtctt ctggctctct ctgtaccctt    1860
cctggtgctg ccgtgccccc aggaggagat gaccagtgcc ttggccacaa tgcgcgttga    1920
```

-continued

```
ctacgagcag atcaagataa aaaagattga agatgcatcc aaccctctgc tgctgaagag   1980
gcggaagaaa gctcgggccc tggaggctgc ggctctggcc cactgagcca ccgcgccctc   2040
ctgcccacgg gaggacaagc aataactctc tacaggaata tatttttaa acgaagagac    2100 agaactgtcc acatctgcct cctctcctcc tcagctgcat ggagcctgga actgcatcag   2160
tgactgaatt ctgccttggt tctggccacc ccagagtggg agaggctggg aggttgggag   2220
gctgtggaga gaagtgagca aggtgctctt gaacctgtgc tcattttgca attttatcag   2280
taatttgact tagagttttt acgaaacctc ttttgttgtc cttgccccac tcctctccac   2340
cagacgcctt cctctctgga tactgcaaag gcttgtggtt tgttagaggg tatttgtgga   2400
aactgtcata gggattgtcc ctgtgttgtc ccatctgccc tccctgtttc tccacaacag   2460
cctggggttg tccccgctgg ctcacgcgtt ctgggagctc aaggccacct tggaggagga   2520
tgccacgcac ttcctctctc ggagccctca gacatctcca gtgtgccaga caaataggag   2580
tgagtgtatg tgtgtgtgtg tgtgtgtgtg tgtgcacacg tgtgtatgag tgcgcagatc   2640
tgtgcctggg atcgtgcatt tgaggggcca ggggcaggca gggctgcaga gggagacggc   2700
cctgctgggg cttaggaacc ttctcccctt ttgggtctgc cctgcccata ctgagcctgc   2760
caaagtgcct gggaagccca cccagattct gaaacaggcc ctctgtggcc tgtctctatt   2820
agctgggttc cggaggcag agaggagtga ccgggcactg gcactgcgat caggaagact    2880 ggaccccag ccccaggc cccctcccc ccacttagtg ctggtcctag gtcctctgag       2940
gcactcatct actgaatgac ctctctactt ccccttcttg ccattattaa cccatttttg   3000
tttattttcc ttaaattttt agccatttct ccatgggcca ccgcccagct catgtaggtg   3060
agcctgggca gcttctgttg gcagagcttt tgcatttcct gtgtttgtcc tgggttctgg   3120
ggcatcagcc agctaccct tgtgggcaaa ggcagggcca cttttgaagt cttccctcag    3180
atttccattg tgtggcctgg tgggtcaggg ggagtctttg caccaaagat gtcctgactt   3240
tgcccccttg cccatcagcc atttgccatc accccaaaca actcagcttc ggggccggtg   3300
aggggagggg cctccccag cacagatgag gagcagctgg ggtaggctgt ctgtgccatg    3360 gcccccact cccccttccc ttggagggag aggtggcagg aatacttcac ctttcctctc    3420
cctcaggggc aggtggtgga ggggcgccca gggtcgtctt tgtgtatggg ggaaggcgct   3480
gggtgcctgc agcgcctccc ttgtctcaga tggtgtgtcc agcactcgat tgttgtaaac   3540
tgttgttttg tatgagcgaa attgtcttta ctaaacagat ttaatagtta aaaaaaaaa    3600 aaaaaaaa                                                           3608
```

<210> SEQ ID NO 21
<211> LENGTH: 678
<212> TYPE: DNA
<213> ORGANISM: Homo sapiens

<400> SEQUENCE: 21

```
ctcgcccaaa gaagactaca atctccaggg aaacctgggg cgtctcgcgc aaacgtccat     60
aactgaaagt agctaaggca ccccagccgg aggaagtgag ctctcctggg gcgtggttgt    120
tcgtgatcct tgcatctgtt acttagggtc aaggcttggg tcttgccccg cagacccttg    180
ggacgacccg gccccagcgc agctatgaac ctggagcgag tgtccaatga ggagaaattg    240
aacctgtgcc ggaagtacta cctggggggg tttgctttcc tgccttttct ctggttggtc    300
aacatcttct ggttcttccg agaggccttc cttgtcccag cctacacaga acagagccaa    360
atcaaaggct atgtctggcg ctcagctgtg ggcttcctct tctgggtgat agtgctcacc    420
```

| | |
|---|---|
| tcctggatca ccatcttcca gatctaccgg ccccgctggg gtgcccttgg ggactacctc | 480 |
| tccttcacca tacccctggg cacccctga caacttctgc acatactggg gccctgctta | 540 |
| ttctcccagg acaggctcct taaagcagag gagcctgtcc tgggagcccc ttctcaaact | 600 |
| cctaagactt gttttcatgt cccacgttct ctgctgacat ccccaataa aggaccctaa | 660 |
| ctttcaaaaa aaaaaaaa | 678 |

<210> SEQ ID NO 22
<211> LENGTH: 2272
<212> TYPE: DNA
<213> ORGANISM: Homo sapiens

<400> SEQUENCE: 22

| | |
|---|---|
| gaagcgactc tgagtcccgg gctcggagcg caggctcagc tccgcgctgc gagcgctacg | 60 |
| ggcgcagggg cggggagccg gcccggagcg cagtttccag tggggccggg gtttcacccg | 120 |
| ggccctctct gtttgaaccg aacccgacaa atgggcgcat gacgatggag agcagggaaa | 180 |
| tggactgcta tctccgtcgc ctcaaacagg agctgatgtc catgaaggag gtgggtgatg | 240 |
| gcttacagga tcagatgaac tgcatgatgg gtgcactgca agaactgaag ctcctccagg | 300 |
| tgcagacagc actggaacag ctggagatct ctggaggggg tcctgtgcca ggcagccctg | 360 |
| aaggtcccag gacccagtgc gagcaccctt gttgggaggg tggcagaggt cctgccaggc | 420 |
| ccacagtctg ttcccctcc agtcaacctt ctcttggcag cagcaccaag tttccatccc | 480 |
| ataggagtgt ctgtggaagg gatttagccc ccttgcccag gacacagcca catcaaagct | 540 |
| gtgctcagca ggggccagag cgagtggaac cggatgactg gacctccacg ttgatgtccc | 600 |
| ggggccggaa tcgacagcct ctggtgttag gggacaacgt ttttgcagac ctggtgggca | 660 |
| attggctaga cttgccagaa ctggagaagg gtggggagaa gggtgagact ggggggggcac | 720 |
| gtgaacccaa aggagagaaa ggccagcccc aggagctggg ccgcaggttc gccctgacag | 780 |
| caaacatctt taagaagttc ttgcgtagtg tgcggcctga ccgtgaccgg ctgctgaagg | 840 |
| agaagccagg ctgggtgaca cccatggtcc ctgagtcccg aaccggccgc tcacagaagg | 900 |
| tcaagaagcg gagcctttcc aagggctctg gacatttccc cttcccaggc accggggagc | 960 |
| acaggcgagg ggagaatccc cccacaagct gccccaaggc cctggagcac tcaccctcag | 1020 |
| gatttgatat taacacagct gtttgggtct gaatcctaga gacagaaagt tgactgagcc | 1080 |
| tgaaagggcc aggtcccagt gctgggcccc tggggaggag ggagggtggg cggtatggct | 1140 |
| ctcgaaagcc caactccaag ttcctttccc ccagaaagcg gggagaagcc agagttcttg | 1200 |
| gctcaggact gaagggaagg tggttgggag aggctgtctt gggggctagc tggtggagga | 1260 |
| ggtaagagta gctggagagt gagctgtgcg tgtgtgtgtg tgtgtgtgca tgtgtgtgtc | 1320 |
| tgtctggcat gcatgcactc actttggggc tggaggtgac agtaggtgag ggcagaggag | 1380 |
| gagatcagaa aatccctctg acatctccac tgccccaaa gacctccgtt gaacattctg | 1440 |
| tatggaaaag agccctggag catcaggttc cccagatagg ccccaaata aagacctgtc | 1500 |
| tatggctctc ccaaccttct gtcagcttct ttggcaagac attgctccag gcacagggac | 1560 |
| tgaaccccag gcctcctggg actggagcag cagtgaggca aaacccgacc tgctagcccct | 1620 |
| ttctgccttg gaggtttcag tccatacctg gactctgaga aaatgagctg aataaggagt | 1680 |
| acagtgtgta aggagcagcc agggaagccc tagacactcc ccgcgtctcc cccatgcaca | 1740 |
| ggggaaggat gttgacatag cactgggctg tttgaatgcc ttttcatctc catggtctca | 1800 |

| | |
|---|---|
| tttgaaagtg agcgaggcag gcaggcatga tcccattttc cagataagga aacaagccta | 1860 |
| gatatgctac atgtccagga acaactgcag ccaggaggca gaacagccta ggtctaactg | 1920 |
| cagagtagaa gctggaccct ggagttacca acactcctcc ccaacagttc ttagcgcccc | 1980 |
| gcaggctggg cgctgtggct cacgcctgta atcccagcac tttgggaggg caaggcaggc | 2040 |
| ggattacctg gggtcaggag ttcatgacca gcctggccaa catggtgaaa ccccgtctct | 2100 |
| actaaaaaaa tacgtaaaaa ttagccaggc gtggtggcac acgcctgtaa acccagctac | 2160 |
| tcgggaggct gaggcaggag aattgcttga gcccgggaga gggaggttgc agtgagccga | 2220 |
| gatcatgcca ctgcactcca gcctggctga cagagcaaga ctcccctgtc tc | 2272 |

<210> SEQ ID NO 23
<211> LENGTH: 2358
<212> TYPE: DNA
<213> ORGANISM: Homo sapiens

<400> SEQUENCE: 23

| | |
|---|---|
| ggagaggatc ccggagccgg tgagaattct ctgttttttc tctaccatcc tttccaggcc | 60 |
| ttttcctcac ctaatgagtc gtagagacga gggcccagag agtctgtaaa gtggctggtg | 120 |
| aaagattagt gtcccagggc cctacatccg ggaggtggtt cgggataaag agaactagtc | 180 |
| ttgggaacaa tgtaggtggg aacttaaggg aatgggagag cggcccatag aggtggacgg | 240 |
| agggcgcgat tggagtaaag cggaccctgt gtaggtatag agttgagtca agtggagtca | 300 |
| ctgcctctgt ccctctggtc agcgtgatgg ccagaggcct gggggggcccc cactgggtgg | 360 |
| ccgtgggact gctgacctgg gcgaccttgg ggcttctggt ggctggactc gggggtcatg | 420 |
| acgacctgca cgacgatctg caagaggact tccatggcca cagccacagg cactcacatg | 480 |
| aagatttcca ccatggtcac agccatgccc atggtcatgg ccacactcac gagagcatct | 540 |
| ggcatggaca tacccacgat cacgaccatg acattcaca tgaggattta ccaccatggcc | 600 |
| atagccatgg ctactcccat gagagcctct accacagagg acatggacat gaccatgagc | 660 |
| atagccatgg aggctatggg gagtctgggg ctccaggcat caagcaggac ctggatgctg | 720 |
| tcactctctg ggcttatgca ctgggggcca cagtgctgat ctcagcagct ccatttttg | 780 |
| tcctcttcct tatccccgtg gagtcgaact ctccccggca tcgctctcta cttcagatct | 840 |
| tgctcagttt tgcttccggt gggctcctgg gagatgcttt cctgcacctc attcctcatg | 900 |
| ctcttgaacc tcattctcac cacactctgg agcaacccgg acatggacac tcccacagtg | 960 |
| gccagggccc cattctgtct gtgggcctgt gggttctcag tggaattgtt gccttttcttg | 1020 |
| tcgtggagaa atttgtgaga catgtgaaag gaggacatgg tcacagtcat ggacatggac | 1080 |
| acgctcacag tcatacacgt ggaagtcatg gacatggaag acaagagcgt tctaccaagg | 1140 |
| agaagcagag ctcagaggaa gaaggaaagg aaacaagagg ggttcagaag aggcgaggag | 1200 |
| ggagcacagt acccaaagat gggccagtga gaccctcagaa cgctgaagaa gaaaaaagag | 1260 |
| gcttagacct gcgtgtgtcg gggtacctga atctggctgc tgacttggca cacaacttca | 1320 |
| ctgatggtct ggccattggg gcttcctttc gaggggccg gggactaggg atcctgacca | 1380 |
| caatgactgt cctgctacat gaagtgcccc acgaggtcgg ggactttgcc atcttggtcc | 1440 |
| agtctggctg caccaaaaag caggcgatgc gtctgcaact actgacagca gtaggggcac | 1500 |
| tggcaggcac agctgtgccc ttctcactga aggaggagca gtggacagtg aaattgcagg | 1560 |
| tggtgcaggt cctggctggg tcctgccatt tactgcaggg ggctttatct acgtagcaac | 1620 |
| agtgtctgtg ttgcccgagc tgctgaggga ggcatcacca ttgcaatcac ttctggaggt | 1680 |

```
gctgggctg ctgggggag ttatcatgat ggtgctgatt gcccaccttg agtgagggt    1740 ggataaacta ccctgcccca aacctctacc cctaactcca ggtcagggt gcgtagaggt    1800 tgggggccct ggccagggac atctgccaaa ggaaggaact gtagcctggg agcaatggtt   1860
actttggcat tagggccttc aagggctggc agtcttacag aggctggagc ggtgagaatg   1920
agaggccaga gggaccatag tgttgggcac tgtctgacca tgttgcattt ggaaggctaa   1980 atgggggccat gaagaaggct ggaagggaca ggggtgatg cagcctacc tggtgtcccc    2040 taccccacct gttctcggag aaccaagttg ctacacagga agttctccaa ggtccagttt   2100
cctttctccc accagttggt ggaggcttca gggaagacca gagtcctgga cagagaggt    2160 aacaggagga gtcgggata aacatcaaac atcaatcgtg tgtcctgatt tgggagtgat    2220
tggggggatg gggtgggaga gggttaattg gtattctcat ggcctgattt tttttgttc    2280 tattccttt atatcactgt gtttgaatcg agggggaggg gtggtaaccg gaaataaaga    2340
cctccgatct tccgcccc                                                2358

<210> SEQ ID NO 24
<211> LENGTH: 1856
<212> TYPE: DNA
<213> ORGANISM: Homo sapiens

<400> SEQUENCE: 24
agccaaaaga ggaagggacc ggcctcccac gtccacaggg acctgacttc cacctctctg    60
cccagatttg cttatgtcac tgtcgccccg ggacggggag gtggggagct gagggcaagt   120
cgcgcccgcc cctgaaatcc cagccgccta gcgattggct gcaagggtct cggcttggcc   180
gcggattaat cacacccgag ggcttgaaag gtggctggga gcgccggaca cctcagacgg   240
acggtggcca gggatcaggc agcggctcag gcgaccctga gtgtgccccc accccgccat   300
ggcccggctg ctgcaggcgt cctgcctgct ttccctgctc ctggccggct tcgtctcgca   360
gagccgggga caagagaagt cgaagatgga ctgccatggt ggcataagtg gcaccattta   420
cgagtacgga gccctcacca ttgatgggga ggagtacatc cccttcaagc agtatgctgg   480
caaatacgtc ctctttgtca acgtggccag ctactgaggc ctgacgggcc agtacattga   540
actgaatgca ctacaggaag agcttgcacc attcggtctg gtcattctgg gctttccctg   600
caaccaattt ggaaaacagg aaccaggaga gaactcagag atccttccta ccctcaagta   660
tgtccgacca ggtggaggct ttgtccctaa tttccagctc tttgagaaag gggatgtcaa   720
tggagagaaa gagcagaaat tctacacttt cctaaagaac tcctgtcctc ccacctcgga   780
gctcctgggt acatctgacc gcctcttctg ggaacccatg aaggttcacg acatccgctg   840
gaactttgag aagttcctgg tggggccaga tggtataccc atcatgcgct ggcaccaccg   900
gaccacggtc agcaacgtca agatggacat cctgtcctac atgaggcggc aggcagccct   960
gggggtcaag aggaagtaac tgaaggccgt ctcatcccat gtccaccatg taggggaggg   1020
actttgttca ggaagaaatc cgtgtctcca accacactat ctacccatca cagacccctt   1080
tcctatcact caaggcccca gcctggcaca aatggatgca tacagttctg tgtactgcca   1140
ggcatgtggg tgtgggtgca atgtgggtgt ttacacacat gcctacaggt atgcgtgatt   1200
gtgtgtgtgt gcatgggtgt acagccacgt gtctacctat gtgtctttct gggaatgtgt   1260
accatctgtg tgcctgcagc tgtgtagtgc tggacagtga caacccttc tctccagttc   1320 tccactccaa tgataatagt tcacttatac ctaaacccaa aggaaaaacc agctctaggt   1380
```

-continued

| | |
|---|---|
| ccaattgttc tgctctaact gatacctcaa ccttggggcc agcatctccc actgcctcca | 1440 |
| aatattagta actatgactg acgtccccag aagtttctgg gtctaccaca ctccccaacc | 1500 |
| ccccactcct acttcctgaa gggccctccc aaggctacat ccccacccca cagttctccc | 1560 |
| tgagagagat caacctccct gagatcaacc aaggcagatg tgacagcaag gccacggac | 1620 |
| cccatggcag gggtggcgtc ttcatgaggg aggggcccaa agcccttgtg ggcggacctc | 1680 |
| ccctgagcct gtctgagggg ccagcccttc gtgcattcag gctaaggccc ctgggcaggg | 1740 |
| atgccacccc tgctccttcg gaggacgtgc cctcacccct cactggtcca ctggcttgag | 1800 |
| actcaccccg tctgcccagt aaaagccttt ctgcagcaaa aaaaaaaaa aaaaaa | 1856 |

<210> SEQ ID NO 25
<211> LENGTH: 2727
<212> TYPE: DNA
<213> ORGANISM: Homo sapiens

<400> SEQUENCE: 25

| | |
|---|---|
| ggggacactg gatcacctag tgtttcacaa gcaggtacct tctgctgtag agagagaga | 60 |
| actaaagttc tgaaagacct gttgcttttc accaggaagt tttactgggc atctcctgag | 120 |
| cctaggcaat agctgtaggg tgacttctgg agccatcccc gtttcccgc ccccaaaag | 180 |
| aagcggagat ttaacgggga cgtgcggcca gagctgggga aatgggcccg cgagccaggc | 240 |
| cggcgcttct cctcctgatg cttttgcaga ccgcggtcct gcaggggcgc ttgctgcgtt | 300 |
| cacactctct gcactacctc ttcatggggtg cctcagagca ggaccttggt cttttccttgt | 360 |
| ttgaagcttt gggctacgtg gatgaccagc tgttcgtgtt ctatgatcat gagagtcgcc | 420 |
| gtgtggagcc ccgaactcca tgggtttcca gtagaatttc aagccagatg tggctgcagc | 480 |
| tgagtcagag tctgaaaggg tgggatcaca tgttcactgt tgacttctgg actattatgg | 540 |
| aaaatcacaa ccacagcaag gagtcccaca ccctgcaggt catcctgggc tgtgaaatgc | 600 |
| aagaagacaa cagtaccgag ggctactgga agtacgggta tgatgggcag gaccaccttg | 660 |
| aattctgccc tgacacactg gattggagag cagcagaacc cagggcctgg cccaccaagc | 720 |
| tggagtggga aaggcacaag attcgggcca ggcagaacag ggcctacctg gagagggact | 780 |
| gccctgcaca gctgcagcag ttgctggagc tggggagagg tgttttggac caacaagtgc | 840 |
| ctcctttggt gaaggtgaca catcatgtga cctcttcagt gaccactcta cggtgtcggg | 900 |
| ccttgaacta ctacccccag aacatcacca tgaagtggct gaaggataag cagccaatgg | 960 |
| atgccaagga gttcgaacct aaagacgtat tgcccaatgg ggatgggacc taccagggct | 1020 |
| ggataacctt ggctgtaccc cctggggaag agcagagata tacgtgccag gtggagcacc | 1080 |
| caggcctgga tcagcccctc attgtgatct gggagccctc accgtctggc acccctagtca | 1140 |
| ttggagtcat cagtggaatt gctgtttttg tcgtcatctt gttcattgga attttgttca | 1200 |
| taatattaag gaagaggcag ggttcaagag gagccatggg gcactacgtc ttagctgaac | 1260 |
| gtgagtgaca cgcagcctgc agactcactg tgggaaggag acaaaactag agactcaaag | 1320 |
| agggagtgca tttatgagct cttcatgttt caggagagag ttgaacctaa acatagaaat | 1380 |
| tgcctgacga actccttgat tttagccttc tctgttcatt tcctcaaaaa gatttcccca | 1440 |
| tttaggtttc tgagttcctg catgccggtg atccctagct gtgacctctc ccctggaact | 1500 |
| gtctctcatg aacctcaagc tgcatctaga ggcttcctcc atttcctccg tcacctcaga | 1560 |
| gacatacacc tatgtcattt catttcctat ttttggaaga ggactcctta aatttggggg | 1620 |
| acttacatga ttcattttaa catctgagaa aagctttgaa ccctgggacg tggctagtca | 1680 |

```
taaccttacc agattttac  acatgtatct atgcatttc  tggacccgtt caacttttcc    1740
tttgaatcct ctctctgtgt tacccagtaa ctcatctgtc accaagcctt ggggattctt    1800
ccatctgatt gtgatgtgag ttgcacagct atgaaggctg tacactgcac gaatggaaga    1860
ggcacctgtc ccagaaaaag catcatggct atctgtgggt agtatgatgg gtgttttag     1920 caggtaggag gcaaatatct tgaaaggggt tgtgaagagg tgttttttct aattggcatg    1980
aaggtgtcat acagatttgc aaagtttaat ggtgccttca tttgggatgc tactctagta    2040
ttccagacct gaagaatcac aataattttc tacctggtct ctccttgttc tgataatgaa    2100
aattatgata aggatgataa aagcacttac ttcgtgtccg actcttctga gcacctactt    2160
acatgcatta ctgcatgcac ttcttacaat aattctatga gataggtact attatcccca    2220
tttctttttt aaatgaagaa agtgaagtag gccgggcacg gtggctcacg cctgtaatcc    2280
cagggtgctg agattacagg tgtgagccac cctgcccagc cgtcaaaaga gtcttaatat    2340
atatatccag atggcatgtg tttactttat gttactacat gcacttggct gcataaatgt    2400
ggtacaagca ttctgtcttg aagggcaggt gcttcaggat accatataca gctcagaagt    2460
ttcttcttta ggcattaaat tttagcaaag atatctcatc tcttcttta  aaccattttc    2520 ttttttgtg  gttagaaaag ttatgtagaa aaaagtaaat gtgatttacg ctcattgtag    2580
aaaagctata aatgaatac  aattaaagct gttatttaat tagccagtga aaaactatta    2640
acaacttgtc tattacctgt tagtattatt gttgcattaa aaatgcatat actttaataa    2700
atgtatattg tattgtaaaa aaaaaaa                                        2727

<210> SEQ ID NO 26
<211> LENGTH: 879
<212> TYPE: DNA
<213> ORGANISM: Homo sapiens

<400> SEQUENCE: 26
ctcctcacag aagcctggag ctgggcatcc aagaagaagc agcctcattt gttttctggt      60
gtcatcgtag gtggccacct atggcttttg ggaatgtaaa aagggcagct ctctggcatg     120
ttcctgactg aggatctcat aacatttaac ttgaggaact tcctcctttt ccagctttgg     180
gagtcaagct tctcacctgg ggcgggtggg ttctgcacca ccctcccacc ctccttcctc     240
cgtgtggacg atagagccac atccagcacc acggacagct cccgggcgcc ttcatctcct     300
cgtcctccag gcagcacaag ccattgtgga atctccacca ggtgtacaga acggtgcctc     360
tgcgtcctgc cactcaggac ctctcaagtc cccgatgtga tggctcctca gcatgatcag     420
gagaaattcc atgatcttgc ttattcctgt cttgggaagt ccttctccat gtctaaccaa     480
gatctatatg gctatagcac cagctctttg gctcttggct tggcatggct aagttgggag     540
accaaaaaga agaatgtact tcatctggtt gggctggatt ccctctgata agccttccca     600
gttgactgaa agatgaggct aggctctagc aagttgaagt caaaccagct ccttcaagaa     660
gctttgagca gaatgaagtg gggaggaccc agcttccagc ccaggaagcc cactgtacct     720
ggagccatct gggataagac tttgacccat gactcccata tccacagcct gtccatccta     780
gcccatccca gtttatcctg tatcatttga gctgggattc ccacatcctc tgagttggaa     840
gtcccatctc aagtcttcaa taaagactct tgaatattg                            879

<210> SEQ ID NO 27
<211> LENGTH: 3287
<212> TYPE: DNA
```

<213> ORGANISM: Homo sapiens

<400> SEQUENCE: 27

| | | | | | | |
|---|---|---|---|---|---|---|
| atggcgctgg | ctgtcttgcg | ggtcctggag | ccctttccga | ccgagacacc | cccgttggca | 60 |
| gtgctgctgc | cacccggggg | cccgtggccg | gcggcggagc | tgggcctggt | gctggccctg | 120 |
| aggcctgcag | gggagagccc | ggcagggccg | gcgctgctgg | tggcagccct | ggaggggccg | 180 |
| gacgcgggca | ccgaagagca | gggtcccggg | ccgccgcagc | tactggttag | ccgcgcgctg | 240 |
| ctgcggctcc | tggcactggg | ctccggggcc | tgggtgcggg | cgcgggcggt | gcggcggccc | 300 |
| ccggcgctag | gttgggcact | gcttggcacc | tcgctgggc | ctgggctcgg | accgcgagtc | 360 |
| gggccgctgc | tggtgaggcg | cggagagacc | ctcccagttc | ccggaccgcg | ggtgctggag | 420 |
| acgcggccgg | cgttgcaagg | gctgctgggc | cagggactc | ggctggctgt | gactgagctc | 480 |
| cgcgggcggg | ccagactgtg | tccagagtct | ggggacagca | gtcggccccc | accccgccc | 540 |
| gtggtgtcct | cctttgcggt | ttctggcaca | gtgcggcgac | tccagggagt | tctgggaggg | 600 |
| actgagatt | cactagggt | gagccggagc | tgtctccgtg | gccttggcct | cttccagggc | 660 |
| gaatgggtgt | gggtggccca | ggccagagag | tcatcgaaca | cttcacagcc | gcacttggct | 720 |
| agggtgcagg | tcctagaacc | tcgctgggac | ctctctgata | gactgggacc | cggctctgga | 780 |
| ccgctgggag | agcccctcgc | tgacggactg | gcgcttgtcc | ctgccacttt | ggcttttaat | 840 |
| cttggctgtg | accccctgga | aatgggagag | ctcagaattc | agaggtactt | ggaaggctcc | 900 |
| atcgcccctg | aagacaaagg | aagctgctca | ttgctgcctg | ggcctccatt | tgccagagag | 960 |
| ttacacatcg | aaattgtgtc | ttctccccac | tacagcacta | atggaaatta | tgacggtgtt | 1020 |
| ctttaccggc | actttcagat | acccagggta | gtccaggaag | gggatgttct | atgtgtgcca | 1080 |
| acaattgggc | aagtagagat | cctggaagga | agtccagaga | aactgcccag | gtggcgggaa | 1140 |
| atgtttttta | aagtgaagaa | aacagttggg | gaagctccag | atggaccagc | cagtgcctac | 1200 |
| ttggccgaca | ccaccatac | ctccttgtac | atggtgggtt | ctaccctgag | ccctgttcca | 1260 |
| tggctcccctt | cagaggaatc | cactctctgg | agcagtttgt | ctcctccagg | cctggaggcc | 1320 |
| ttggtgtctg | aactctgtgc | tgtcctgaag | cctcgcctcc | agccagggg | tgccctgctg | 1380 |
| acaggaacta | gcagtgtcct | tctacggggc | ccccaggct | gtgggaagac | cacagtagtt | 1440 |
| gctgctgcct | gtagtcacct | tgggctccac | ttactgaagg | tgccctgctc | cagcctctgt | 1500 |
| gcagaaagta | gtggggctgt | ggagacaaaa | ctgcaggcca | tcttctcccg | ggcccgccgt | 1560 |
| tgccggcctg | cagtcctgtt | gctcacagct | gtggaccttc | tgggccggga | ccgtgatggg | 1620 |
| ctgggtgagg | atgcccgtgt | gatggctgtg | ctgcgtcacc | tcctcctcaa | tgaggacccc | 1680 |
| ctcaacagct | gccctcccct | catggttgtg | gccaccacaa | gccgggccca | ggacctgcct | 1740 |
| gctgatgtgc | agacagcatt | tcctcatgag | ctcgaggtgc | ctgctctgtc | agaggggcag | 1800 |
| cggctcagca | tcctgcgggc | cctcactgcc | caccttcccc | tgggccagga | ggtgaacttg | 1860 |
| gcacagctag | cacggcggtg | tgcaggcttt | gtggtagggg | atctctatgc | ccttctgacc | 1920 |
| cacagcagcc | gggcagcctg | caccaggatc | aagaactcag | gtttggcagg | tggcttgact | 1980 |
| gaggaggatg | aggggagct | gtgtgctgcc | ggctttcctc | tcctggctga | ggactttggg | 2040 |
| caggcactgg | agcaactgca | gacagctcac | tcccaggccg | ttggagcccc | caagatcccc | 2100 |
| tcagtgtcct | ggcatgatgt | gggtgggctg | caggaggtga | agaaggagat | cctggagacc | 2160 |
| attcagctcc | ccctgagcca | ccctgagcta | ctgagcctgg | gcctgagacg | tcaggcctt | 2220 |
| ctgctccatg | ggccccctgg | caccggcaag | acccttctgg | ccaaggcagt | agccactgag | 2280 |

```
tgcagcctta ccttcctcag cgtgaagggg ccagagctca ttaacatgta tgtgggccaa    2340
agtgaggaga atgtgcggga agtgtttgcc agggccaggg ctgcagctcc atgcattatc    2400
ttctttgatg aactggactc tttggcccca agccggggc gaagtggaga ttctggagga     2460
gtgatggaca gggtggtgtc tcagctcctt gccgagctag atgggctgca cagcactcag    2520
gatgtgtttg tgattggagc caccaacaga ccagatctcc tggaccctgc ccttctgcgg    2580
cctggcagat ttgacaagct ggtgtttgtg ggggcaaatg aggaccgggc ctcccagcta    2640
cgcgttctaa gtgccatcac acgcaaattc aagctagagc catctgtgag cctggtaaac    2700
gtgctagatt gctgccctcc ccagctgacg ggcgcggacc tctactctct ctgctctgat    2760
gctatgacag ctgccctcaa acgcagggtt catgacctgg aggaagggct ggaacaaggt    2820
agctcagcac tgatgctcac catggaggac ttgctgcagg ctgccgcccg gctgcaaccc    2880
tcagtcagtg agcaggagct gctccggtac aagcgcatcc agcgcaagtt tgctgcctgc    2940
taggagcccc ccagggtctg gaccccgct cagcatggct gcaggtacct tgatagccca     3000
cagagagatc tgggaaggaa gggctcctcc tcaggctgct gccaacccac ctggaggcca    3060
cctccctcca ggagatccca gggtgcaaag tggcattgag acagcagcaa cagctcaaga    3120
gatatctcct gcctacttgc ccctccttcc aggccggctc taagagaaag gcccatctac    3180
tcaggaagag ggccagggcc ttgggttctg ggattgggc cctgagaggg ctagttctgt     3240
ggctgaaaat aaagcatgtc ccgcccccta aaaaaaaaaa aaaaaa                   3287

<210> SEQ ID NO 28
<211> LENGTH: 7239
<212> TYPE: DNA
<213> ORGANISM: Homo sapiens

<400> SEQUENCE: 28
cggggcagcc gagggcccct gactcggctc ctcgcggcga catggatcgg atggccagct      60
ccatgaagca ggtgcccaac ccactgccca aggtgctgag ccggcgcggg gtcggcgctg     120
ggctggaggc ggcggagcgc gagagcttcg agcggactca gactgtcagc atcaataagg     180
ccattaatac gcaggaagtg gctgtaaagg aaaaacacgc cagaacgtgc atactgggca     240
cccaccatga gaaggggca cagaccttct ggtctgttgt caaccgcctg cctctgtcta      300
gcaacgcagt gctctgctgg aagttctgcc atgtgttcca caaactcctc cgagatggac     360
acccgaacgt cctgaaggac tctctgagat acagaaatga attgagtgac atgagcagga    420
tgtgggccca cctgagcgag gggtatggcc agctgtgcag catctacctg aaactgctaa    480
gaaccaagat ggagtaccac accaaaaatc ccaggttccc aggcaacctg cagatgagtg    540
accgccagct ggacgaggct ggagaaagtg acgtgaacaa cttttttccag ttaacagtgg   600 agatgtttga ctacctggag tgtgaactca acctcttcca aacagtattc aactccctgg    660
acatgtcccg ctctgtgtcc gtgacggcag cagggcagtg ccgcctcgcc ccgctgatcc    720
aggtcatctt ggactgcagc caccttttatg actacactgt caagcttctc ttcaaactcc   780
actcctgcct cccagctgac accctgcaag gccaccggga ccgcttcatg gagcagtttta   840 caaagttgaa agatctgttc taccgctcca gcaacctgca gtacttcaag cggctcattc    900
agatccccca gctgcctgag aacccaccca acttcctgcg agcctcagcc ctgtcagaac    960
atatcagccc tgtggtggtg atccctgcag aggcctcatc cccgacagc gagccagtcc    1020 tagagaagga tgacctcatg gacatggatg cctctcagca gaatttattt gacaacaagt    1080
```

-continued

```
ttgatgacat ctttggcagt tcattcagca gtgatccctt caatttcaac agtcaaaatg      1140
gtgtgaacaa ggatgagaag gaccacttaa ttgagcgact atacagagag atcagtggat      1200
tgaaggcaca gctagaaaac atgaagactg agagccagcg ggttgtgctg cagctgaagg      1260
gccacgtcag cgagctggaa gcagatctgg ccgagcagca gcacctgcgg cagcaggcgg      1320
ccgacgactg tgaattcctg cgggcagaac tggacgagct caggaggcag cgggaggaca      1380
ccgagaaggc tcagcggagc ctgtctgaga tagaaaggaa agctcaagcc aatgaacagc      1440
gatatagcaa gctaaaggag aagtacagcg agctggttca gaaccacgct gacctgctgc      1500
ggaagaatgc agaggtgacc aaacaggtgt ccatggccag acaagcccag gtagatttgg      1560
aacgagagaa aaaagagctg gaggattcgt tggagcgcat cagtgaccag gccagcgga      1620 agactcaaga cagctggaa gttctagaga gcttgaagca ggaacttgcc acaagccaac      1680
gggagcttca ggttctgcaa ggcagcctgg aaacttctgc ccagtcagaa gcaaactggg      1740
cagccgagtt cgccgagcta gagaaggagc gggacagcct ggtgagtggc gcagctcata      1800
gggaggagga attatctgct cttcggaaag aactgcagga cactcagctc aaactggcca      1860
gcacagagga atctatgtgc cagcttgcca aagaccaacg aaaaatgctt ctggtggggt      1920
ccaggaaggc tgcggagcag gtgatacaag acgccctgaa ccagcttgaa gaacctcctc      1980
tcatcagctg cgctgggtct gcagatcacc tcctctccac ggtcacatcc atttccagct      2040
gcatcgagca actggagaaa agctggagcc agtatcggc ctgcccagaa gacatcagtg      2100
gacttctcca ttccataacc ctgctggccc acttgaccag cgacgccatt gctcatggtg      2160
ccaccacctg cctcagagcc ccacctgagc ctgccgactc actgaccgag gcctgtaagc      2220
agtatggcag ggaaaccctc gcctacctgg cctccctgga ggaagaggga agccttgaga      2280
atgccgacag cacagccatg aggaactgcc tgagcaagat caaggccatc ggcgaggagc      2340
tcctgcccag gggactggac atcaagcagg aggagctggg ggacctggtg acaaggaga      2400 tggcggccac ttcagctgct attgaaactg ccacggccag aatagaggag atgctcagca      2460
aatcccgagc aggagacaca ggagtcaaat tggaggtgaa tgaaaggatc cttggttgct      2520
gtaccagcct catgcaagct attcaggtgc tcatcgtggc ctctaaggac ctccagagag      2580
agattgtgga gagcggcagg ggtacagcat cccctaaaga gttttatgcc aagaactctc      2640
gatggacaga aggacttatc tcagcctcca aggctgtggg ctggggagcc actgtcatgg      2700
tggatgcagc tgatctggtg gtacaaggca gagggaaatt tgaggagcta atggtgtgtt      2760
ctcatgaaat tgctgctagc acagcccagc ttgtggctgc atccaaggtg aaagctgata      2820
aggacagccc caacctagcc cagctgcagc aggcctctcg gggagtgaac caggccactg      2880
ccggcgttgt ggcctcaacc atttccggca aatcacagat cgaagagaca gacaacatgg      2940
acttctcaag catgacgctg acacagatca aacgccaaga gatggattct caggttaggg      3000
tgctagagct agaaaatgaa ttgcagaagg agcgtcaaaa actgggagag cttcggaaaa      3060
agcactacga gcttgctggt gttgctgagg gctgggaaga aggaacagag gcatctccac      3120
ctacactgca agaagtggta accgaaaaag aatagagcca aaccaacacc ccatatgtca      3180
gtgtaaatcc ttgttaccta tctcgtgtgt gttatttccc cagccacagg ccaaatcctt      3240
ggagtcccag gggcagccac accactgcca ttacccagtg ccgaggacat gcatgacact      3300
tccaaagact ccctccatag cgacaccctt tctgtttgga cccatggtca tctctgttct      3360
tttcccgcct cccagttag catccaggct ggccagtgct gccatgagc aagcctaggt      3420 acgaagaggg gtggtggggg gcagggccac tcaacagaga ggaccaacat ccagtcctgc      3480
```

```
tgactatttg accccacaa caatgggtat ccttaataga ggagctgctt gttgtttgtt      3540
gacagcttgg aaagggaaga tcttatgcct tttcttttct gttttcttct cagtcttttc      3600
agtttcatca tttgcacaaa cttgtgagca tcagagggct gatggattcc aaaccaggac      3660
actaccctga gatctgcaca gtcagaagga cggcaggagt gtcctggctg tgaatgccaa      3720
agccattctc cccctctttg ggcagtgcca tggatttcca ctgcttctta tggtggttgg      3780
ttgggttttt tggttttgtt ttttttttta agtttcactc acatagccaa ctctcccaaa      3840
gggcacaccc ctggggctga gtctccaggg ccccccaact gtggtagctc agcgatggt       3900 gctgcccagg cctctcggtg ctccatctcc gcctccacac tgaccaagtg ctggcccacc      3960
cagtccatgc tccagggtca ggcggagctg ctgagtgaca gctttcctca aaaagcagaa      4020
ggagagtgag tgccttccc tcctaaagct gaatcccggc ggaaagcctc tgtccgcctt       4080
tacaagggag aagacaacag aaagagggac aagagggttc acacagccca gttcccgtga      4140
cgaggctcaa aaacttgatc acatgcttga atggagctgg tgagatcaac aacactactt      4200
ccctgccgga atgaactgtc cgtgaatggt ctctgtcaag cgggccgtct cccttggccc      4260
agagacggag tgtgggagtg attcccaact cctttctgca gacgtctgcc ttggcatcct      4320
cttgaatagg aagatcgttc caccttctac gcaattgaca aacccggaag atcagatgca      4380
attgctccca tcagggaaga accctatact tggtttgcta cccttagtat ttattactaa      4440
cctcccttaa gcagcaacag cctacaaaga gatgcttgga gcaatcagaa cttcaggtgt      4500
gactctagca aggctcatct ttctgcccgg ctacatcagc cttcaagaat cagaagaaag      4560
gccaaggtgc tggactgtta ctgacttgga tcccaaagca aggagatcat ttggagctct      4620
tgggtcagag aaaatgagaa aggacagagc cagcggctcc aactcctttc agccacatgc      4680
cccaggctct cgctgccctg tggacaggat gaggacagag ggcacatgaa cagcttgcca      4740
gggatgggca gcccaacagc acttttcctc ttctagatgg accccagcat ttaagtgacc      4800
ttctgatctt ggaaaaacag cgtcttcctt ctttatctat agcaactcat tggtggtagc      4860
catcaagcac ttcccaggat ctgctccaac agaatattgc taggttttgc tacatgacgg      4920
gttgtgagac ttctgtttga tcactgtgaa ccaaccccca tctccctagc ccaccccct       4980 ccccaactcc ctctctgtgc attttctaag tgggacattc aaaaaactct ctcccaggac      5040
ctcggatgac catactcaga cgtgtgacct ccatactggg ctaaggaagt atcagcacta      5100
gaaattgggc agtcttaatg ttgaatgctg ctttctgctt agtattttt tgattcaagg       5160 ctcagaagga atggtgcgtg gcttccctgt cccagttgtg gcaactaaac caatcggtgt      5220
gttcttgatg cgggtcaaca tttccaaaag tggctagtcc tcacttctag atctcagcca      5280
ttctaactca tatgttccca attaccaagg ggtggccggg cacagtggct cacgcctgta      5340
atcccagcac tttgagaggc tgaggtggta ggatcacctg aggtcaggag ttcaagacca      5400
gcctgtccaa catggtgaaa ccccatctc tactaaaaat accaaaaatt agccgagcgt       5460
agtgacgggt gcccgtaatc ccagctactc aggaggctga gacaggagaa tcacctgaac      5520
cccagaggca gaggttgcag tgagctgaga tcacgccatt gtactccagc ctgggcaaca      5580
agagcaaaac tccgtctcaa aaaaaaaaa aaattacaaa tggggcaaac agtctagtgt       5640
aatggatcaa attaagattc tctgcccagc cgggcacagt ggcgcatgcc tgtaatccca      5700
gaactttggg aggccaagac gggatgattg cttgagctca ggagtttgag accaggctgg      5760
gcatcatagc aagacctcat ctctactaaa attcaaaaac aaaattagcc gggcatgatg      5820
```

```
gtgcatgcct gtagtctcag ctagttgggg agctaaggtg ggagaattgc ttgagcttgg    5880
gaagtcgagg ctgcagtcag ccctgattgt gccagtgcac tccggcctgg gtgacagagt    5940
gagaccctgt ctcaaaaaaa aaaagattct gtgtcagagc ccagcccagg agtttgaggc    6000
tgcaatgagc catgatttcc cactgcactc cagcctgagt gacagagcga gactccatct    6060
ctttaaaaac aaacaaaaaa ttatctgaat gatcctgtct ctaaaagaa gccacagaaa     6120 tgtttaaaaa cttcatcgac ttagcctgag tcataacggt taagaaagca cttaaacaga    6180
agcagaggct aattcagtgt cacatgagga agtagctgtc agatgtcaca taattacttt    6240
cgtaatagct cagattagaa tggctacccc attctctaga caaaatcaaa ttgtcctatt    6300
gtgactcttc taaaaatgaa gatgaagagc tatttaatga cacaccttgg attaaaacgg    6360
gaatcacatc ttaaagctaa aaatgaacct gcaagcctc taaatgagtc actgagcatc     6420
actagtgaca agtctcgggt gagcgtaaat gggtcatgac aagatgggac agcaacaaaa    6480
tcatggctta ggatcgacaa gaagttaaaa aacagctgca tctgttactt aagtttgtaa    6540
gacagtgccc tgagacctct agagaaaaga tgtttgttta cataagagaa agaggccaga    6600
catggtgtct cacacgttta atcccagcac tttgggaggc aggggcgggt ggatcacctg    6660
aggtcaggag ttcaagacta gcctggccaa catggtgaaa ccccgtctct actaaaaata    6720
caaaaattag ccgggcatgg tggcaggcgc ctataatccc agctactggg gaggctgagg    6780
caggagaatc acttgaaccc gggggacaga ggttgtagtg agccaagatc gcaccactgc    6840
actccagcct gggtcacaga gtgagactcc atctcaaaaa aaaaaagag agagagagag     6900 aaagaaatag aagagaagag ccatcttggc agggttattt tatatctgag caaggagttt    6960
aaatgagact agtttagatt gtctgctgat gcagccgtcc atagcagtac ccctaaaatc    7020
ccaccagaat acgggtccct ctaacccagt ggctggaaga accactgtct agagcaactt    7080
ttcttggaac tgtcccagct accaagtcag acaccaaggt ttatgccacc aggtaacacg    7140
ggaatcacag gtcatgtcg ctccggtcag attagttggc tttggcccct cgaccctgtg     7200
caggagctag ttctcagctt gcagctggaa gttccctct                           7239
```

<210> SEQ ID NO 29
<211> LENGTH: 21
<212> TYPE: DNA
<213> ORGANISM: Homo sapiens

<400> SEQUENCE: 29
tgactggcag atccagaggt t                                              21

<210> SEQ ID NO 30
<211> LENGTH: 21
<212> TYPE: DNA
<213> ORGANISM: Homo sapiens

<400> SEQUENCE: 30
gtagaatatg gacaggaaca c                                              21

<210> SEQ ID NO 31
<211> LENGTH: 21
<212> TYPE: DNA
<213> ORGANISM: Homo sapiens

<400> SEQUENCE: 31
cctgaagtgt aacaccccag a                                              21

```
<210> SEQ ID NO 32
<211> LENGTH: 21
<212> TYPE: DNA
<213> ORGANISM: Homo sapiens

<400> SEQUENCE: 32
tccctctcca gcacttctag t                                              21

<210> SEQ ID NO 33
<211> LENGTH: 31
<212> TYPE: DNA
<213> ORGANISM: Homo sapiens

<400> SEQUENCE: 33
tgctggagct gggacccagc attgaggagg a                                   31

<210> SEQ ID NO 34
<211> LENGTH: 27
<212> TYPE: DNA
<213> ORGANISM: Homo sapiens

<400> SEQUENCE: 34
tcagacacac acaacttcag tcgatag                                        27
```